(12) United States Patent
Mosher et al.

(10) Patent No.: US 9,125,945 B2
(45) Date of Patent: Sep. 8, 2015

(54) FORMULATIONS CONTAINING CLOPIDOGREL AND SULFOALKYL ETHER CYCLODEXTRIN AND METHODS OF USE

(71) Applicant: Cydex Pharmaceuticals, Inc., Lenexa, KS (US)

(72) Inventors: Gerold L. Mosher, Kansas City, MO (US); Rebecca L. Wedel, Lawrence, KS (US); Karen T. Johnson, Lawrence, KS (US); Stephen G. Machatha, Overland Park, KS (US); Jane A. Cowee, Kansas City, MO (US); Daniel J. Cushing, Phoenixville, PA (US)

(73) Assignee: Cydex Pharmaceuticals, Inc., Lenexa, KS (US)

( * ) Notice: Subject to any disclaimer, the term of this patent is extended or adjusted under 35 U.S.C. 154(b) by 0 days.

(21) Appl. No.: 14/507,693

(22) Filed: Oct. 6, 2014

(65) Prior Publication Data

US 2015/0025243 A1 Jan. 22, 2015

Related U.S. Application Data

(60) Continuation of application No. 13/689,898, filed on Nov. 30, 2012, now Pat. No. 8,853,236, which is a division of application No. 12/597,908, filed as application No. PCT/US2008/061697 on Apr. 26, 2008, now Pat. No. 8,343,995.

(60) Provisional application No. 60/914,555, filed on Apr. 27, 2007.

(51) Int. Cl.

| | |
|---|---|
| A61K 31/44 | (2006.01) |
| A61K 47/40 | (2006.01) |
| A61K 9/00 | (2006.01) |
| A61K 9/08 | (2006.01) |
| A61K 9/19 | (2006.01) |
| A61K 31/4365 | (2006.01) |
| A61K 31/724 | (2006.01) |
| A61K 31/727 | (2006.01) |
| A61K 45/06 | (2006.01) |
| A61K 47/48 | (2006.01) |
| B82Y 5/00 | (2011.01) |

(52) U.S. Cl.
CPC ............ *A61K 47/40* (2013.01); *A61K 9/0019* (2013.01); *A61K 9/08* (2013.01); *A61K 9/19* (2013.01); *A61K 31/4365* (2013.01); *A61K 31/44* (2013.01); *A61K 31/724* (2013.01); *A61K 31/727* (2013.01); *A61K 45/06* (2013.01); *A61K 47/48969* (2013.01); *B82Y 5/00* (2013.01)

(58) Field of Classification Search
USPC ................................................. 514/299, 451
See application file for complete search history.

(56) References Cited

U.S. PATENT DOCUMENTS

| | | | |
|---|---|---|---|
| 3,426,011 A | 2/1969 | Parmerter et al. | |
| 4,529,596 A | 7/1985 | Aubert et al. | |
| 4,847,265 A | 7/1989 | Badorc et al. | |
| 4,927,013 A | 5/1990 | Van Brunt et al. | |
| 5,134,127 A | 7/1992 | Stella et al. | |
| 5,241,059 A | 8/1993 | Yoshinaga | |
| 5,288,726 A | 2/1994 | Koike et al. | |
| 5,324,718 A | 6/1994 | Loftsson | |
| 5,376,645 A | 12/1994 | Stella et al. | |
| 5,436,242 A | 7/1995 | Koike et al. | |
| 5,472,954 A | 12/1995 | Loftsson | |
| 5,576,328 A | 11/1996 | Herbert et al. | |
| 5,632,275 A | 5/1997 | Browne et al. | |
| 5,874,418 A | 2/1999 | Stella et al. | |
| 5,989,578 A | 11/1999 | Bernat et al. | |

(Continued)

FOREIGN PATENT DOCUMENTS

| | | |
|---|---|---|
| CN | 1370072 | 9/2002 |
| CN | 1522159 | 8/2004 |

(Continued)

OTHER PUBLICATIONS

Dyszkiewicz-Korpantry et al., 2005, Approach to the assessment of platelet function: comparison between optical-based platelet-rich plasma and impedance-based whole blood platelet aggregation methods, Clin. Appl. Thromb. Hemost. 11:25-35.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPβCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of β-cyclodextrin, Proceedings of the Eighth International Symposium on Cyclodextrins, eds. Szejtli et al., Budapest, 373-376.

Gurbel et al., 2005, Clopidogrel Loading With Eptifibatide to Arrest the Reactivity of Platelets: Results of the Clopidogrel Loading With Eptifibatide to Arrest the Reactivity of Platelets (Clear Platelets) Study, Circulation 111:1153-1159.

Hennan et al., 1965, Prevention of experimental carotid and coronary artery thrombosis by the glycoprotein IIb/IIIa receptor antagonist CRL42796, Br. J. Pharmacol. 136(6):927-937.

(Continued)

*Primary Examiner* — Rei-Tsang Shiao
(74) *Attorney, Agent, or Firm* — Knobbe Martens Olson & Bear LLP

(57) ABSTRACT

The present invention provides compositions containing clopidogrel, present as a free base or a pharmaceutically acceptable salt thereof, and sulfoalkyl ether cyclodextrin (SAE-CD). The compositions can be liquid, suspension or solid compositions. They can be adapted for oral, peroral or parenteral administration. The SAE-CD serves to aid in dissolution and stabilization of the clopidogrel in aqueous media. The stability of clopidogrel against hydrolytic degradation, thermal degradation, and photolytic degradation are improved. SAE-CD provides improved results over other cyclodextrin derivatives. The SAE-CD-containing composition of clopidogrel can be provided in liquid form, solid form or as a reconstitutable powder. Both ready-to-use and concentrated liquid compositions can be prepared. The liquid composition is optionally available as a clear solution. The compositions herein can be administered perorally or parenterally and provide substantial pharmacokinetic, pharmacodynamic and/or therapeutic advantages over a tablet composition administered perorally and excluding SAE-CD.

10 Claims, 12 Drawing Sheets

(56) References Cited

U.S. PATENT DOCUMENTS

| | | |
|---|---|---|
| 6,046,177 A | 4/2000 | Stella et al. |
| 6,071,514 A | 6/2000 | Grinnell et al. |
| 6,133,248 A | 10/2000 | Stella |
| 6,153,746 A | 11/2000 | Shah et al. |
| 6,204,256 B1 | 3/2001 | Shalaby et al. |
| 6,248,729 B1 | 6/2001 | Coniglio et al. |
| 6,294,192 B1 | 9/2001 | Patel et al. |
| 6,383,471 B1 | 5/2002 | Chen et al. |
| 6,429,210 B1 | 8/2002 | Bousquet et al. |
| 6,451,339 B2 | 9/2002 | Patel et al. |
| 6,504,030 B1 | 1/2003 | Bousquet et al. |
| 6,509,348 B1 | 1/2003 | Ogletree |
| 6,569,463 B2 | 5/2003 | Patel et al. |
| 6,573,381 B1 | 6/2003 | Bousquet et al. |
| 6,693,115 B2 | 2/2004 | Asai et al. |
| 6,720,001 B2 | 4/2004 | Chen et al. |
| 6,737,411 B2 | 5/2004 | Valeriano et al. |
| 6,761,903 B2 | 7/2004 | Chen et al. |
| 6,767,913 B2 | 7/2004 | Lifshitz et al. |
| 6,800,759 B2 | 10/2004 | Valeriano et al. |
| 6,858,734 B2 | 2/2005 | Silva |
| 6,914,141 B2 | 7/2005 | Sherman |
| 6,923,988 B2 | 8/2005 | Patel et al. |
| 7,018,990 B2 | 3/2006 | Wong et al. |
| 7,034,013 B2 | 4/2006 | Thompson et al. |
| 7,074,928 B2 | 7/2006 | Lifshitz-Liron et al. |
| 7,259,261 B2 | 8/2007 | Valeriano et al. |
| 7,329,751 B2 | 2/2008 | Castaldi et al. |
| 7,446,200 B2 | 11/2008 | Deshpande et al. |
| 7,470,707 B2 | 12/2008 | Yun et al. |
| 7,629,331 B2 | 12/2009 | Pipkin et al. |
| 7,635,773 B2 | 12/2009 | Antle |
| 7,799,782 B2 | 9/2010 | Munson et al. |
| 8,236,782 B2 | 8/2012 | Mosher et al. |
| 8,343,995 B2 * | 1/2013 | Mosher et al. .......... 514/299 |
| 2002/0032149 A1 | 3/2002 | Kensey |
| 2003/0104048 A1 | 6/2003 | Patel et al. |
| 2004/0067995 A1 | 4/2004 | Wong et al. |
| 2004/0109888 A1 | 6/2004 | Pun et al. |
| 2004/0115287 A1 | 6/2004 | Chen et al. |
| 2005/0049226 A1 | 3/2005 | Silva |
| 2005/0049275 A1 | 3/2005 | Valeriano et al. |
| 2005/0096296 A1 | 5/2005 | Fikstad et al. |
| 2005/0143414 A1 | 6/2005 | Castaldi et al. |
| 2005/0164986 A1 | 7/2005 | Mosher et al. |
| 2005/0186267 A1 | 8/2005 | Thompson et al. |
| 2005/0203059 A1 | 9/2005 | Harrison et al. |
| 2005/0203122 A1 | 9/2005 | Doser et al. |
| 2005/0228012 A1 | 10/2005 | Yun et al. |
| 2005/0250738 A1 | 11/2005 | Mosher et al. |
| 2005/0256152 A1 | 11/2005 | Doser et al. |
| 2005/0276841 A1 | 12/2005 | Davis et al. |
| 2006/0003002 A1 | 1/2006 | Fikstad et al. |
| 2006/0041136 A1 | 2/2006 | Veverka et al. |
| 2006/0047121 A1 | 3/2006 | Sawant et al. |
| 2006/0074242 A1 | 4/2006 | Deshpande et al. |
| 2006/0100231 A1 | 5/2006 | Parthasaradhi et al. |
| 2006/0134206 A1 | 6/2006 | Iyer et al. |
| 2006/0154957 A1 | 7/2006 | Finkelstein et al. |
| 2006/0223845 A1 | 10/2006 | Turgeman et al. |
| 2007/0003615 A1 | 1/2007 | Jenkins et al. |
| 2007/0020196 A1 | 1/2007 | Pipkin et al. |
| 2007/0037842 A1 | 2/2007 | Lohray et al. |
| 2008/0108589 A1 | 5/2008 | Asai et al. |
| 2008/0113000 A1 | 5/2008 | Hunter et al. |
| 2008/0176893 A1 | 7/2008 | Dziennik et al. |
| 2008/0200533 A1 | 8/2008 | Krishnan |
| 2008/0220441 A1 | 9/2008 | Birnbaum et al. |
| 2009/0012042 A1 | 1/2009 | Ren et al. |
| 2009/0123540 A1 | 5/2009 | Pipkin et al. |
| 2009/0270348 A1 | 10/2009 | Antle |
| 2010/0093664 A1 | 4/2010 | Rowe |
| 2015/0005341 A1 | 1/2015 | Mosher et al. |

FOREIGN PATENT DOCUMENTS

| | | |
|---|---|---|
| CN | 1694688 | 11/2005 |
| CN | 1921834 | 2/2007 |
| CN | 101390856 | 3/2009 |
| EP | 0 579 435 | 1/1994 |
| FR | 2 769 313 | 4/1999 |
| JP | 05-504783 | 7/1993 |
| JP | 06-511513 | 12/1994 |
| JP | 2002-255814 | 9/2002 |
| KR | 20070034681 | 3/2007 |
| SI | 21748 | 3/2004 |
| WO | WO 91/11172 | 8/1991 |
| WO | WO 94/02518 | 2/1994 |
| WO | WO 97/29753 | 8/1997 |
| WO | WO 99/42111 | 8/1999 |
| WO | WO 03/002152 | 1/2003 |
| WO | WO 03/066637 | 8/2003 |
| WO | WO 2004/098713 | 11/2004 |
| WO | WO 2005/065649 | 7/2005 |
| WO | WO 2006/138317 | 12/2006 |
| WO | WO 2007/024472 | 3/2007 |
| WO | WO 2008/060934 | 5/2008 |
| WO | WO 2008/072836 | 6/2008 |
| WO | WO 2008/072939 | 6/2008 |
| WO | WO 2008/073759 | 6/2008 |
| WO | WO 2008/108291 | 9/2008 |
| WO | WO 2009/018069 | 2/2009 |
| WO | WO 2009/054095 | 4/2009 |
| WO | WO 2010/009335 | 1/2010 |

OTHER PUBLICATIONS

Higuchi et al., 1965, Phase Solubility Techniques, in Advances in Analytical Chemistry and Instrumentation, vol. 4, pp. 117-212, Reilly, C., ed, John Wiley & Sons Inc., United Kingdom.

Kolbe et al., 2002, Preparation and Characterization of Clopidogrel/ DIMEB Complex, J. Inclusion Phenomena and Macrocyclic Chemistry, 44:183-184.

Kristinsson et al., 1996, Dexamethasone-cyclodextrin-polymer co-complexes in aqueous eye drops, Investigative Ophthalmology & Visual Science, 37(6):1199-1203.

Lammers et al., 1971, Properties of cyclodextrins: Part VI. Water-soluble cyclodextrin-derivatives. Preparation and Analysis, Die Starke, 23(5):167-171.

Lammers et al., 1972, Properties of Cyclodextrins, Part VIII. Determination of the composition of inclusion complexes of hexane and 2,3-dinnethylbutane with cyclodextrin derivatives in aqueous solution, Recl. Trav. Chim. Pays-Bas 91:733-742.

Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.

Loftsson et al., 1994, The effect of water-soluble polymers on drug-cyclodextrin complexation, International Journal of Pharmaceutics (Netherlands), 110(2):169-177.

Loftsson et al., 1996, Effects of cyclodextrins and polymers on topical drug delivery to the eye-evaluations in humans, Proceedings of the 23rd International Symposium on Controlled Release of Bioactive Materials, pp. 453-454.

Loftsson et al., 1996, The influence of water-soluble polymers and pH on hydroxypropyl-β-cyclodextrin complexation of drugs, Drug Development and Industrial Pharmacy, 22(5):401-405.

Loftsson et al., 1997, Cyclodextrins as pharmaceutical excipients, Pharm. Technol. Eur. 9(5):26-34.

Loftsson et al., 1997, Enhanced complexation efficiency of cyclodextrins, Pharmaceutical Research, 14(11):S203.

Loftsson et al., 1998, Cyclodextrin solubilization of ETH-615, a zwitterionic drug, Drug Development and Industrial Pharmacy, 24(4):365-370.

Loftsson et al., 1998, The effect of water-soluble polymers on the aqueous solubility and complexing abilities of β-cyclodextrin, International Journal of Pharmaceutics, 163(1-2):115-121.

Loftsson et al., 1999, Methods to enhance the complexation efficiency of cyclodextrins, S.T.P. Pharma Sciences, 9(3):237-242.

(56) References Cited

OTHER PUBLICATIONS

Loftsson et al., 2001, Cyclodextrin solubilization of benzodiazepines: formulation of midazolam nasal spray, International Journal of Pharmaceutics, 212(1):29-40.

Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.

Loftsson et al., Oct. 1994, Polymer-cyclodextrin-drug complexes, Pharmaceutical Research, 11(10):S225.

Loftsson et al., Oct. 1996, Pharmaceutical applications of cyclodextrins. 1. Drug solubilization and stabilization, Journal of Pharmaceutical Sciences, , 85(10):1017-1025.

Loftsson et al., Sep. 16, 1996, Drug-cyclodextrin-polymer ternary complexes, European Journal of Pharmaceutical Sciences, 4(SUPPL):S144.

Loftsson et al., Sep. 1996, Solubilization of β-cyclodextrin, Eur. J. Pharm. Sci, 4(Suppl.):S143.

Loftsson et al., Sep. 2001, Sustained drug delivery system based on a cationic polymer and an anionic drug/cyclodextrin complex, Pharmazie, 56(9):746-747.

Loftsson, 1996, Topically effective acetazolamide eye-drop solution in man, Pharmaceutical Sciences, 2(6):277-279.

Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.

Loftsson, Apr. 2-6, 1995, The effect of polymers on cyclodextrin complexation, Book of Abstracts, 209th ACS National Meeting, 209(1):33-CELL.

Masson et al., 1999, Drug-cyclodextrin complexation in the presence of water-soluble polymers: enhanced solubility and percutaneous transport, ACS Symposium Series, 737 (Polysaccharide Applications), pp. 24-45.

Mehta et al., 2001, Effects of pretreatment with clopidogrel and aspirin followed by long-term therapy in patients undergoing percutaneous coronary intervention: the PCI-CURE study, The Lancet, 358:527-533.

Niitsu et al., Jan. 2008, Repeat oral dosing of prasugrel, a novel $P2Y_{12}$ receptor inhibitor, results in cumulative and potent antiplatelet and antithrombotic activity in several animal species, European Journal of Pharmacology, 579:276-282.

Pereillo et al., 2002, Structure and stereochemistry of the active metabolite of clopidogrel, Drug Metab. Disposition, 30(11):1288-1295.

Physician's Desk Reference, 2002, PLAVIX.RTM., Murray et al., eds, Medical Economics Company, Inc., Montvale, NJ, pp. 3084-3086.

Pickard et al., Mar. 2008, Clopidogrel—Associated Bleeding and Related Complications in Patients Undergoing Coronary Artery Bypass Grafting, Pharmacotherapy, 28:376-392.

Polymer Science, in Physical Pharmacy. Physical Chemical Principles in Pharmaceutical Sciences, 3rd edition, Martin et al., 1983, pp. 592-638.

Polymers and Macromolecules, in Physicochemical Principles of Pharmacy, 2nd edition, Florence et al., eds. pp. 281-334, 1988.

Qu, Q., et al., "Sulfoalkyl Ether .beta.-Cyclodextrin Derivatives: Synthesis and Characterizations," J. Inclusion Phenomena Macro. Chem. 43: 213-221, Kluwer Academic Publishers, Netherlands (2002).

Reist et al., 2000, Very Slow Chiral Inversion of Clopidogrel in Rats: A Pharmacokinetic and Mechanistic Investigation, Drug Metab. Disposition 28(12)1405-1410.

Remington's Pharmaceutical Sciences, 18th Edition, Gennaro ed., 1990, Hydrophilic Dispersons, pp. 291-294.

Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.

Schafer et al., 2009, Critical Review of Prasugrel for Formulary Decision Makers, Journal of Managed Care Pharmacy, 15(4):335-343.

Serebruany, 2009, Platelet Inhibition with Prasugrel and Increased Cancer Risks: Potential Causes and Implications, The American Journal of Medicine 122(5):407-408.

Siddique et al., May 2009, New antiplatelet drugs: beyond aspirin and clopidogrel, Int. J. Clin. Pract. 63(5):776-789.

Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78.

Small et al., 2008, Effect of ranitidine on the pharmacokinetics and pharmacodynamics of prasugrel and clopidogrel, Curr. Med. Res. Opin., 24(8):2251-2257.

Smith et al., 2007, Disposition and metabolic fate of prasugrel in mice, rats, and dogs, Xenobiotica 37(8):884-901.

Sramek et al., 1992, A Randomized and Blinded Comparison of Three Bleeding Time Techniques: the Ivy Method, and the Simplate II Method in Two Directions, Thromb. Haemost. 67(5):514-518.

von Beckerath et al., 2005, Absorption, Metabolization, and Antiplatelet Effects of 300-, 600-, and 900-mg Loading Doses of Clopidogrel: Results of the ISAR-CHOICE (Intracoronary Stenting and Antithrombic Regimen: Choose Between 3 High Oral Doses for Immediate Clopidrogrel Effect) Trial., Circulation, 112:2946-2950.

Waehre et al., 2006, Clopidogrel increases expression of chemokines in peripheral blood mononuclear cells in patients with coronary artery disease: results of a double-blind placebo-controlled study, Journal of Thrombosis and Haemostatis, 4(10):2140-2147 (abstract).

Wedel et al., Nov. 9-15, 2007, Effects of Modified Cyclodextrin Derivatives on the Solubility and Stability of Clopidogrel Bisulfate in Aqueous Formulations, 2007 AAPS Annual Meeting & Exposition, retrieved from the internet: URL:http://abstracts.aapspharmaceutica.com/ExpoAAPS07/CC/forms/attendee/i-ndex.aspx?content=sessionInfo&sessionId=1153.

Weerakkody et al., Jul. 2007, Comparison of speed of onset of platelet inhibition after loading doses of clopidogrel versus prasugrel in healthy volunteers and correlation with responder status, Am. J. Cardiol. 100:331-336.

Weerakkody et al., Sep. 2007, Greater Inhibition of Platelet Aggregation and Reduced Response Variability with Prasugrel Versus Clopidogrel: An Integrated Analysis, J. Cardiovasc. Pharmacol. Ther., 12(3):205-212.

Wegert et al., 2002, Effects of antiplatelet agents on platelet-induced thrombin generation, Int. J. Clin. Pharmacol. Ther., 40(4):135-141.

Wiviott et al., Nov. 15, 2007, Prasugrel versus Clopidogrel in Patients with Acute Coronary Syndromes, N. Engl. J. Med., 357(20):2001-2015.

International Search Report for International Appl. No. PCT/US08/61698, mailed Aug. 6, 2008.

Written Opinion of the International Search Authority for International Appl. No. PCT/US08/61698, mailed Aug. 6, 2008.

International Search Report for International Appl. No. PCT/US08/61697, mailed Aug. 26, 2008.

Written Opinion of the International Search Authority for International Appl. No. PCT/US08/61697, mailed Aug. 26, 2008.

Extended European Search Report for Application No. EP 08769199.4, European Patent Office, Rijswijk, Netherlands, mailed May 18, 2011.

Search Report for Chinese Patent Application No. 200880022506.5 issued by the Chinese Patent Office on Feb. 25, 2013.

* cited by examiner

FORMULATIONS CONTAINING CLOPIDOGREL AND SULFOALKYL ETHER CYCLODEXTRIN AND METHODS OF USE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

The present invention relates to composition containing clopidogrel and a sulfoalkyl ether cyclodextrin and to the uses thereof in the treatment of disorders and diseases that are therapeutically responsive to clopidogrel and to other methods of use thereof.

2. Description of the Related Art

Clopidogrel bisulfate, methyl (+)-(S)-α-(2-chlorophenyl)-6,7-dihydrothieno[3,2-c]pyridine-5(4H)-acetate sulfate (1:1), is an inhibitor of ADP-induced platelet aggregation acting by direct inhibition of adenosine diphosphate (ADP) binding to its receptor and of the subsequent ADP-mediated activation of the glycoprotein GPIIb/IIIa complex. Clopidogrel selectively inhibits the binding of adenosine diphosphate (ADP) to its platelet receptor and the subsequent ADP-mediated activation of the glycoprotein GPIIb/IIIa complex, thereby inhibiting platelet aggregation. Biotransformation of clopidogrel is necessary to produce inhibition of platelet aggregation. An active metabolite responsible for the activity of the drug has been isolated (Pereillo et al., *Drug Metab. Disposition* (2002), 30(11), 1288-1295). Clopidogrel also inhibits platelet aggregation induced by agonists other than ADP by blocking the amplification of platelet activation by released ADP. Clopidogrel does not inhibit phosphodiesterase activity.

Clopidogrel bisulfate is a white to off-white powder. It is practically insoluble in water at neutral pH but freely soluble at pH 1. U.S. Pat. No. 4,847,265 discloses the dextro-rotary form of clopidogrel. U.S. Pat. Nos. 7,074,928, 6,767,913, 6,504,030, 6,429,210, and 6,504,030 disclose polymorphic forms of clopidogrel hydrogen sulfate. U.S. Pat. Nos. 6,858,734, 6,800,759, and 6,737,411 disclose various methods for preparing clopidogrel. Salt forms, polymorphs, and processes for preparation of clopidogrel are disclosed in U.S. Pregrant Publications No. 20060154957, No. 20060100231, No. 20060074242, No. 20060047121, No. 20060041136, No. 20050256152, No. 20050228012, No. 20050203122, No. 20050143414, No. 20050049275, and No. 20050049226. PCT International Publication No. WO 03/66637 discloses a hydrochloride salt form of clopidogrel and the process for its preparation.

Clopidogrel is currently marketed in the United States under the trade name PLAVIX (Sanofi Aventis). It is supplied in tablet form containing 75 mg equivalents of the clopidogrel base, even though the drug is present in the bisulfate salt form. It is also available in generic tablet form (Apotex, Inc.). U.S. Pat. No. 6,914,141 discloses a tablet formulation containing clopidogrel bisulfate.

PLAVIX is an antiplatelet medication approved by the U.S. Food and Drug Administration to reduce athero thrombotic events in 1) patients with a history of recent myocardial infarction (MI), recent stroke, or established peripheral arterial disease (PAD), and 2) patients with acute coronary syndrome (unstable angina/non-Q-wave MI) including patients who are to be managed medically and those who are to be managed with percutaneous coronary intervention (percutaneous transluminal coronary angioplasty (PTCA), stent, atherectomy, etc.) or coronary artery bypass graft (CABG). PLAVIX is a prescription medication that when taken daily can help reduce the risk of having a future heart attack or stroke. U.S. Pat. No. 5,576,328 discloses a method of preventing secondary ischemic events by the administration of clopidogrel after onset of a primary ischemic event. U.S. Pat. No. 6,071,514 discloses methods of treating thrombotic disorders by administration of clopidogrel to subjects in need thereof. Von Beckerath et al. (*Circulation* (2005), 112, 2946-2950) disclose the results of a clinical study comparing the absorption, metabolism and antiplatelet effects of 300 mg, 600 mg and 900 mg loading doses of clopidogrel administered perorally prepared from crushed Plavix tablets. They report the maximum ADP-induced platelet aggregation occurs at about 4 hours. Plavix inhibited 5 uM ADP-induced platelet aggregation by approximately 23% (300 mg dose), 34% (600 mg dose), 39% (900 mg dose), with minimal differences in antiplatelet effect between the 600 and 900 mg doses. These time periods are substantially similar to those usually observed following administration of whole PLAVIX tablets (Weerakody et al. *Am. J. Cardiol.* 2007:100:331-336).

In the clinical setting, PLAVIX tablets are administered orally prior to certain interventional cardiology procedures such as percutaneous coronary intervention (PCI) in order to decrease a patient's platelet aggregation and thereby reduce the risk of reocclusion or restenosis during or after the procedure. The amount of clopidogrel administered to a patient is related to the projected time to the procedure for that patient. In general, the greater the amount of clopidogrel administered the shorter the time to reach the desired therapeutic effect (e.g. platelet aggregation inhibition). For an average dose (300 mg clopidogrel in a PLAVIX tablet), the typical time to reach the desired therapeutic effect (e.g. platelet aggregation inhibition) varies from two to five hours. If there is an immediate need for the procedure (for example, PCI in less than two to three hours), then a larger dose of clopidogrel is administered than would be administered if the procedure were to be performed after two, three or more hours. For example, a patient undergoing a procedure in 60-180 minutes post administration of clopidogrel may be administered 600 mg. For a procedure starting 180 minutes or longer after administration of clopidogrel, the patient may be administered 300 mg. The reason this dosing strategy being employed is that there is an apparent in vivo dose saturation effect, whereby increasing the dose does not increase the overall efficacy of the drug but merely increases the rate of therapeutic onset, i.e. increases the rate at which a target inhibition of platelet aggregation is achieved post-administration of the drug. The specific protocol used, and times before and after which larger or small doses are used varies between different institutions, but most use larger doses when procedures are performed more quickly post dosing.

However, it is undesirable to administer unnecessarily large amounts of clopidogrel due to its toxicology profile. Clopidogrel side effects include hemorrhage, stomach upset/pain, diarrhea, constipation, headache, dizziness, rash, flu-like symptoms, back/joint pain, unusually long bleeding, unusual or easy bruising/bleeding, black stools, vomiting, chest pain, swelling, depression, fever, persistent sore throat, unusual weakness, vision changes, slurred speech, confusion, severe rash, itching, severe dizziness, or trouble breathing.

Moreover, if a patient presents with a severe cardiac event, e.g. ACS (acute coronary syndrome), there is a need to treat the patient as quickly as possible in order to minimize the risk of myocardial damage, which increases rapidly with time. A clinician must be able to diagnose a patient as rapidly as possible in order to determine the appropriate emergency medical treatment as rapidly as possible. The goal is to be able to treat the patient who would require PCI within ninety minutes after presenting in a hospital with ACS, but this short time period is unrealistic or unreliable when using PLAVIX tablets. Moreover, while clopidogrel is contraindicated in major invasive emergency surgical procedures, such as CABG, it is indicated for minimally invasive emergency procedures, such as PCI. One standard treatment protocol at this time is as follows: 1) determine whether the patient is presenting with an ACS; 2) alert the catheter lab of incoming patient; 3) oral administration of 300-600 mg of clopidogrel (as PLAVIX tablet(s)); 4) transport patient to catheter lab; 5) perform coronary angiogram; 6) determine if medical therapy alone, PCI or CABG is most appropriate; and 7) if medical therapy alone is indicated treat the patient with long term (chronic) clopidogrel therapy; or 8) if PCI is indicated, perform PCI and maintain patient on long term (chronic) clopidogrel therapy; or 8) if CABG is indicated, delay CABG for until platelet aggregation returns to normal for the patient. If CABG is performed within 7 days after the patient has received a dose of clopidogrel, there is a high risk of major bleeding, hemorrhage-related complications, and transfusion requirements (Pickard et al. *Pharmacotherapy* (2008), 23, 376-392). Unfortunately, if administration of PLAVIX tablets is delayed until after a determination that PCI instead or CABG is indicated, there is an increased risk of reocclusion and restenosis to the patient undergoing PCI. In addition, it is difficult to administer an oral tablet to a sedated patient which is often the case in subjects undergoing coronary angiography.

Accordingly, it would be highly beneficial to this field of therapy to provide a formulation that provides a more rapid therapeutic onset without requiring such excessive doses as are currently administered.

Clopidogrel can be taken with another drug to treat a disorder or disease in a subject. Clopidogrel, when taken with aspirin, is recommended for people who have been hospitalized with heart-related chest pain or had a certain type of heart attack—conditions doctors call acute coronary syndrome (ACS). U.S. Pat. No. 7,018,990 discloses the combined administration of a factor Xa inhibitor with clopidogrel. U.S. Pat. No. 6,509,348 discloses the combined administration of an ADP-receptor blocking antiplatelet drug and a thromboxane A2 receptor antagonist and a method for inhibiting thrombus formation with the combination. U.S. Pat. No. 6,248,729 discloses the combined administration of an ADP-receptor blocking antiplatelet drug and antihypertensive drug for preventing a cerebral infarction. U.S. Pat. No. 5,989,578 discloses the combined administration of clopidogrel and an antithrombotic agent. The combined use of clopidogrel with other drugs is also disclosed in U.S. Pregrant Publications No. 20050043382 and No. 20040067995, and in published articles by Wegert et al. (Int. J. Clin. Pharmacol. Ther. (2002), 40(4), 135-141) and Gurbel et al. (Circulation, (2005), 111 (9):1153-1159).

Various U.S. patents and publications disclose formulations comprising clopidogrel, for example, U.S. Pat. Nos. 6,923,988, 6,761,903, 6,720,001, 6,569,463, 6,451,339, 6,429,210, 6,383,471, 6,294,192, and Publications No. 20060223845, No. 20060003002, No. 20040115287, No. 20030104048, No. 20020032149.

Cyclodextrins are cyclic carbohydrates derived from starch. The unmodified cyclodextrins differ by the number of glucopyranose units joined together in the cylindrical structure. The parent cyclodextrins contain 6, 7, or 8 glucopyranose units and are referred to as α-, β-, and γ-cyclodextrin respectively. Each cyclodextrin subunit has secondary hydroxyl groups at the 2 and 3-positions and a primary hydroxyl group at the 6-position. The cyclodextrins may be pictured as hollow truncated cones with hydrophilic exterior surfaces and hydrophobic interior cavities. In aqueous solutions, these hydrophobic cavities provide a haven for hydrophobic organic compounds, which can fit all, or part of their structure into these cavities. This process, known as inclusion complexation, may result in increased apparent aqueous solubility and stability for the complexed drug; however, the degree of stabilization will vary from drug to drug. The complex is stabilized by hydrophobic interactions and does not involve the formation of any covalent bonds.

Chemical modification of the parent cyclodextrins (usually at the hydroxyl moieties) has resulted in derivatives with sometimes improved safety while retaining or improving the complexation ability of the cyclodextrin. Of the numerous derivatized cyclodextrins prepared to date, only two appear to be commercially viable; the 2-hydroxypropyl derivatives (HP-β-CD or HPCD), neutral molecules being commercially developed by Janssen and others, and the sulfoalkyl ether derivatives (SAE-β-CD or SAE-CD), being developed by CyDex Pharmaceuticals, Inc.

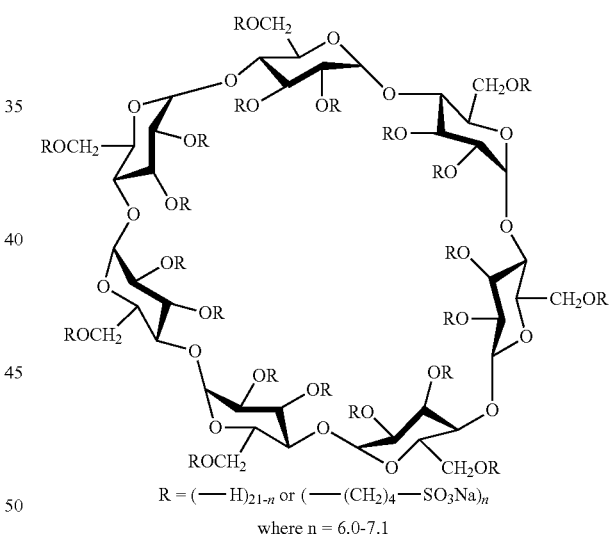

Sulfobutyl Ether-β-Cyclodextrin (Captisol®)

The SAE-CDs are a class of negatively charged cyclodextrins, which vary in the nature of the alkyl spacer, the salt form, the degree of substitution and the starting parent cyclodextrin. The sodium salt of the sulfobutyl ether derivative of beta-cyclodextrin, with an average of about 7 substituents per cyclodextrin molecule (SBE7-β-CD), is being commercialized by CyDex Pharmaceuticals, Inc. (Kansas) as CAPTISOL® cyclodextrin.

The anionic sulfobutyl ether substituent dramatically improves the aqueous solubility of the parent cyclodextrin. Reversible, non-covalent, complexation of drugs with the CAPTISOL® cyclodextrin generally allows for increased solubility and stability of some drugs in aqueous solutions.

However, the improved properties of SAE-CD over HP-β-CD in terms of binding to specific drugs are somewhat unpredictable. Many drugs are known to bind better with SAE-CD, while others are known to bind better with HP-β-CD. Moreover, CAPTISOL® cyclodextrin is relatively new, and its combined use with clopidogrel has not been evaluated or suggested in the prior art.

Various patent references disclosing compositions containing different salt, amorphous, crystalline and/or polymorphic forms of clopidogrel, optionally in the presence of another drug, suggest that the clopidogrel might be included in such compositions as a complex with a cyclodextrin. However, none of those references specifies or exemplifies SAE-CD.

Slovenian Patent No. SI 21748, which issued Oct. 31, 2005 to Rudolf Rucman (DIAGEN D.O.O.) discloses inclusion complexes of clopidogrel, as a free base or salt form, and cyclodextrins such as β-CD, γ-CD, methyl cyclodextrin and hydroxyalkyl cyclodextrin, the latter two being preferred. The patent also discloses the use of poly (vinyl pyrrolidone) having a molecular weight of 10,000-40,000 instead of cyclodextrin to solubilize the clopidogrel.

Kolbe et al. (*J. Inclusion Phenomena and Macrocyclic Chemistry* (2002 December), 44(1-4), pg. 183-184) disclose the formation of a complex of dimethylcyclodextrin and clopidogrel base in a 1:1 molar ratio. The complex precipitates from cold solution.

U.S. Application Publication No. 2004-0109888 to Pun et al. discloses a polymeric cyclodextrin material.

U.S. Application Publication No. 2005-0096296 to Fikstad et al. discloses a "pharmaceutical composition comprising: a therapeutically effective amount of a drug; a solubilizer; and a release modulator; wherein the release of the drug and solubilizer are synchronized."

U.S. Application Publication No. 2005-0276841 to Davis et al. discloses a "sustained-release biodegradable polymeric drug-eluting fiber", wherein the drug may be complexed with a cyclodextrin.

Clopidogrel is known to possess poor chemical stability in solution. Its degradation typically proceeds by a hydrolytic pathway whereby the ester form is converted to the carboxylic acid derivative. The stability of clopidogrel toward hydrolysis is pH dependent having a $t_{90}$ of about 52.7 days at pH 5.6 when stored at 37° C. temperature in 0.1M phosphate buffer (*Drug Metab. Disposition* (2000), 28(12), 1405-1410). A chemically stable solution formulation of clopidogrel would be useful in the art. Clopidogrel is known to undergo chiral inversion in vivo and in vitro (Reist et al., *Drug Metab. Dispos.* (2000), 28(12), 1405-1410); however, the (R)-enantiomer of clopidogrel is devoid of antithrombotic activity and can provoke convulsions in animals.

Due to the toxicology profile of clopidogrel and its typical administration at excessively high doses in a clinical procedure room environment, it would be desirable to provide a formulation that could avoid administration of the unnecessarily large amounts of clopidogrel, while at the same time provide the desired increase in the rate of therapeutic onset, i.e. a desired decrease in the time after drug administration that it takes to achieve the desired reduction in platelet aggregation.

SUMMARY OF THE INVENTION

The invention provides a pharmaceutical composition comprising clopidogrel (or any pharmaceutically acceptable salt thereof), sulfoalkyl ether cyclodextrin (SAE-CD), and optionally one or more pharmaceutically acceptable excipients. The SAE-CD is primarily responsible for solubilizing and stabilizing clopidogrel when the two are in the presence of an aqueous medium. The compositions of the invention reduce the chemical degradation of clopidogrel in solution. They also reduce the rate of chiral inversion of (S)-clopidogrel to (R)-clopidogrel. Even though the salt form of clopidogrel can be included in the instant formulation, the formulation does not necessarily require exposure of clopidogrel to strongly acidic conditions, since the free-base form, rather than the salt form, of clopidogrel can be employed in the formulation.

The invention provides an aqueous (optionally clear) liquid formulation comprising SAE-CD, clopidogrel, and an aqueous liquid carrier.

The formulation of the invention can be a single-dose or multi-dose formulation. The claimed formulation can also be self-preserved against microbial proliferation when the SAE-CD is present in amounts sufficient to stop or reduce the rate of microbial growth once the formulation has become contaminated with a microbe. The present formulation also improves the photochemical and thermal stability of clopidogrel over other cyclodextrin-based formulations.

The present invention also provides a SAE-CD-based solution of clopidogrel that is pharmaceutically stable and that does not require dilution prior to administration.

In some embodiments, 1) the sulfoalkyl ether cyclodextrin is present in an amount sufficient to provide a clear solution; 2) the SAE-CD is present at a concentration of about 20-600 mg/ml, 50-500 mg/ml or 100-400 mg/ml (2-60%, 5-50% or 10-40% wt./vol, respectively); 3) the SAE-CD is SBEx-β-CD, wherein x is 6.0 to 7.1 or 6.5 to 7; 4) the SAE-CD is SBEx-γ-CD, wherein x is about 6 to 8; and/or 5) the SAE-CD is a compound of the formula 1 (infra.) or a mixture of compounds thereof.

In some embodiments, 1) the clopidogrel is present in therapeutically effective amounts; and/or 2) clopidogrel as free base equivalents is present at a concentration of about 1.5 to 20 mg/ml (about 4.7 to 62 mM) or about 0.15 to 1.5 mg/ml (about 0.47 to 4.7 mM).

The invention also includes embodiments wherein: 1) the molar ratio of SAE-CD to clopidogrel is in the range of at least about 6:1 or about 6:1 to about 8:1 when the pH of the formulation is about or greater than about 3.5; 2) the molar ratio of SAE-CD to clopidogrel is less than about 6:1 when the pH of the formulation is less than about 3.5; 3) the clopidogrel is present at a concentration of about 7.5 mg/ml or less in an aqueous solution comprising about 37% wt/v or less of SAE-CD at a pH of about 5.5; 4) the clopidogrel is present at a concentration of about 0.5 mg/ml or less in an aqueous solution comprising about 2.5% wt/v or less of SAE-CD at a pH of about 5.5; 5) clopidogrel as free base equivalents is present at a concentration of about 0.15 to 20 mg/ml (about 0.47 to 62 mM); and/or 6) clopidogrel as bisulfate salt equivalents is present at a concentration of about 0.2 to about 26 mg/ml (about 0.47 to about 62 mM), about 0.2 to about 2 mg/ml (about 0.47 to about 4.7 mM), or about 2 to about 26 mg/ml (about 4.7 to about 62 mM).

In some embodiments, the formulation does not require dilution prior to administration to a subject. In other embodiments; the liquid formulation is dilutable with an aqueous based diluent without precipitation of the clopidogrel.

In some embodiments, the formulation further comprises a solubilizing agent, a flavoring agent, a sweetening agent, a viscosity inducing agent, an antioxidant, a buffering agent, an acidifying agent, a complexation enhancing agent, a lyophilizing aid (for example, bulking agents or stabilizing agents), an electrolyte, another therapeutic agent, an alkalizing agent, an antimicrobial agent, an antifungal agent or a combination thereof.

In general, the liquid formulation has improved photochemical stability and undergoes less photolytic degradation when exposed to fluorescent light as compared to another liquid formulation containing a different cyclodextrin or derivatized cyclodextrin.

In some embodiments, the formulation has improved chemical stability, such as improved stability against hydrolysis of clopidogrel, and undergoes less hydrolytic degradation of clopidogrel when exposed to aqueous conditions as compared to other formulations wherein the SAE-CD has been replaced by equimolar amounts of another cyclodextrin, such as HP-β-CD.

The invention also provides a method for preparing an aqueous (optionally clear) liquid formulation from a reconstitutable solid, the method comprising the steps of: providing a reconstitutable solid comprising clopidogrel, SAE-CD and optionally at least one other pharmaceutical excipient, wherein the solid is reconstitutable with an aqueous liquid, and the molar ratio of SAE-CD to clopidogrel is at least about 6:1, at least about 6:1 to 8:1, or at least about 8:1 when the pH of the aqueous liquid is greater than or equal to about 3.5; and reconstituting the solid with a sufficient amount of aqueous liquid carrier sufficient to at least suspend the reconstitutable solid, thereby forming the aqueous (optionally clear) liquid formulation.

In some embodiments, the liquid formulation has been prepared by reconstitution of a reconstitutable solid comprising at least SAE-CD and clopidogrel with an aqueous solution, wherein the reconstitutable solid is as defined herein. Conversely, the liquid formulation can be lyophilized or otherwise dehydrated to form a reconstitutable solid.

Some embodiments of the invention include those wherein: 1) the liquid formulation is a suspension; 2) the amount of liquid carrier added is sufficient to render the liquid formulation clear; 3) the formulation has a concentration of clopidogrel in the range from about 1.5 to 20 mg/ml or about 0.15 to 1.5 mg/ml; 4) the pH of the formulation approximates or is less than the pKa of clopidogrel; 5) the pH of the formulation approximates or is greater than the pKa of clopidogrel; 6) the pH of the formulation is in the range of about 4-8 for parenteral or oral delivery; 7) the pH of the formulation is in the range of about 1 to 3, 1 to 4, 1 to 8, 4 to 8, or 4 to 6 for oral delivery; 8) the molar ratio of SAE-CD to clopidogrel is less than about 6:1 when the pH of the formulation is less than about 3.5; 9) the molar ratio of SAE-CD to clopidogrel is in the range of at least about 6:1 or about 6:1 to 8:1 when the pH of the formulation is about or greater than about 3.5; and/or 10) the molar ratio is at least about 7.25:1 or 7.3:1 when the pH of the formulation is about or greater than about 8; the molar ratio is at least about 6.5:1 or 6.6:1 when the pH of the formulation is about or greater than about 5.5.

Some embodiments of the invention include those wherein: 1) the method further comprises the step of mixing the reconstitutable solid and aqueous liquid carrier; and/or 2) after reconstitution, the liquid formulation is ready for administration to a subject without requiring further dilution.

The invention also provides solid dosage forms. Such dosage forms can be administered orally, enterally, buccally, sublingually or by other known modes of administration for solid dosage forms. The solid dosage forms can include a tablet, capsule, powder, reconstitutable solid and other such dosage forms. Parenteral administration of the dosage form could be performed after dissolution of the dosage form in an aqueous liquid carrier. Orally administered solid oral dosage forms may require lower amounts of SAE-CD depending upon the targeted region of release in the gastrointestinal tract. For solid oral dosage forms releasing in the gastric region, the molar ratio of SAE-CD to clopidogrel can be less than 6 to 1, less than 5 to 1, less than 4 to 1, less than 3 to 1, less than 2 to 1, less than 1 to 1, less than 0.5 to 1, less than 0.25 to 1 and/or at least 0.05 to 1. For solid oral dosage forms releasing in the post-gastric region(s), the molar ratio of SAE-CD to clopidogrel can be at least 0.2 to 1, at least 0.5 to 1, at least 1 to 1, at least 2 to 1, at least 3 to 1, at least 4 to 1, at least 5 to 1, at least 6 to 1, at least 7 to 1, at least 8 to 1, and/or at most 100:1, at most 75:1, at most 50:1, at most 40:1, at most 35:1, at most 30:1, at most 20:1, at most 15:1, at most 12:1 or at most 10:1.

Combinations of the various upper and lower limits to the molar ratio of SAE-CD to clopidogrel, as set forth in this disclosure, can be used to provide different embodiments of the invention.

The invention also provides a method of administering clopidogrel comprising administering a ready-to-use liquid or a solid oral dosage formulation comprising a sulfoalkyl ether cyclodextrin and clopidogrel or a pharmaceutically acceptable salt thereof.

Some embodiments of the methods of the invention include those wherein: 1) the liquid formulation is administered parenterally, enterally or perorally; 2) the method further comprises the step of diluting a concentrate, according to the invention, with an aqueous liquid carrier prior to administration, thereby providing the ready-to-use liquid formulation; 3) the method further comprises the step of forming the liquid formulation by mixing an aqueous liquid carrier with a reconstitutable solid according to the invention; or 4) the liquid formulation is formulated as described herein.

The present invention also provides a method of treating, preventing or reducing the occurrence of a disease, disorder or condition having an etiology associated with platelet aggregation or of a disease, disorder or condition that is therapeutically responsive to clopidogrel therapy, the method comprising administering the formulation of the invention to a subject in need thereof. Some embodiments of the invention include those wherein the thrombotic disease, disorder, or condition is selected from the group consisting of myocardial infarction, stroke, vascular death in patients with established peripheral arterial disease (PAD), secondary ischemic events, acute coronary syndrome (unstable angina/non-Q-wave MI, heart attack, angina), transient ischemic attack, cerebrovascular disease cardiovascular disease, angina pectoris, deep vein thrombosis (DVT), pulmonary emboli (PE), sickle cell crisis, and cardiac arrhythmia.

The invention also provides a method of decreasing the time to therapeutic onset or the time required to reach the target therapeutic effect provided by clopidogrel, comprising administering parenterally, to a subject in need thereof, a formulation according to the invention; or administering orally or enterally, to a subject in need thereof, a formulation according to the invention. The formulation of the invention provides a reduced time to therapeutic onset and/or to target therapeutic effect as compared to a solid oral dosage form administered orally. The formulation of the invention also permits administration of a lower dose of clopidogrel to achieve a target therapeutic effect, e.g. target bleeding time or target inhibition of platelet aggregation, as compared to administration of a reference solid oral dosage form excluding SAE-CD to achieve the same target therapeutic effect.

The invention provides a method of increasing the bleeding time in a subject comprising administering to a subject in need thereof a composition comprising: SAE-CD; and no more than 900 mg, 750 mg, 675 mg, 600 mg, 450 mg, 375 mg, 300 mg, 225 mg, 200 mg, 150 mg, 100 mg, 75 mg, 50 mg, 40 mg, 30 mg, 25 mg, 20 mg, 15 mg, 12.5 mg, 10 mg, 7.5 mg, 5 mg, 2 mg, 1 mg, 0.75 mg, or 0.1 mg of clopidogrel, or in the range of 0.1 to 900 mg, 0.1 to 100 mg, 100 to 300 mg, about 300 mg, 300 to 600 mg, 300 to 900 mg, 600 to 900 mg, 50 to 600 mg, 75 to 600 mg, 150 to 600 mg, or 200 to 450 mg of clopidogrel, whereby the bleeding time of the subject increases by at least 10%, at least 15%, at least 20%, at least 25%, at least 30%, at least 40%, at least 50%, at least 75%, at least 100%, at least 150%, at least 200%, at least 250%, at least 300%, at least 400%, at least 500%, at least 700%, at least 900%, or at least 1000% during a period of no more than 200 min, 150 min, 120 min, 100 min, 90 min, 75 min, 60 min, 50 min, 45 min, 40 min, 30 min, 15 min, 10 min, 7.5 min, 5 min, 2.5 minutes, or of no more than 1 min, or of at least 10 seconds, or of 10 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min following administration of the formulation, wherein said increase is determined by comparison to the subject's bleeding time prior to administration of the composition. The upper limit to percentage increase in the bleeding time can be up to 10,000%, up to 9,000%, up to 7,500%, up to 5,000%, up to 4,000%, up to 2,500%, or up to 1,000%. The method can comprise daily or chronically administering to a subject in need thereof for several days, a week, several weeks, a month, several months, three to twelve months, or more than a year.

The invention also provides a method of increasing the bleeding time in a subject in need thereof just prior to the subject undergoing a medical procedure, the method comprising administering to the subject a formulation comprising SAE-CD and no more than 900 mg, 750 mg, 675 mg, 600 mg, 450 mg, 375 mg, 300 mg, 225 mg, 200 mg, 150 mg, 100 mg, 75 mg, 50 mg, 40 mg, 30 mg, 25 mg, 20 mg, 15 mg, 12.5 mg, 10 mg, 7.5 mg, 5 mg, 2 mg, 1 mg, 0.75 mg, or 0.1 mg of clopidogrel, or in the range of 0.1 to 900 mg, 0.1 to 100 mg, 100 to 300 mg, about 300 mg, 300 to 600 mg, 300 to 900 mg, 600 to 900 mg, 50 to 600 mg, 75 to 600 mg, 150 to 600 mg, or 200 to 450 mg of clopidogrel, wherein the formulation is administered no more than 200, 150, 100, 75, 60, 50, 40, 30, 15, 10, 7.5, 5 or 2.5 minutes prior to the procedure and the bleeding time of the subject increases by at least 10, 15, 20, 25, 30, 40, 50, 75, 100, 150, 200, 250, 300, 400, 500, 700, 900, or 1000%. during that time. The method can comprise acutely administering one or more doses to a subject in need thereof just prior to the subject undergoing a medical procedure. The method can also comprise acutely administering a single dose to a subject in need thereof just prior to the subject undergoing a medical procedure such a as an interventional or non-interventional procedure.

The invention provides a method of decreasing extent of (or potential for) platelet aggregation in the blood of a subject in need thereof comprising administering to the subject a formulation comprising SAE-CD and no more than 900 mg, 750 mg, 675 mg, 600 mg, 450 mg, 375 mg, 300 mg, 225 mg, 200 mg, 150 mg, 100 mg, 75 mg, 50 mg, 40 mg, 30 mg, 25 mg, 20 mg, 15 mg, 12.5 mg, 10 mg, 7.5 mg, 5 mg, 2 mg, 1 mg, 0.75 mg, or 0.1 mg of clopidogrel, or in the range of 0.1 to 900 mg, 0.1 to 100 mg, 100 to 300 mg, about 300 mg, 300 to 600 mg, 300 to 900 mg, 600 to 900 mg, 50 to 600 mg, 75 to 600 mg, 150 to 600 mg, or 200 to 450 mg of clopidogrel, whereby the percentage of platelet aggregation of the subject decreases by at least 5, 10, 15, 30, 40, 50, 60, 70, 80, 90, 96, 98, or 100% during a period of no more than 200 min, 150 min, 120 min, 100 min, 90 min, 75 min, 60 min, 50 min, 45 min, 40 min, 30 min, 15 min, 10 min, 7.5 min, 5 min, 2.5 minutes, or of no more than 1 min, or of at least 10 seconds, or of 10 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min following administration of the formulation.

The invention also provides a method of reducing the extent of (or potential for) platelet aggregation by at least 5, 10, 15, 30, 40, 50, 60, 70, 80, 90, 96, 98 or 100% in a subject in need thereof, the method comprising administering to the subject a formulation comprising SAE-CD and no more than 900, 750, 675, 600, 450, 375, 300, 225, 200, 150, 100, 75, 50, 40, 30, 25, 20, 15, 12.5, 10, 7.5, 5, 2, 1, 0.75, or 0.1 mg of clopidogrel; or 0.1 to 900 mg, 0.1 to 100 mg, 100 to 300 mg, about 300 mg, 300 to 600 mg, 300 to 900 mg, 600 to 900 mg, 50 to 600 mg, 75 to 600 mg, 150 to 600 mg, or 200 to 450 mg of clopidogrel on a daily basis.

The extent of or potential for platelet aggregation can be measured in vivo or ex vivo (in vitro).

Even though it can be administered orally, the clear liquid formulation/dosage form of the invention is particularly suitable for parenteral administration. In particular parenteral administration may be desirable when oral administration of the formulation may be undesirable, i.e. at occasions such as pre-procedure administration, post-procedure administration, and other such modes of administration, or when a subject is incapacitated or otherwise unable to receive an oral dose of the liquid or solid formulation. A procedure, in this particular case, is a medical procedure. The formulation of the invention can also be administered orally.

The present invention also provides methods of preparing an SAE-CD-based aqueous solution or solid dosage form of clopidogrel or a pharmaceutically acceptable salt thereof.

The invention also provides a kit comprising a first pharmaceutical composition comprising SAE-CD and a second pharmaceutical composition comprising clopidogrel or a pharmaceutically acceptable salt thereof.

The invention also provides a taste-masked oral formulation comprising sulfoalkyl ether cyclodextrin, clopidogrel, a pharmaceutically acceptable carrier, optionally one or more other excipients.

Unless otherwise specified, the term clopidogrel includes the free base or salt form, and the racemic form, optically pure (R) form, optically pure (S) form, or optically enriched form of the compound. It also includes the solid, suspended or dissolved forms of the compound. The salt form can be present as the hemihydrate, hydrate or anhydrous form. The salt can also be present in a pure crystalline form or polymorphic form.

The invention also provides a method of improving the stability of clopidogrel in a formulation comprising clopidogrel, the method comprising adding SAE-CD to the formulation in an amount sufficient to complex with a substantial portion of the clopidogrel present in the formulation, thereby stabilizing the clopidogrel.

The invention comprises a method of stabilizing a liquid formulation comprising clopidogrel and an aqueous liquid carrier, the method comprising: adding SAE-CD to the formulation in an amount sufficient to complex with a substantial portion of the clopidogrel, thereby stabilizing the clopidogrel. The term "stabilizing" is taken to mean reducing the rate of, reducing the extent of, and/or inhibiting of the degradation or chiral inversion of the clopidogrel in solution. The molar ratio of SAE-CD to clopidogrel can vary, as described herein, according to the pH of the liquid formulation and the desired stability of the formulation. Generally, the greater the portion of clopidogrel that is complexed with the SAE-CD, the greater the stabilization of the clopidogrel. Accordingly, the invention also provides a method of stabilizing (S)-clopidogrel against chiral inversion to (R)-clopidogrel, the method comprising including a sulfoalkyl ether cyclodextrin in a composition or formulation comprising an optically pure or enantiomerically enriched form of (S)-clopidogrel. By enantiomerically enriched is meant that the composition comprises a greater amount of (S)-clopidogrel than of (R)-clopidogrel.

Since the SAE-CD stabilizes clopidogrel in solution, a formulation or composition of the invention is also a "stabilized formulation" or "stabilized composition". A "stabilized formulation" or "stabilized composition" possesses enhanced stability as compared to an otherwise similar formulation excluding the SAE-CD.

The invention also provides a formulation comprising SAE-CD, clopidogrel, a second therapeutic agent, and a pharmaceutically acceptable carrier. The second therapeutic agent can be a nonsteroidal antiinflamatory drug, anticoagulant, selective factor Xa inhibitor, direct thrombin inhibitor, antiplatelet agent, platelet aggregation inhibitor, glycoprotein IIb/IIIa inhibitor, antisickling agent, hemorrheologic agent, thrombolytic agent, thrombolytic enzyme, tissue plasminogen activator, or combination thereof.

The invention also provides a method of treating a disease, condition or disorder comprising administering to a subject in need thereof: a therapeutically effective amount of clopidogrel in a composition or formulation of the invention, and a therapeutically effective amount of a second therapeutic agent, such as described herein. The second therapeutic agent may or may not be included in the same composition or formulation as the clopidogrel.

The invention also provides a method of identifying a responder or non-responder subject as regards responsiveness to clopidogrel therapy, the method comprising: administering to the subject a composition comprising an expected therapeutically effective amount of clopidogrel, and determining the subject's responsiveness to clopidogrel within a period of about 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after administration of the composition to the subject.

The composition can be adapted for peroral or parenteral administration. The expected therapeutically effective amount of clopidogrel will generally be about 50 to 600 mg, 0.1 to 900 mg, 1 to 900 mg, 10 to 900 mg, 0.1 to 100 mg, 25 to 750 mg, 50 to 600 mg, 75 to 600 mg, 75 to 500 mg, 100 to 300 mg, 100 to 400 mg, 150 to 600 mg, or 200 to 450 mg, 200 to 400 mg, 300 to 600 mg, 300 to 900 mg, 600 to 900 mg, about 0.1 mg, about 0.75 mg, about 1 mg, about 2 mg, about 5 mg, about 7.5 mg, about 10 mg, about 12.5 mg, about 15 mg, about 20 mg, about 25 mg, about 30 mg, about 40 mg, about 50 mg, about 75 mg, about 100 mg, about 150 mg, about 200 mg about 225 mg, about 300 mg, about 375 mg, about 450 mg, about 525 mg, about 600 mg, about 675 mg, about 750 mg, about 900 mg.

The step of determining can comprise: obtaining a sample of blood of the subject; and determining the extent of platelet aggregation in the subject's plasma by aggregometry, such as light transmittance or impedance platelet aggregometry. The step of administering can comprise peroral or parenteral administration. The composition can further comprise an amount of SAE-CD sufficient to solubilize and/or stabilize the clopidogrel.

The invention also provides a method of reducing the required therapeutic dose in a responder subject in need of clopidogrel to achieve a target therapeutic effect therein, the method comprising: parenterally or perorally administering to the subject a pharmaceutical composition comprising SAE-CD and a first therapeutically effective amount of clopidogrel, wherein the first therapeutically effective amount is at least 1.1-fold, at least 1.2-fold, at least 1.25-fold, at least 1.5-fold, at least 2-fold, at least 3-fold, at least 4-fold, at least 5-fold, at least 7-fold, at least 8-fold, at least 10-fold smaller, at least 15-fold, at least 20-fold, about 1.1 to about 20-fold, about 1.2-fold to about 15-fold, about 1.25-fold to about 10-fold, about 2-fold to about 10-fold, or about 3 fold to about 8-fold smaller than a second therapeutically effective amount, which is the amount of clopidogrel required to provide substantially the same therapeutic effect when clopidogrel is administered to the subject perorally in a reference solid pharmaceutical composition excluding SAE-CD. In some embodiments, the first therapeutically effective amount is no more than 900 mg, 750 mg, 675 mg, 600 mg, 450 mg, 375 mg, 300 mg, 225 mg, 200 mg, 150 mg, 100 mg, 75 mg, 50 mg, 40 mg, 30 mg, 25 mg, 20 mg, 15 mg, 12.5 mg, 10 mg, 7.5 mg, 5 mg, 2 mg, 1 mg, 0.75 mg, or 0.1 mg of clopidogrel, or in the range of 0.1 to 900 mg, 0.1 to 100 mg, 50 mg to 600 mg, 100 to 300 mg, about 300 mg, 300 to 600 mg, 300 to 900 mg, 600 to 900 mg, 50 to 600 mg, 75 to 600 mg, 150 to 600 mg, or 200 to 450 mg and the second therapeutically effective amount is greater than or about 300 mg to 900 mg for solid oral tablets, such as PLAVIX tablets.

The invention also provides a method of converting a subject that is a non-responder, in terms of oral administration of clopidogrel, to a responder, the method comprising parenterally administering clopidogrel to a subject in need thereof, thereby providing a therapeutic response to clopidogrel in the subject.

The invention also provides a method of escalating dose in a subject to achieve a target therapeutic effect in the subject, the method comprising: parenterally administering to the subject a first amount of clopidogrel, which can be 10 mg to 600 mg, 50 mg to 600 mg, 50 mg to 300 mg, about 50 mg, about 75 mg, about 100 mg, about 150 mg, about 225 mg, about 300 mg, about 375 mg, about 450 mg, about 525 mg, or about 600 mg; within a period of less than 120 min, less than about 100 min, less than about 90 min, less than about 75 min, less than about 60 min, less than about 45 min, less than about 30 min, less than about 20 min, less than about 15 min, less than about 10 min, less than about 5 min, or of 30 sec to 120 min, 30 sec to 100 min, 1 min to 100 min, 1 min to 90 min, 5 min to 90 min, 10 min to 75 min, 10 min to 60 min, 15 min to 60 min, 15 min to 45 min, or 15 min to 30 min after the parenteral administration, determining the first corresponding therapeutic effect achieved in the subject; if the extent of therapeutic effect achieved is less than the target therapeutic effect (for example, in terms of inhibition of platelet aggregation), parenterally administering to the subject a second amount of clopidogrel, wherein the second amount is about 0.5-fold, about 1-fold, about 1.25-fold, about 1.5-fold, or about 2-fold of the first amount, or the second amount is 0.1 mg to 1200 mg, 1 mg to 1000 mg, 5 mg to 900 mg, 10 mg to 900 mg, 25 mg to 750 mg, 50 mg to 750 mg, 50 mg to 600 mg, 0.1 mg to 100 mg, 1 mg to 75 mg, 100 mg to 300 mg, 300 mg to 600 mg, or 600 mg to 1200 mg; determining the second corresponding therapeutic affect achieved in the subject after administration of the second amount; and if the second corresponding therapeutic affect is less than the target therapeutic effect, repeating the steps of "parenterally administering to the subject a second amount of clopidogrel" and of "determining the second corresponding therapeutic affect achieved" until the target therapeutic effect is achieved.

The step of determining can comprise: obtaining a sample of plasma of the subject; and determining the extent of platelet aggregation in the subject's plasma by aggregometry. The step of obtaining can comprise: obtaining a sample of blood of the patient; and separating the plasma from the blood to form a plasma sample. The clopidogrel can be present in a composition comprising SAE-CD. The invention also provides an alternative method, wherein the clopidogrel is administered perorally.

The invention also provides a treatment protocol for a subject presenting with a cardiovascular condition, disease or disorder, optionally wherein the subject is initially not undergoing clopidogrel therapy the protocol comprising: a) determining whether or not the subject requires interventional or non-interventional medical treatment; and b) if the subject requires minimally invasive interventional medical treatment, then administering to the subject a pharmaceutical composition comprising SAE-CD and clopidogrel in an amount sufficient to provide a target therapeutic effect in the subject within a period of less than 120 min, less than about 100 min, less than about 90 min, less than about 75 min, less than about 60 min, less than about 45 min, less than about 30 min, less than about 20 min, less than about 15 min, less than about 10 min, less than about 5 min, or of 30 sec to 120 min, 30 sec to 100 min, 1 min to 100 min, 1 min to 90 min, 5 min to 90 min, 10 min to 75 min, 10 min to 60 min, 15 min to 60 min, 15 min to 45 min, or 15 min to 30 min, and conducting the minimally invasive interventional procedure; or c) if the subject requires non-interventional medical treatment, then administering to the subject a pharmaceutical composition comprising SAE-CD and clopidogrel in an amount sufficient to provide a target therapeutic effect in the subject within a period of 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min and providing to the subject said non-interventional medical treatment; or d) if the subject requires invasive interventional medical treatment, then not administering to the subject clopidogrel. In some embodiments, the minimally invasive interventional procedure is PCI. In some embodiments, the invasive interventional procedure is CABG. In some embodiments, the protocol comprises: determining whether the subject is presenting with an ACS; optionally, alerting the catheter lab of incoming subject; optionally, transporting subject to the catheter lab; performing coronary angiography on the subject; determining if PCI or CABG is indicated; and if PCI is indicated, parenterally administering a liquid composition comprising clopidogrel or perorally administering a composition comprising clopidogrel and SAE-CD, performing PCI, and optionally maintaining the subject on long term (chronic) clopidogrel therapy; or if CABG is indicated, performing the CABG, without prior administration of clopidogrel. The method of the invention can include additional steps as needed, such as sedating the subject and/or any step(s) indicated by an attending clinician/physician.

The invention provides a method of decreasing the time to peak or target therapeutic effect in a responder subject administered clopidogrel, the method comprising: administering to a subject in need thereof a first composition comprising SAE-CD and a therapeutically effective amount of clopidogrel sufficient to achieve a target therapeutic effect, whereby the time to peak or target therapeutic effect achieved by administration of the first composition is less than the time to peak or target therapeutic effect achieved by similar administration of an otherwise similar reference composition, excluding SAE-CD, and comprising substantially the same therapeutically effective amount of clopidogrel. In some embodiments, the time to peak or target therapeutic effect is reduced by at least 1.1-fold, at least 1.2-fold, at least 1.25-fold, at least 1.5-fold, at least 2-fold, at least 3-fold, at least 4-fold, at least 5-fold, at least 7-fold, at least 8-fold, at least 10-fold smaller, at least 15-fold, at least 20-fold, at least 40-fold, at least 50-fold, at least 75-fold, at least 100-fold, at least 120-fold, about 1.1-fold to about 120-fold, about 2-fold to about 120-fold, 2-fold to 100-fold, 2-fold to 75-fold, or 2-fold to 50-fold.

The invention also comprises combinations of the embodiments and aspects of the invention as detailed herein. Accordingly, the invention also includes combinations and sub-combinations of the individual elements of the embodiments or aspects of the invention as described herein. Other features, advantages and embodiments of the invention will become apparent to those skilled in the art by the following description, accompanying examples.

BRIEF DESCRIPTION OF THE DRAWINGS

The following drawings are part of the present specification and are included to further demonstrate certain aspects of the invention. The invention may be better understood by reference to one or more of these drawings in combination with the summary and detailed description of the embodiments presented herein.

DETAILED DESCRIPTION OF THE PREFERRED EMBODIMENT

Figure 1:
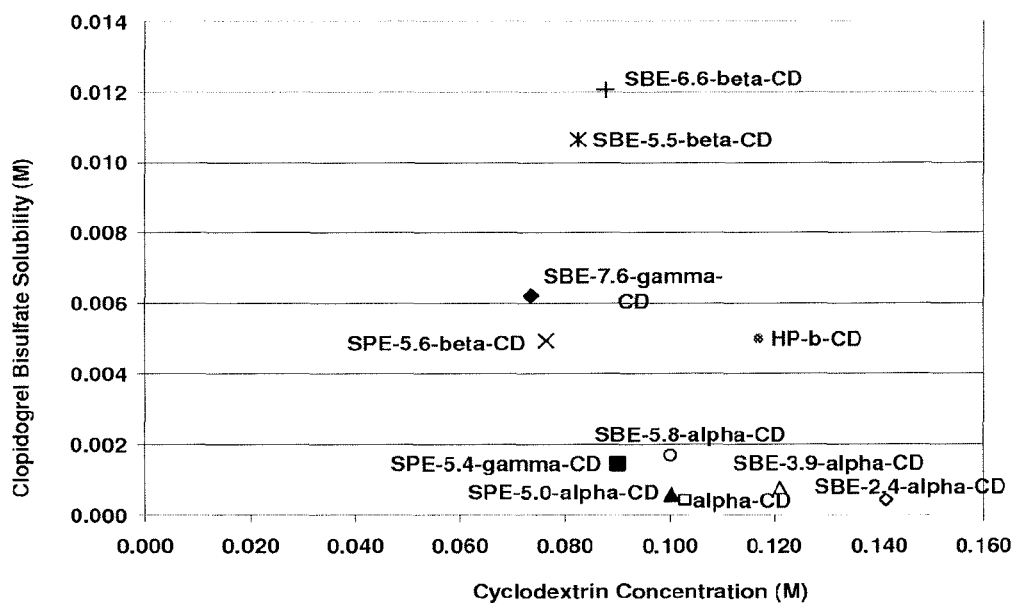
FIG. 1 depicts data obtained from a room temperature phase solubility study conducted with clopidogrel bisulfate and various different SAE-CD derivatives, underivatized cyclodextrins, and 2-hydroxypropyl-β-CD in water at pH ~5.5.

When prepared in ready-to-use (i.e., ready-to-administer) form, the liquid formulation of the invention does not require dilution prior to administration. When present as a concentrate, the present formulation is also dilutable in a broad range of aqueous based diluents without formation of precipitate. The formulation can be an oral, peroral, enteral or parenteral formulation. As used herein and unless otherwise specified, the term "clopidogrel" includes all neutral, free base, salt, crystalline, non-crystalline, amorphous, optically pure, optically enriched, racemic and/or polymorphic forms of the same. The clopidogrel can be present in anhydrous or hydrated form prior to use in present formulation. The salt of clopidogrel can be a pharmaceutically acceptable salt. The (S)-enantiomer of clopidogrel can be made according to U.S. Pat. No. 4,847,265. The (R)-enantiomer of clopidogrel can be made according to French Patent No. FR 2769313. The racemic form of clopidogrel can be made according to U.S. Pat. No. 4,529,596, and is commercially available from Sigma-Aldrich (St. Louis, Mo.)

As used herein, "pharmaceutically acceptable salt" refers to derivatives of clopidogrel wherein the active agent is modified by reacting it with an acid as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. Other salts are prepared from organic acids such as amino acids, acetic, propionic, butyric, succinic, glycolic, gluconic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanesulfonic, benzenesulfonic, oxalic, isethionic, and other acids known to those of ordinary skill in the art. Lists of other suitable salts are found in *Remington's Pharmaceutical Sciences*, 17th. ed., Mack Publishing Company, Easton, Pa., 1985 or 1995, the relevant disclosure of which is hereby incorporated by reference. Specific pharmaceutically acceptable salts of clopidogrel include the bisulphate salt, hydrobromide, napsylate, benzensulfonate, propylsulfate, perchlorate, naphthalenesulfonate, hydrochloride, isopropylsulfate, hydroiodide and mesylate.

As used herein, the term reconstitutable solid (reconstitutable composition) is taken to mean a solid capable of dissolution in an aqueous liquid medium to form a reconstituted liquid, wherein after dissolution the liquid medium is suitable for administration. In one embodiment, the reconstitutable solid forms a liquid formulation that is visibly clear when the solid is mixed with aqueous carrier. A reconstitutable pharmaceutical formulation according to the present invention comprises clopidogrel, SAE-CD and optionally, at least one other pharmaceutical excipient, wherein the molar ratio of SAE-CD to clopidogrel is as defined herein. A reconstitutable solid can be prepared by removal of the liquid medium from an aqueous liquid solution comprising SAE-CD and clopidogrel, and optionally other components to form the solid. The reconstitutable solid composition can comprise an admixture of a solid SAE-CD and a clopidogrel-containing solid and optionally at least one other pharmaceutical excipient, such that a major portion of the clopidogrel is not complexed with the SAE-CD prior to reconstitution. Alternatively, the composition can comprise a solid mixture of SAE-CD, clopidogrel and optionally at least one other pharmaceutical excipient, wherein a major portion of the clopidogrel is complexed with the SAE-CD prior to reconstitution. A reconstitutable solid will generally comprise less than 8% wt. water. This composition can be reconstituted with an aqueous solution to form a liquid formulation containing clopidogrel and other agents that can be administered to a subject. The liquid formulation used in the preparation of a reconstitutable formulation may be prepared as described herein for the diluted or concentrated liquid formulations. It may also be prepared to contain an SAE-CD and the clopidogrel at concentrations greater than typically used in the liquid formulation of the invention, while maintaining the same SAE-CD to clopidogrel molar ratio. Applicants note that any composition according to the invention can be dissolved or diluted with another liquid containing SAE-CD.

The reconstitutable composition can be prepared according to any of the following processes. A liquid formulation of the invention is first prepared, then a solid is formed by lyophilization (freeze-drying), spray drying, spray freeze-drying, vacuum-drying, antisolvent precipitation, various processes utilizing supercritical or near supercritical fluids, or other methods known to those of ordinary skill in the art of the liquid formulation to make a powder or a solid suitable for reconstitution. As noted above, the reconstitutable solid can be an admixture of the dry components, which is prepared by physically blending the components in the absence of excess moisture, i.e. the moisture should be less than about 60% RH.

A reconstitutable solid can be a powder, glassy solid, porous solid, granulate, pellet, bead, compressed solid, particulate or lyophile.

As used in regards to an SAE-CD-containing composition or formulation according to the invention, the term dilutable refers to a liquid formulation containing SAE-CD and clopidogrel, wherein the formulation can be further diluted with a clear aqueous liquid carrier at room temperature, e.g., ambient temperature such as a temperature of about 20°-28° C., preferably without significant precipitation of clopidogrel, i.e. if precipitation occurs it is less than or equal to about 3% wt. of clopidogrel, while providing a final clear solution when diluted to a clopidogrel concentration of about 0.15 to 10 mg/ml (free base equivalents). When a dilutable SAE-CD and clopidogrel-containing formulation is diluted with a non-clear solution, the resulting mixture may or may not be clear. A dilutable SAE-CD and clopidogrel-containing liquid can be diluted with another solution that does not contain SAE-CD, and the resulting diluted solution will have a lower concentration of solubilized clopidogrel preferably without causing significant precipitation of clopidogrel.

Exemplary liquids for diluting an oral formulation of the invention include commercially available beverages such as carbonated beverages, non-carbonated beverages, and juices. Exemplary carbonated beverages include flavored and non-flavored sodas, wherein the flavor is a cola, lemon, lime, root beer, bubble gum, cherry, orange and other flavors or mixtures thereof. Exemplary juices include apple, lemon, lime, orange, grape, cherry, cranberry, grapefruit, strawberry, kiwi, raspberry, blueberry, blackberry, dewberry, tangerine, pineapple, watermelon, cantaloupe, ginger, guava, mango, papaya, plum, apricot, pear, peach, nectarine, pomegranate, and other juices or mixtures thereof. Accordingly, an SAE-CD and clopidogrel-containing solution that is not dilutable according to the invention will form a significant amount (>3% wt. of active agent) of precipitate when diluted with another solution.

It should be noted that a formulation that is not dilutable with water alone at room temperature may be rendered dilutable with an aqueous solution that contains SAE-CD as long as the final molar ratio of clopidogrel to SAE-CD in the diluted solution is within the required range as described herein. The invention therefore provides a method of rendering dilutable a previously non-dilutable (as defined herein) clopidogrel-containing solution comprising the step of diluting the previously non-dilutable solution with a second solution containing SAE-CD such that the molar ratio of SAE-CD to clopidogrel in the diluted solution is as defined herein.

As used herein, a pharmaceutically acceptable liquid carrier is any aqueous liquid medium used in the pharmaceutical sciences for dilution or dissolution of parenteral, oral or per-oral formulations, such as water, aqueous buffer, aqueous organic solvent, and other liquids described herein or used in the pharmaceutical and/or food industry.

The formulation of the invention comprises clopidogrel and a sulfoalkyl ether cyclodextrin of the formula 1:

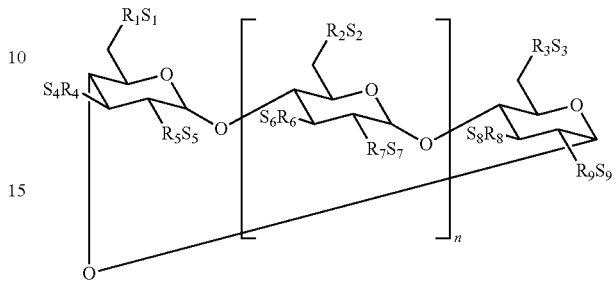

Formula 1 wherein:

n is 4, 5 or 6;

$R_1$, $R_2$, $R3$, $R_4$, $R_5$, RO, R7, Rs and Rg are each, independently, —O— or a —O—($C_2$-$C_6$ alkylene)-$SO_3$ group, wherein at least one of $R_1$ to $R_9$ is independently a —O—($C_2$-$C_6$alkylene)-$SO_3$, group, preferably a —O—$(CH_2)_m SO_3$-group, wherein m is 2 to 6, preferably 2 to 4, (e.g. —$OCH_2CH_2CH_2SO_3$— Or —$OCH_2CH_2CH_2CH_2SO_3$—); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine and ($C_4$-$C_8$)-cycloalkanolamine.

Particularly suitable SAE-CD derivatives include those wherein n is 5 or 6.

The SAE-CD used is available from CyDex Pharmaceuticals, Inc. (Lenexa, Kans.), and it is described in U.S. Pat. Nos. 5,376,645 and 5,134,127 to Stella et al, the entire disclosures of which are hereby incorporated by reference. U.S. Pat. No. 3,426,011 to Parmerter et al. discloses anionic cyclodextrin derivatives having sulfoalkyl ether substituents. Lammers et al. (Reel. Trav. Chim. Pays-Bas (1972), 91(6), 733-742); (Staerke (1971), 23(5), 167-171) and Qu et al. (J. Inclusion Phenom. Macro. Chem., (2002), 43, 213-221) disclose sulfoalkyl ether derivatized cyclodextrins. U.S. Pat. No. 6,153, 746 to Shah et al. discloses a process for the preparation of sulfoalkyl ether cyclodextrin derivatives. An SAE-CD can be made according to the disclosures of Stella et al., Parmerter et al., Lammers et al. or Qu et al., and if processed to remove the major portion (>50%) of the underivatized parent cyclodextrin, used according to the present invention. The SAE-CD can contain from 0% to less than 50% wt. of underivatized parent cyclodextrin.

The terms "alkylene" and "alkyl," as used herein (e.g., in the —O—($C_2$-$C_6$-alkylene) $SO_3$— group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl)cyclic alcohols.

Exemplary embodiments of the SAE-CD derivative of the invention include derivatives of the Formula II (SAEx-α-CD), wherein "x" ranges from 1 to 18; of the Formula III (SAEy-β-CD), wherein "y" ranges from 1 to 21; and of the Formula IV (SAEz-γ-CD), wherein "z" ranges from 1 to 24 such as:

| SAEx-α-CD | SAEy-β-CD | SAEz-γ-CD | Name |
|---|---|---|---|
| SEEx-α-CD | SEEy-β-CD | SEEz-γ-CD | Sulfoethyl ether CD |
| SPEx-α-CD | SPEy-β-CD | SPEz-γ-CD | Sulfopropyl ether CD |
| SBEx-α-CD | SBEy-β-CD | SBEz-γ-CD | Sulfobutyl ether CD |
| SPtEx-α-CD | SPtEy-β-CD | SPtEz-γ-CD | Sulfopentyl ether CD |
| SHEx-α-CD | SHEy-β-CD | SHEz-γ-CD | Sulfohexyl ether CD |

"SAE" represents a sulfoalkyl ether substituent bound to a cyclodextrin. The values "x", "y" and "z" represent the average degree of substitution as defined herein in terms of the number of sulfoalkyl ether groups per CD molecule.

Other exemplary SAE-CD derivatives include those of the formula SAEx-R-CD (Formula 2), wherein SAE is sulfomethyl ether (SME), sulfoethyl ether (SEE), sulfopropyl ether (SPE), sulfobutyl ether (SBE), sulfopentyl ether (SPtE), or sulfohexyl ether (SHE); x (average or specific degree of substitution) is 1-18, 1-21, 1-24, when R (ring structure of parent cyclodextrin) is α, β or γ, respectively, and CD is cyclodextrin.

Exemplary SAE-CD derivatives include SBE4-β-CD, SBE5.5-β-CD (Advasep® cyclodextrin), SBE7-β-CD (CAPTISOL® cyclodextrin), SPE5.6-β-CD, SBE6.1-γ-CD and SBE7.6-γ-CD. Particularly suitable SAE-CD derivatives include SAE-β-CD and SAE-γ-CD.

The present invention provides compositions containing a mixture of cyclodextrin derivatives, having the structure set out in the formulas above, where the composition overall contains on the average at least 1 and up to 3n+6 alkylsulfonic acid moieties per cyclodextrin molecule. The present invention also provides compositions containing a single type of cyclodextrin derivative, or at least 50% of a single type of cyclodextrin derivative.

It should be understood that other SAE-CD compounds of the above formulas may be used in the liquid formulation of the invention. These other SAE-CD formulations differ from SBE7-β-CD in their degree of substitution by sulfoalkyl groups, the number of carbons in the sulfoalkyl chain, their molecular weight, the number of glucopyranose units contained in the base cyclodextrin used to form the SAE-CD and or their substitution patterns. In addition, the derivatization of cyclodextrin with sulfoalkyl groups occurs in a controlled, although not exact manner. For this reason, the degree of substitution is actually a number representing the average number of sulfoalkyl groups per cyclodextrin (for example, SBE7-β-CD, has an average of 7 substitutions per cyclodextrin). In addition, the regiochemistry of substitution of the hydroxyl groups of the cyclodextrin is variable with regard to the substitution of specific hydroxyl groups of the hexose ring. For this reason, sulfoalkyl substitution of the different hydroxyl groups is likely to occur during manufacture of the SAE-CD, and a particular SAE-CD will possess a preferential, although not exclusive or specific, substitution pattern. Given the above, the molecular weight of a particular SAE-CD may vary from batch to batch and will vary from SAE-CD to SAE-CD. All of these variations can lead to changes in the complexation equilibrium constant which in turn will affect the required molar ratios of the SAE-CD to clopidogrel. The equilibrium constant is also somewhat variable with temperature and allowances in the ratio are required such that the agent remains solubilized during the temperature fluctuations that can occur during manufacture, storage, transport, and use. The equilibrium constant is also variable with pH and allowances in the ratio are required such that the agent remains solubilized during pH fluctuations that can occur during manufacture, storage, transport, and use. The equilibrium constant is also variable by the presence of other excipients (e.g., buffers, preservatives, antioxidants). Accordingly, the ratio of SAE-CD/clopidogrel may need to be varied (±) from the ratios set forth herein in order to compensate for the above-mentioned variables.

In some embodiments, the cyclodextrin derivatives of the present invention can be obtained as purified compositions, i.e., compositions containing at least 90 wt. % or 95 wt. % of cyclodextrin derivative(s) in terms of the total amount of cyclodextrin present, the balance of cyclodextrin comprising unreacted parent cyclodextrin. In a preferred embodiment, purified compositions containing at least 98 wt. % cyclodextrin derivative(s) are obtained. In some of the compositions of the invention unreacted cyclodextrin has been substantially removed, with the remaining impurities (i.e., <5 wt. % of composition) being inconsequential to the performance of the cyclodextrin derivative-containing composition.

According to other embodiments, the amount of unreacted parent cyclodextrin present in the SAE-CD is up to about or less than about 50% wt. of the SAE-CD, less than about 40% wt., less than 30% wt., or less than 20% wt. based upon the total dry weight of cyclodextrin.

By "clopidogrel/SAE-CD complex" is generally meant a clathrate or inclusion complex of a sulfoalkyl ether cyclodextrin derivative of the formula (I) and clopidogrel. The complex can be a binary or ternary complex (the salt form of clopidogrel is complexed). The ratio of SAE-CD:clopidogrel present in the molecular complex is in the range of about 1:1, on a molar basis. However, it should be understood that the molar ratio of SAE-CD to clopidogrel in the solution, as a whole, will be higher such that the SAE-CD will generally be, but need not be, present in molar excess over the clopidogrel. The amount of excess will be determined by the intrinsic solubility of the clopidogrel form, the expected dose of the clopidogrel form, and the binding constant for inclusion complexation between the specific clopidogrel form and the specific SAE-CD.

By "major portion" is meant at least about 50% by weight of the therapeutic compound. In various specific embodiments, greater than 50%, 60%, 75%, 90% or 95% by weight of the clopidogrel can be complexed with an SAE-CD while in the pharmaceutical formulation. The actual percent of drug that is complexed will vary according to the complexation equilibrium constant characterizing the complexation of a specific SAE-CD to clopidogrel and to the concentrations of SAE-CD and clopidogrel available for complexation.

FIG. 1 depicts the results of a phase solubility study per the method of Higuchi et al. in Phase Solubility Techniques, in Advances in Analytical Chemistry and Instrumentation (Ed. C N. Reilly, John Wiley & Sons Inc., Vol. 4 (1965), pg. 117-212) comparing the dissolution power of various cyclodextrins (SBE6.6-β-CD, SBE5.5-β-CD SBE7.6-γ-CD, SPE5.8-CC-CD, SPE5.6-β-CD, SPE5.4-γ-CD, SBE3.9-CC-CD, SPE5.0-β-CD, and SBE2.4-CC-CD) as compared to HP-β-CD and α-CD for binding with clopidogrel on a molar basis. The study was conducted in a titration apparatus that maintained the pH of the solutions at ~5.5. Samples were analyzed for clopidogrel content by HPLC with UV detection.

The results detailed in FIG. 1 indicate that SAE-CD generally outperforms HP-β-CD. In particular, SBE7-β-CD provides the highest degree of dissolution under the conditions tested. The SAE-β-CD and SAE-γ-CD derivatives are particularly useful for solubilizing clopidogrel. It should be noted that the performance of the various SAE-CD derivatives can be improved by varying test conditions and/or solution properties.

Figure 2A:
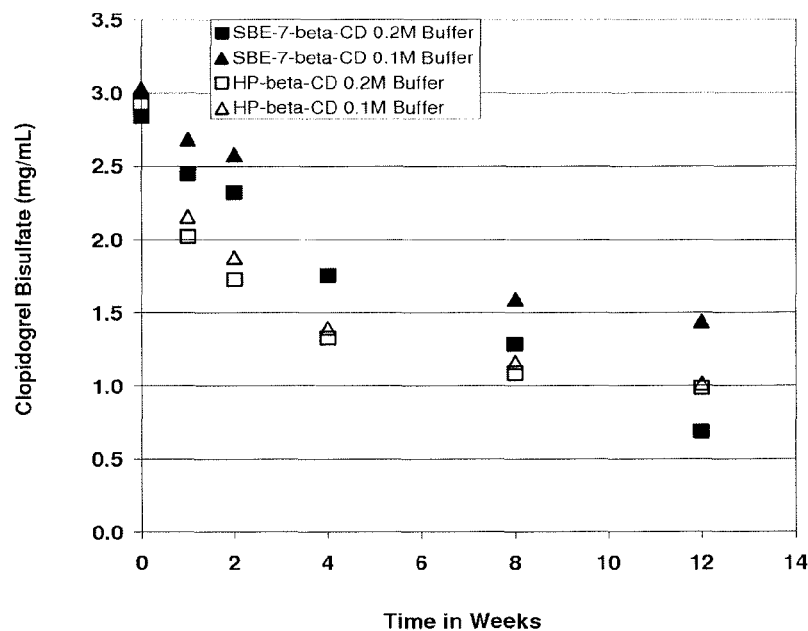
FIG. 2a depicts data obtained from a thermal stability study for the combination of clopidogrel and either SBE-β-CD or HP-β-CD conducted in a phosphate buffer (0.1 and 0.2 M) at pH 5.5 and 60° C. prepared according to Example 19.
Figure 2B:
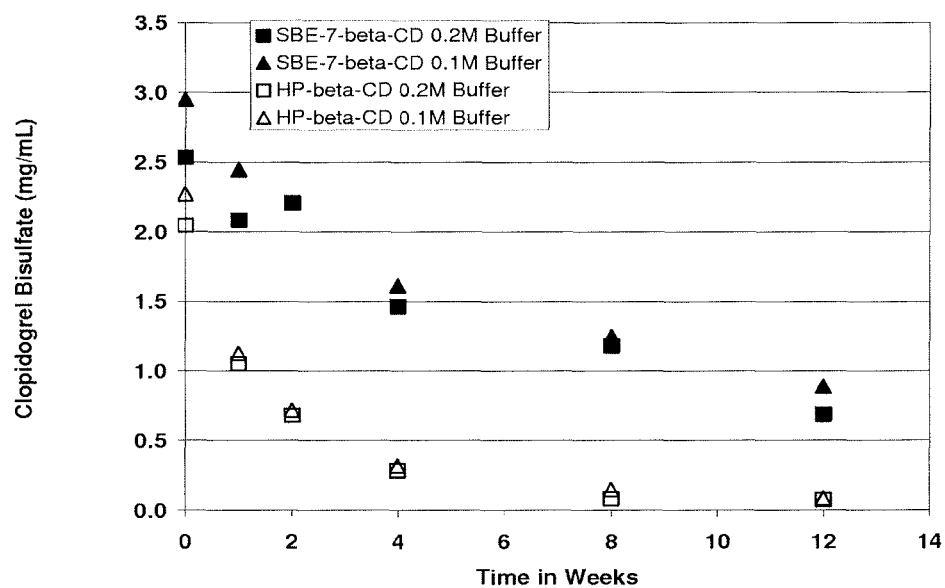
FIG. 2b depicts data obtained from a thermal stability study for the combination of clopidogrel and either SBE-β-CD or HP-β-CD conducted in a phosphate buffer (0.1 and 0.2 M) at pH 8.0 and 60° C. prepared according to Example 19.

The thermal and hydrolytic stability of clopidogrel in aqueous liquid formulations according to the invention was evaluated at various temperatures and pH's and phosphate buffer concentrations as detailed in Example 19. A similar evaluation was conducted for liquid formulations containing HP-β-CD rather than SAE-CD. The studies utilized equimolar amounts of the cyclodextrin derivatives, even though substantially more clopidogrel could be solubilized by the SAE-CD than with the HP-β-CD. These results (FIGS. 2a-2b) indicate a slower rate of thermal or hydrolytic degradation of clopidogrel in the presence of SAE-CD as compared to degradation of clopidogrel in the presence of HP-β-CD.

Figure 3A:
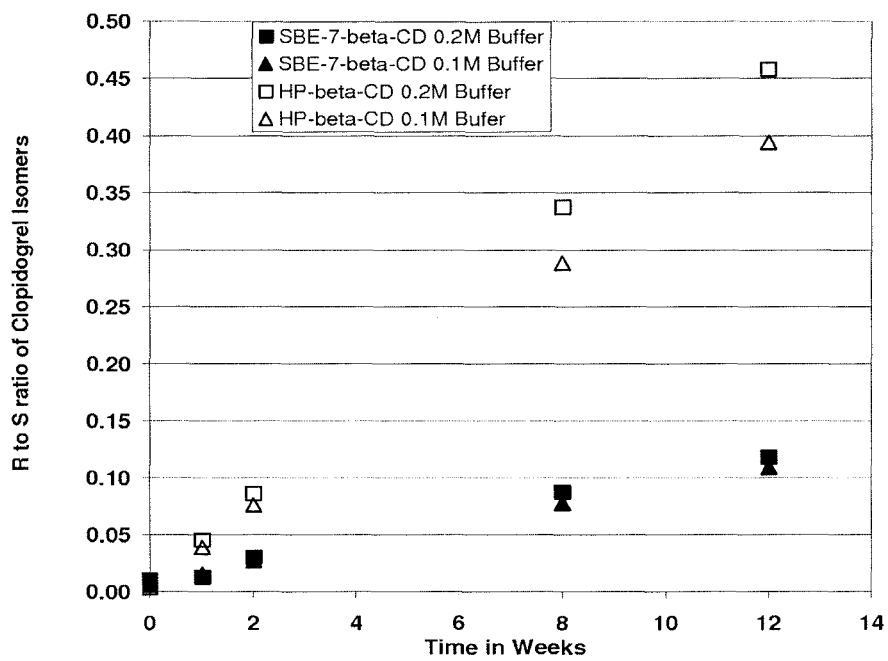
FIG. 3a depicts the chiral conversion data (from (S)-clopidogrel to (R)-clopidogrel) obtained from a thermal stability study for the combination of clopidogrel and either SBE-β-CD or HP-β-CD conducted in a phosphate buffer (0.1 or 0.2 M) at pH 5.5 and 40° C. prepared according to Example 19.
Figure 3B:
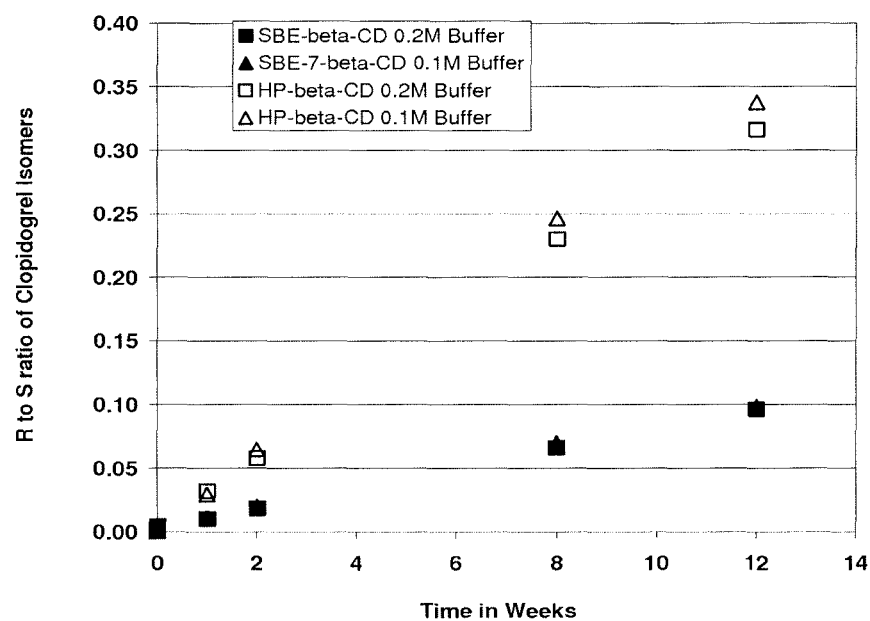
FIG. 3b depicts the chiral conversion (from (S)-clopidogrel to (R)-clopidogrel) data obtained from a thermal stability study for the combination of clopidogrel and either SBE-β-CD or HP-β-CD conducted in a phosphate buffer (0.1 or 0.2 M) at pH 8.0 and 40° C. prepared according to Example 19.

Another measure of the stability of clopidogrel is its rate of chiral inversion when present in a solution. The stability of clopidogrel in an aqueous liquid formulation according to the invention was evaluated at various temperatures and pH's and phosphate buffer concentrations as detailed in Example 19. A similar evaluation was conducted for liquid formulations containing HP-β-CD rather than SAE-CD. The rate of chiral conversion from (S)-clopidogrel to (R)-clopidogrel is dependent upon pH of the medium as is seen by comparing the ratio of enantiomers (R:S) in the pH ~5.5 and the pH ~8 formulations (FIGS. 3a-3b). It should be noted that the formulations with SAE-CD demonstrate a significant improvement in clopidogrel stabilization over those containing HP-β-CD, i.e. substantially less conversion of S-clopidogrel to R-clopidogrel. The results (FIGS. 3a-3b) establish the superiority of SAE-CD over HP-β-CD in stabilizing clopidogrel against chiral inversion in solution.

The photochemical stability of two SAE-CD based formulations and an HP-β-CD based formulation was evaluated as detailed in Example 19. A portion of each formulation was exposed to fluorescent light over a period of nine days. At various time points, aliquots of solution were withdrawn and analyzed by HPLC to determine their impurity profile and isomeric content.

Figure 4A:
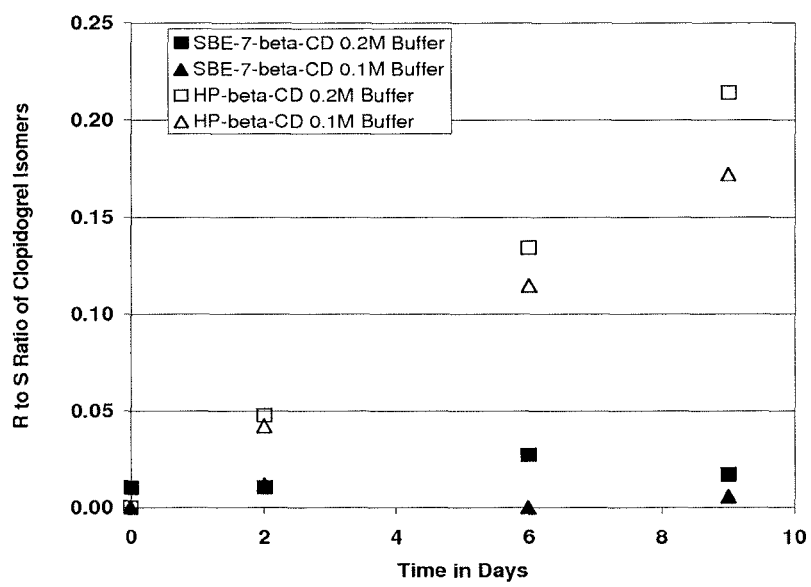
FIG. 4a depicts the chiral conversion (from (S)-clopidogrel to (R)-clopidogrel) data obtained from a fluorescent light stability study for the clopidogrel and either SBE-β-CD or HP-β-CD conducted in a phosphate buffer (0.1 or 0.2 M) at pH 5.5 and 29° C.
Figure 4B:
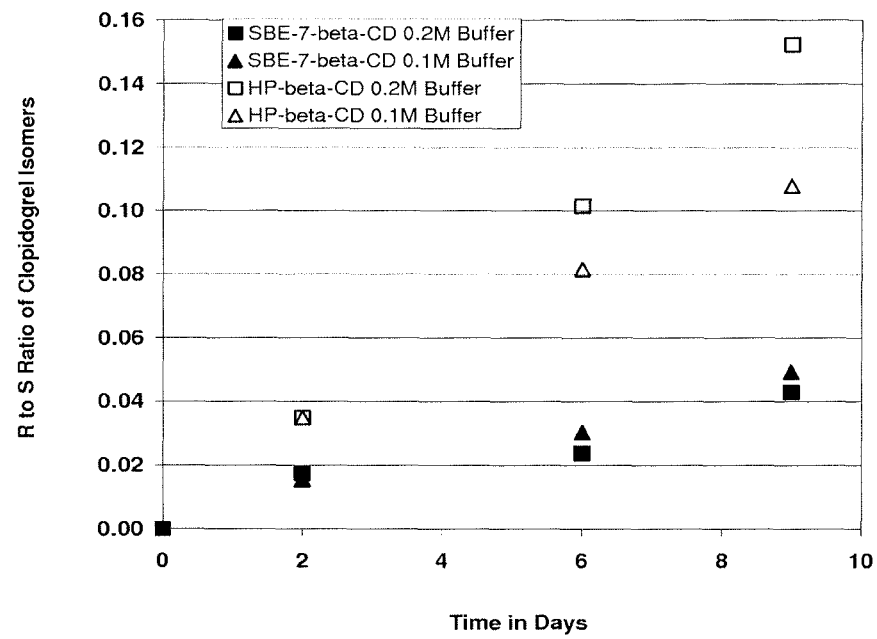
FIG. 4b depicts the chiral conversion (from (S)-clopidogrel to (R)-clopidogrel) data obtained from a fluorescent light stability study for the clopidogrel and either SBE-β-CD or HP-β-CD conducted in a phosphate buffer (0.1 or 0.2 M) at pH 8.0 and 29° C.

FIGS. 4a and 4b depict the results of a stability assay to determine the impact of the fluorescence irradiation upon the chiral inversion of the clopidogrel. The results establish the unexpectedly greater stabilization of clopidogrel by SBE-β-CD toward chiral inversion (and ultimate racemization) as compared to the limited degree of stabilization provided by HP-β-CD.

The chemical stability of the liquid formulations of the invention, in terms of formation of a precipitate, can be enhanced by adjusting the pH of the liquid carrier. The chemical stability can also be enhanced by converting the liquid formulation to a solid or powder formulation.

Figure 5:
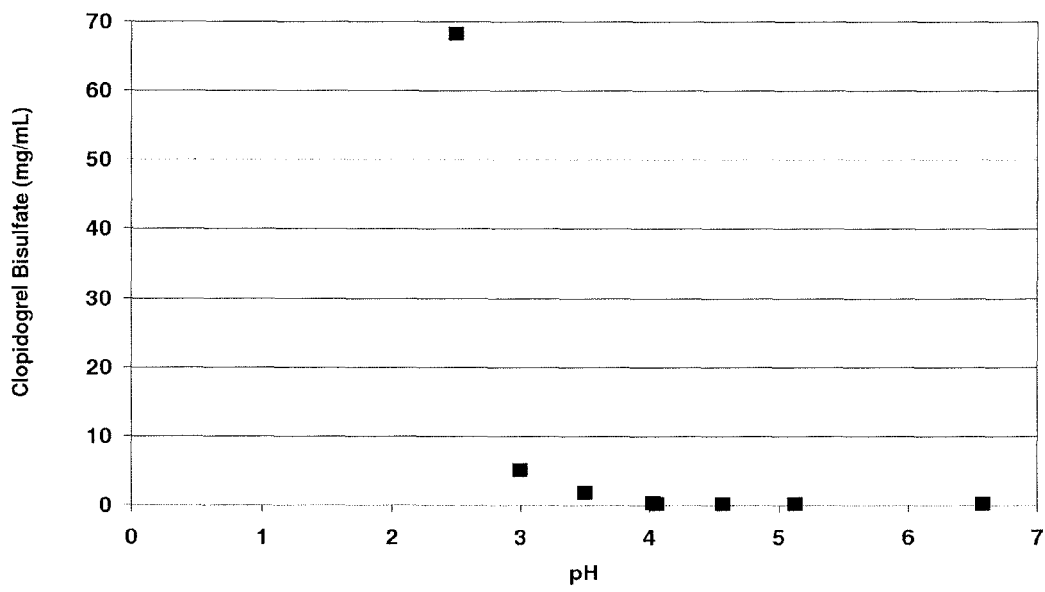
FIG. 5 depicts data regarding the pH solubility profile of clopidogrel bisulfate at ambient temperature.

The pH of water (for distilled and/or deionized water) in which a composition or formulation of the invention is placed for reconstitution can generally range from 1 to 8, provided the water does not include a substantial amount of a buffer or excludes a buffer; however, compositions or formulations having higher or lower pH values can also be prepared. The pH can be varied according to the intended mode of administration to a subject. The pH of a parenteral formulation can generally range from about pH 4 to about pH 8 or about pH 4 to about pH 6. The pH of an oral formulation will generally range from about pH 1 to about pH 8, about pH 4 to about pH 8, about pH 4 to about pH 6, about pH 1 to about pH 3, or about pH 1 to about pH 4. The pH solubility profile (FIG. 5) indicates that the solubility of clopidogrel (in the absence of a cyclodextrin derivative) is dependent upon pH. At a solution pH of about 3, the solubility of clopidogrel bisulfate is about 5.0 mg/ml. Below about pH 3, the solubility of clopidogrel increases dramatically, and above about pH 3, the solubility of clopidogrel decreases as follows:

| Solution pH | Solubility of Clopidogrel (mg/ml; approximate) |
| --- | --- |
| 3.5 | 1.79 |
| 4.0 | 0.279 |
| 4.5 | 0.171 |
| 5.12 | 0.083 |
| 6.60 | 0.082 |

Figure 6A:
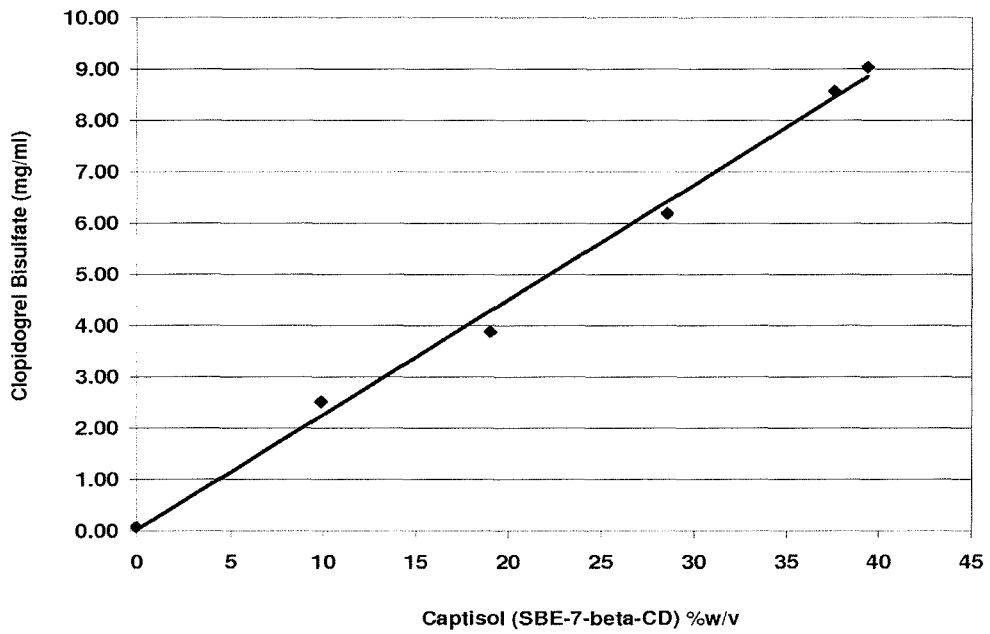
FIG. 6a depicts a phase solubility diagram for clopidogrel bisulfate (mg/ml) in the presence of SAE-CD (wt./vol %) at 25° C. in water with pH adjusted to 5.5.
Figure 6B:
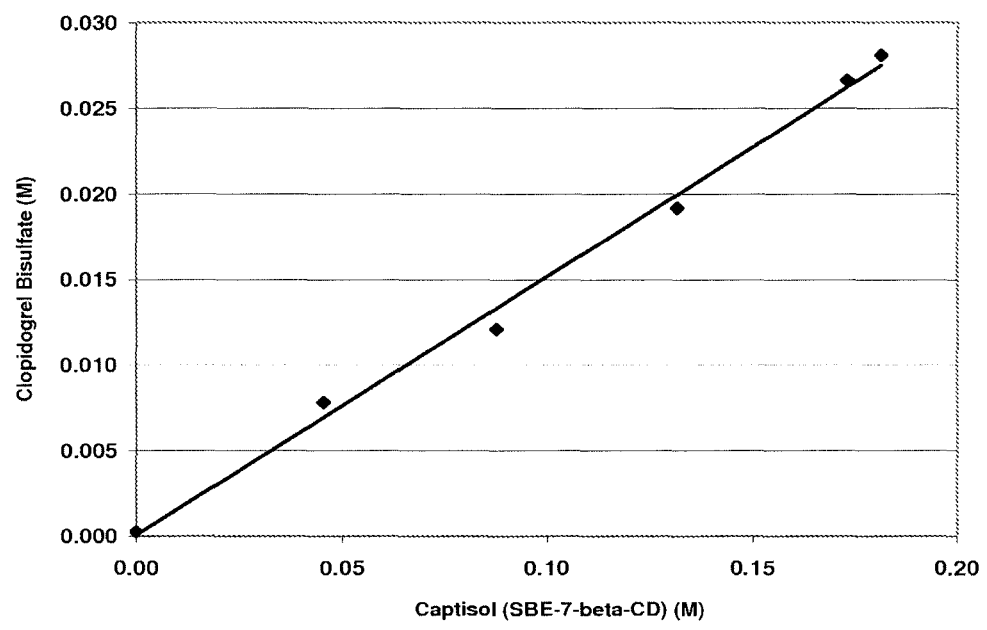
FIG. 6b depicts a phase solubility diagram for clopidogrel bisulfate (M) in the presence of SAE-CD (M) at 25° C. in water with pH adjusted to 5.5.

The phase solubility profiles of clopidogrel in SAE-CD at pH ~5.5 (FIGS. 6a and 6b) indicate that the solubility of the clopidogrel is dependent upon the cyclodextrin content. The slope of the line in FIG. 6b is about 0.15 indicating that the approximate minimum molar ratio of SBE-β-CD to clopidogrel required to dissolve the clopidogrel at pH 5.5 is at least about 6:1. As the concentration of SAE-CD is increased, greater amounts of clopidogrel can be dissolved and more concentrated solutions of clopidogrel can be prepared. Thus, concentrated formulations of clopidogrel can be prepared by using higher concentrations of SAE-CD. For parenteral applications, concentrated solutions would reduce the administration volume and potentially allow for faster administration. Concentrated solutions would also allow for peroral administration of doses in smaller volumes, and the required higher SAE-CD concentrations would provide improved antimicrobial action as well as potentially improved taste masking. In addition, dilute solutions can also be prepared, and the amount of cyclodextrin required would be reduced. The dilute solutions would allow for slower administration of the formulation and potentially better control of the dose administered over time.

The invention also provides a taste-masked oral formulation comprising sulfoalkyl ether cyclodextrin, clopidogrel, a pharmaceutically acceptable carrier and optionally other ingredients. In some embodiments, a taste-masked formulation comprises SAE-CD, clopidogrel, a pharmaceutically acceptable carrier, and aqueous solvent, suspending agent, buffer, surfactant, cosolvent and/or a flavoring agent such as mannitol, glucose, sucrose, xylitol and others known to those of ordinary skill in the art. Examples 15 and 17 describe exemplary taste-masked formulations comprising clopidogrel bisulfate, SAE-CD and a sugar, such as mannitol or D-glucose, respectively. The SAE-CD and clopidogrel molar ratio required may depend upon its mode of administration, the pH of a formulation containing the same, the pH of an intended environment of delivery. Typically the molar ratio can be within the range of 6:1 and 8:1, 6:1 to 10:1, 5:1 to 12:1, 4:1 to 15:1, 5:1 to 14:1, 6:1 to 13:1, or 6:1 to 12.5:1; and/or at least 0.05:1, at least 0.25:1, at least 0.2:1, at least 0.5:1, at least 1:1, at least 2:1, at least 3:1, at least 4:1, at least 5:1, at least 6:1, at least 7:1, or at least 8:1; and/or at most 100:1, at most 75:1, at most 50:1, at most 40:1, at most 35:1, at most 30:1, at most 25:1, at most 20:1, at most 15:1, at most 14:1 at most 12.5:1, at most 12:1, at most 10:1, at most 8:1, at most 6:1, at most 5:1, at most 4:1, at most 3:1, or at most 2:1. The reconstituted pH of the formulations can be low, e.g. between pH 1-2, which is suitable for oral use. The formulation of the invention can comprise clopidogrel in combination with a second therapeutic agent. The second therapeutic agent can be selected from the group consisting of: nonsteroidal anti-inflammatory drugs like piroxicam or aspirin; anticoagulants (e.g. warfarin, antithrombin III, unfractionated heparin, heparinoids like danaparoid, low molecular weight heparins like enoxaparin, selective factor Xa inhibitors like fondaparinux, and direct thrombin inhibitors like argatroban and bivalirudin); antiplatelet agents (e.g. anagrelide, dipyridamole, aggregation inhibitors like cilostazol and cangrelor, and glycoprotein IIb/IIIa inhibitors like eptifibatide and tirofiban); antisickling agents like hydroxyurea; hemorrheologic agents like pentoxifylline; and thrombolytic agents (e.g. biologic response modifiers like drotrecogin alpha and pexelizumab, thrombolytic enzymes like streptokinase and urokinase, and tissue plasminogen activators like alteplase and tenecteplase). This is demonstrated in Examples 24 and 25, where clopidogrel is formulated in combination with tirofiban hydrochloride monohydrate and enoxaprin sodium.

In some embodiments, the second therapeutic agent is used to treat sickle cell disease. Exemplary of such second therapeutic agents are: 1) drugs included in management protocols for sickle cell patients experiencing pain, fever-febrile illness acute chest syndrome, acute splenic sequestration, aplastic crisis, acute stroke or neurologic events; 2) folic acid supplementation, e.g. as part of a hydroxyurea treatment protocol; 3) NSAID, such as ibuprofen, acetaminophen, aspirin, codeine, morphine, hydromorphone, and ketorolac; 4) antibiotic, such as penicillin, penicillin derivatives, cephalosporins (such as ceftriaxone, cefotaxime, and others known to those in the art), macrolides (such azithromycin, erythromycin), clindamycin and vancomycin; 5) deferoximine, such as part of an iron chelation treatment protocol due to chronic transfusion requirements; 6) bronchodilators; 7) diuretic, such as furosemide; 8) anxiolytics, such as lorazepam, midazolam or hydroxyzine pamoate; 9) α-agonist, such as etilefrine, phenylephrine, epinephrine, phenylpropanolamine, pseudoephedrine, or terbutaline; 10) hydralazine; 11) pentoxifylline; 12) diltiazem; 13) gonatropin-releasing hormone analog such as leuprolide or flutamide; 14) diethylstilbestrol; and 15) combinations thereof.

The amount of the other drug present and thus the ratio of clopidogrel to the other drug present will depend upon the desired clinical effect. However, guidance as to the relative doses of each drug can be obtained from the resources of regulatory agencies such as the U.S. Food and Drug Administration, or other similarly recognized authority in Canada (Health Canada), Mexico (Mexico Department of Health), Europe (European Medicines Agency (EMEA)), South America (in particular in Argentina (Administración Nacional de Medic amentos, Alimentos y Tecnologia Medica (ANMAT)) and Brazil (Ministerio da SaV́de)), Australia (Department of Health and Ageing), Africa (in particular in South Africa (Department of Health) and Zimbabwe (Ministry of Health and Child Welfare)), or Asia (in particular Japan (Ministry of Health, Labour and Welfare), Taiwan (Executive Yuans Department of Health), and China (Ministry of Health People's Republic of China)).

When clopidogrel is present with another drug in an aqueous solution containing SAE-CD, there is a potential for competitive binding of the clopidogrel and other drug with SAE-CD. The extent to which competitive binding might occur can be predicted to some degree by comparison of the binding constant of clopidogrel versus that of the other drug. The greater a binding constant of a drug for a particular cyclodextrin, the more tightly bound the drug is to the cyclodextrin and the greater the amount of drug that can be solubilized by the cyclodextrin derivative. If the other drug has a much greater binding constant for SAE-CD than does clopidogrel, then the other drug will likely competitively bind SAE-CD. If the other drug has a much smaller binding constant for SAE-CD than does clopidogrel, then the other drug will likely not competitively bind SAE-CD.

If the binding constant of the other drug for SAE-CD approximates that of clopidogrel for SAE-CD, then the extent to which competitive binding occurs will be driven more by the relative molar ratio of the two drugs than by the binding constant of the two drugs. In other words, if the other drug is administered at a substantially higher molar concentration than is clopidogrel, then it will more competitively bind SAE-CD than if the other drug was administered at a substantially lower molar concentration than clopidogrel.

Figure 7:
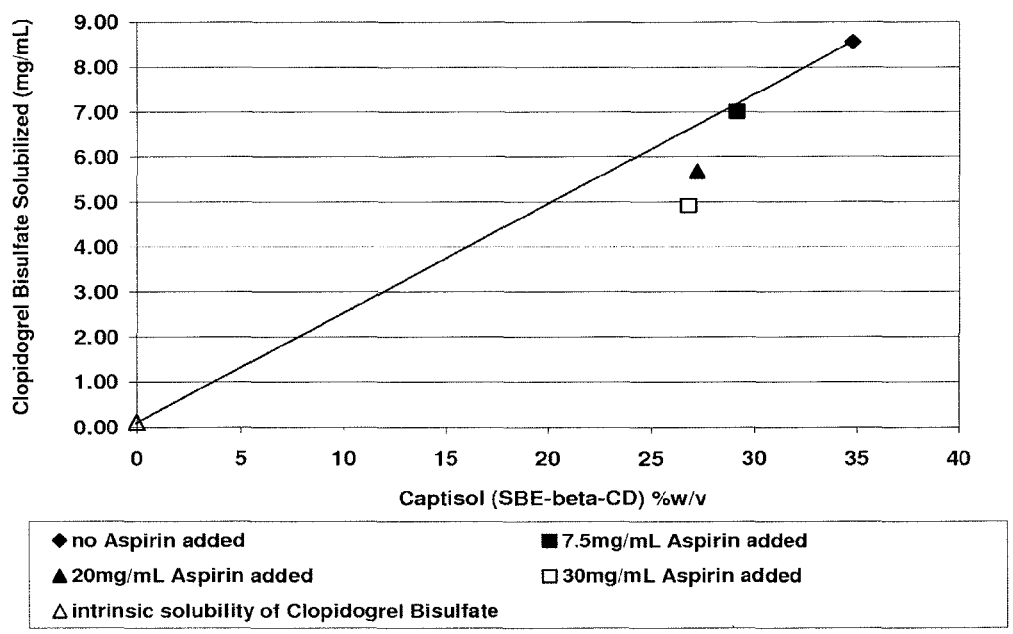
FIG. 7 depicts the results of a competitive binding assay between SAE-CD and clopidogrel salt in the presence of aspirin conducted according to Example 22

Exemplary formulations comprising SAE-CD, clopidogrel bisulfate, aqueous buffer, and aspirin were prepared according to Example 22. In this example, excess clopidogrel bisulfate was added to solutions containing fixed amounts of SAE-CD and varying amounts of aspirin. FIG. 7 depicts the results of a competitive binding study. The results indicate that aspirin binds competitively with SAE-CD when placed in a solution containing SAE-CD and clopidogrel salt. Thus, in a formulation containing both clopidogrel and aspirin, the formulation may or may not require additional SAE-CD to solubilize both ingredients than would be required to solubilize either component individually.

Although not necessary, the formulation of the present invention may include a antioxidant, acidifying agent, alkalizing agent, buffering agent, bulking agent, cryoprotectant, density modifier, electrolyte, flavors, fragrance, glucose, stabilizer, plasticizer, solubility-enhancing agent, sweeteners, surface tension modifier, volatility modifier, viscosity modifier, other excipients known by those of ordinary skill in the art for use in pharmaceutical formulations, or a combination thereof.

A complexation-enhancing agent can be added to the aqueous liquid formulation of the invention. A complexation-enhancing agent is a compound, or compounds, that enhance(s) the complexation of clopidogrel with the SAE-CD. When the complexation-enhancing agent is present, the required ratio of SAE-CD to clopidogrel may need to be changed such that less SAE-CD is required. Suitable complexation enhancing agents include one or more pharmacologically inert water soluble polymers, hydroxy acids, and other organic compounds typically used in liquid formulations to enhance the complexation of a particular agent with cyclodextrins. Suitable water soluble polymers include water soluble natural polymers, water soluble semisynthetic polymers (such as the water soluble derivatives of cellulose) and water soluble synthetic polymers. The natural polymers include polysaccharides such as inulin, pectins, algin derivatives and agar, and polypeptides such as casein and gelatin. The semi-synthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose, hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Suitable hydroxy acids include by way of example, and without limitation, citric acid, malic acid, lactic acid, and tartaric acid and others known to those of ordinary skill in the art.

Hydrophilic polymers can be used to improve the performance of formulations containing a cyclodextrin. Loftsson has disclosed a number of polymers suitable for combined use with a cyclodextrin (underivatized or derivatized) to enhance the performance and/or properties of the cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, Mich., United States, May 21-24, 2000 (2000), 10-15 (Wacker Biochem Corp.: Adrian, Mich.); PCT International Publication No. WO 9942111; Pharmazie, (1998), 53(11), 733-740; *Pharm. Technol. Eur*, (1997), 9(5), 26-34; *J. Pharm. Sci* (1996), 85(10), 1017-1025; European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Torres; Vila-Jato, J. L. Kluwer Academic Publishers, Dordrecht, Neth); *S.T.P. Pharma Sciences* (1999), 9(3), 237-242; ACS Symposium Series (1999), 737 (Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163(1-2), 115-121; Book of Abstracts, 216th ACS National Meeting, Boston, Aug. 23-27 (1998), CELL-016, American Chemical Society; *Journal of Controlled Release*, (1997), 44/1 (95-99); *Pharm. Res.* (1997), 14(11), 5203; *Investigative Ophthalmology & Visual Science*, (1996), 37(6), 1199-1203; Proceedings of the International Symposium on Controlled Release of Bioactive Materials (1996), 23rd, 453-454; *Drug Development and Industrial Pharmacy* (1996), 22(5), 401-405; Proceedings of the International Symposium on Cyclodextrins, 8th, Budapest, Mar. 31-Apr. 2, (1996), 373-376. (Editor(s): Szejtli, J.; Szente, L. Kluwer: Dordrecht, Neth.); *Pharmaceutical Sciences* (1996), 2(6), 277-279; European Journal of Pharmaceutical Sciences, (1996) 4(SUPPL.), S144; Third European Congress of Pharmaceutical Sciences Edinburgh, Scotland, UK Sep. 15-17, 1996; *Pharmazie*, (1996), 51(1), 39-42; *Eur. J. Pharm. Sci* (1996), 4(Suppl.), S143; U.S. Pat. Nos. 5,472,954 and 5,324,718; *International Journal of Pharmaceutics* (Netherlands), (Dec. 29, 1995) 126, 73-78; Abstracts of Papers of the American Chemical Society, (2 Apr. 1995) 209(1), 33-CELL; *European Journal of Pharmaceutical Sciences*, (1994) 2, 297-301; *Pharmaceutical Research* (New York), (1994) 11(10), S225; *International Journal of Pharmaceutics* (Netherlands), (Apr. 11, 1994) 104, 181-184; and *International Journal of Pharmaceutics* (1994), 110(2), 169-77, the entire disclosures of which are hereby incorporated by reference.

Other suitable polymers are well-known excipients commonly used in the field of pharmaceutical formulations and are included in, for example, *Remington's Pharmaceutical Sciences,* 18th Edition, Alfonso R. Gennaro (editor), Mack Publishing Company, Easton, Pa., 1990, pp. 291-294; Alfred Martin, James Swarbrick and Arthur Commarata, *Physical Pharmacy. Physical Chemical Principles in Pharmaceutical Sciences,* 3rd edition (Lea & Febinger, Philadelphia, Pa., 1983, pp. 592-638); A. T. Florence and D. Altwood, *(Physicochemical Principles of Pharmacy, 2nd Edition*, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

A solubility-enhancing agent can be added to the aqueous liquid formulation of the invention. A solubility-enhancing agent is a compound, or compounds, that enhance(s) the solubility of clopidogrel in the liquid formulation. When a complexation-enhancing agent is present, the ratio of SAE-CD to clopidogrel may need to be changed such that less SAE-CD is required. Suitable solubility enhancing agents include one or more organic solvents, detergents, soaps, surfactants and other organic compounds typically used in oral solution formulations to enhance the solubility of a particular agent. Suitable organic solvents include, for example, ethanol, glycerin, polyethylene glycols, propylene glycol, poloxomers, and others known to those of ordinary skill in the art.

Surfactants, which are considered solubility-enhancing agents, can be used to enhance solubilization of clopidogrel and reduce the amount of SAE-CD required to dissolve the clopidogrel. Exemplary formulations comprising SAE-CD, clopidogrel bisulfate, aqueous buffer, and surfactants were prepared according to Example 14. There was a marked increase in solubility of clopidogrel when using both polyethylene glycol-15-hydroxy stearate (Solutol®) and polysorbate 80 (Tween 80®). Other surfactants such as and not limited to; Cremophor®, polysorbate 20, 40, 60 and 80, Solutol®, Labrasol®, poloxamers, polyethylene glycol derivatives, cholate acids and their derivatives can be used and others known to individuals of ordinary skill in the art can also be used in combination with the SAE-CD. Exemplary solubility enhancing agents are disclosed in U.S. Pat. No. 6,451,339; however, other solubility enhancing agents used in the pharmaceutical industry can be used in the formulation of the invention.

The combined use of SAE-CD and surfactant may result in either a synergistic, additive or a negative effect on the solubility of the clopidogrel. The observed effect can be dependent upon the concentration of surfactant, in that using the same surfactant at different concentrations can produce different effects as is demonstrated in Example 14.

As shown in Tables 14a and 14b, Tween 80 shows an additive effect when used at concentrations of 1-2% (w/v) but a negative effect when used at 0.1, 0.5, 5 and 10% (w/v). Solutol (Tables 14c and 14d) shows a synergistic effect in the solubility at concentrations of between 1-5% (w/v). There is no change in the solubility at a concentration of 10% (w/v) of Solutol with and without CAPTISOL. Without being held bound to a particular mechanism, the negative solubility observed when surfactants are used with cyclodextrins may be due to the surfactant molecule acting as a competitive inhibitor in the solubilization of the drug by the complexant, in this case cyclodextrin. Similarly the complexant (the cyclodextrin) "pulls" the surfactant out of solution, making it unavailable for solubilizing the drug.

As used herein, the term "flavor" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and *cassia* oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available strawberry, orange, grape, cherry, vanilla, mint and citrus flavors and mixtures thereof. The amount of flavoring may depend on a number of factors, including the organoleptic effect desired. Flavors will be present in any amount as desired by those of ordinary skill in the art. Particularly flavors are the strawberry and cherry flavors and citrus flavors such as orange.

As used herein, the term "sweetener" is intended to mean a compound used to impart sweetness to a preparation. Such compounds include, by way of example and without limitation, aspartame, dextrose, glycerin, mannitol, saccharin sodium, sorbitol, xylitol, fructose, high fructose corn syrup, maltodextrin, sucralose, sucrose, other materials known to one of ordinary skill in the art, and combinations thereof.

As used herein, a fragrance is a relatively volatile substance or combination of substances that produces a detectable aroma, odor or scent. Exemplary fragrances include those generally accepted as FD&C.

As used herein, the term "alkalizing agent" is intended to mean a compound used to provide alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "antioxidant" is intended to mean an agent which inhibits oxidation and thus is used to prevent the deterioration of preparations by the oxidative process. Such compounds include by way of example and without limitation, acetone, sodium bisulfate, ascorbic acid, ascorbyl palmitate, citric acid, butylated hydroxyanisole, butylated hydroxytoluene, hydrophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, sodium metabisulfite, EDTA (edetate), pentetate and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, citric acid, maleic acid, monobasic sodium phosphate, dibasic sodium phosphate, lactic acid, tartaric acid, glycine, potassium metaphosphate, potassium phosphate, monobasic sodium acetate, sodium bicarbonate, sodium tartrate and sodium citrate anhydrous and dihydrate and others known to those of ordinary skill in the art.

As used herein, the term "stabilizer" is intended to mean a compound used to stabilize a therapeutic agent against physical, chemical, or biochemical process that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "viscosity modifier" is intended to mean a compound or combination of compounds capable of increasing or decreasing the viscosity of the liquid formulation. Some of the polymers disclosed herein can be used as viscosity modifiers.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

As used herein, the term "antifoaming agent" is intended to mean a compound or compounds that prevents or reduces the amount of foaming that forms on the surface of the liquid formulation. Suitable antifoaming agents include by way of example and without limitation, dimethicone, simethicone, octoxynol and others known to those of ordinary skill in the art.

As used herein, the term "bulking agent" is intended to mean a compound used to add bulk to the reconstitutable solid and/or assist in the control of the properties of the formulation during preparation. Such compounds include, by way of example and without limitation, dextran, trehalose, sucrose, polyvinylpyrrolidone, lactose, inositol, mannitol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

It should be understood, that compounds used in the pharmaceutical arts generally serve a variety of functions or purposes. Thus, if a compound named herein is mentioned only once or is used to define more than one term herein, its purpose or function should not be construed as being limited solely to that named purpose(s) or function(s).

The liquid formulation of the invention can be prepared by numerous different methods. According to one method, a first aqueous solution comprising SAE-CD is prepared. Then, a second solution comprising clopidogrel is prepared. Finally, the first and second solutions are mixed to form the liquid formulation. The first and second solutions can independently comprise other excipients and agents described herein. Additionally, the second solution can be water and/or an organic solvent-base solution. Another method of preparation is similar to the above-described method except that the clopidogrel is added directly to the first solution without the formation of a second solution. A third method of preparing the liquid formulation is similar to the above-described first method except that the SAE-CD is added directly to an aqueous second solution containing the clopidogrel without formation of the first solution. A fourth method of preparing the liquid formulation comprises the steps of adding an aqueous solution comprising clopidogrel to a powdered or particulate SAE-CD and mixing the solution until the SAE-CD has dissolved. A fifth method of preparing the liquid formation comprises the steps of adding the clopidogrel directly to the powdered or particulate SAE-CD and then adding an aqueous solution and mixing until the SAE-CD and clopidogrel has dissolved. A sixth method for preparing the liquid formation comprises the steps of heating either the first solution or heating the second solution, or heating a combination thereof of any solutions described in the above methods followed by the step of cooling the respectively heated solution. A seventh method for preparing the liquid formation comprises the step of adjusting the pH of either the first solution or adjusting the pH of the second solution or adjusting the pH of a combination of either solutions described in any of the above methods. An eighth method comprises the steps of creating the liquid formulation by any of the above-described methods followed by the step of isolating a solid material by lyophilization, drum drying, spray-drying, spray freeze-drying, vacuum-drying, antisolvent precipitation or a process utilizing a supercritical or near supercritical fluid. Any of the above solutions can contain other pharmaceutical excipients or ingredients as described herein.

Some embodiments of the method of preparing the liquid formulation further comprise the step(s) of: 1) filtering the formulation through a filtration medium wherein the pore size is about 5 µm or smaller; 2) sterilizing the liquid formulation by irradiation; 3) sterilizing the liquid formulation by treatment with ethylene oxide; 4) isolating a sterile powder from the sterilized liquid formulation; 5) purging the liquid with an inert gas to reduce the amount of dissolved oxygen in the liquid; and/or 6) one or more of the solutions used to prepare the liquid formulation is heated.

The invention provides pharmaceutical kits. In some embodiments, a pharmaceutical kit comprises a first chamber containing a liquid vehicle and a second chamber containing a reconstitutable solid pharmaceutical composition as described herein. The first and second chamber can be integral or engaged or assembled to form a container with at least two chambers, or the chambers can be separate to form separate containers. The liquid vehicle comprises an aqueous liquid carrier such as water, dextrose, saline, lactated Ringer's solution, or any other pharmaceutically acceptable aqueous liquid vehicles for the preparation of a liquid pharmaceutical compound. In some embodiments, the kit comprises a container comprising a reconstitutable solid pharmaceutical composition, and a container comprising a liquid carrier. In other embodiments, the kit comprises a container comprising at least two chambers, wherein a chamber comprises a reconstitutable solid pharmaceutical composition, and another chamber comprises a liquid carrier.

In some embodiments, the kit comprises a first chamber comprising a pharmaceutical composition comprising an SAE-CD, and a second chamber comprising a pharmaceutical composition comprising clopidogrel. The first and second chamber can be integral or engaged or assembled to form a container with at least two chambers, or the chambers can be separate to form separate containers. The first and second compositions can be mixed with a liquid carrier, which may or may not be included with the kit, and formulated as a liquid dosage form prior to administration to a subject. Either one or both of the first and second pharmaceutical compositions can comprise additional pharmaceutical excipients. The kit is available in various forms. In a first kit, the first and second pharmaceutical compositions are provided in separate containers or separate chambers of a container having two or more chambers. The first and second pharmaceutical compositions may be independently provided in either solid or powder or liquid form. For example, the SAE-CD can be provided in a reconstitutable powder form and clopidogrel can be provided in powdered form. According to one embodiment, the kit would further comprise a pharmaceutically acceptable liquid carrier used to suspend and dissolve the first and/or second pharmaceutical compositions. Alternatively, a liquid carrier is independently included with the first and/or second pharmaceutical composition. The liquid carrier, however, can also be provided in a container or chamber separate from the first and second pharmaceutical compositions. As above, the first pharmaceutical composition, the second pharmaceutical composition and the liquid carrier can independently comprise a preservative, an antioxidant, a buffering agent, an acidifying agent, an electrolyte, another therapeutic agent, an alkalizing agent, an antimicrobial agent, an antifungal agent, a solubility enhancing agent, a viscosity modifying agent, a flavoring agent, a sweetening agent or a combination thereof.

Some embodiments of the kit include those wherein: 1) the first and second pharmaceutical compositions are contained in separate containers or separate chambers of a container having two or more chambers; 2) the kit further comprises a separate pharmaceutically acceptable liquid carrier; 3) a liquid carrier is independently included upon each occurrence with the first and/or second pharmaceutical composition; 4) containers for the pharmaceutical compositions are independently selected at each occurrence from an evacuated container, bag, pouch, vial, bottle, or any pharmaceutically acceptable device known to those skilled in the art for the delivery of liquid formulations; 5) the first pharmaceutical composition and/or second pharmaceutical composition and/or liquid carrier further comprises an antioxidant, a buffering agent, an acidifying agent, a solubilizing agent or solubility enhancing agent, a complexation enhancing agent, lyophilizing aids (for example, bulking agents or stabilizing agents), an electrolyte, another therapeutic agent, an alkalizing agent, an antimicrobial agent, an antifungal agent, a viscosity modifying agent, a flavoring agent, a sweetening agent or a combination thereof; 6) the kit is provided chilled; 8) the liquid carrier and/or chamber has been purged with a pharmaceutically acceptable inert gas to remove substantially all of the oxygen dissolved in the liquid carrier; 9) the chambers are substantially free from oxygen; 10) the liquid carrier further comprises a buffering agent capable of maintaining a pH of about 2-7; 11) the chambers and solutions are sterile.

The term "unit dosage form" is used herein to mean a single dosage form containing a quantity of the active ingredient and the diluent or carrier, said quantity being such that one or more predetermined units are normally required for a single therapeutic administration. In the case of multi-dose forms, such as liquid-filled bottles, said predetermined unit will be one fraction such as a half or quarter of the multiple dose form. It will be understood that the specific dose level for any patient will depend upon a variety of factors including the indication being treated, therapeutic agent employed, the activity of therapeutic agent, severity of the indication, patient health, age, sex, weight, diet, and pharmacological response, the specific dosage form employed and other such factors.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" is taken to mean warm blooded animals such as mammals, for example, cats, dogs, mice, guinea pigs, horses, bovine cows, sheep, non-humans, and humans.

The liquid formulation of the invention will comprise an effective amount of clopidogrel. By the term "effective amount", it is understood that a therapeutically effective amount is contemplated. A therapeutically effective amount is the amount or quantity of clopidogrel that is sufficient to elicit the required or desired therapeutic response, or in other words, the amount that is sufficient to elicit an appreciable biological response when administered to a subject.

The invention also provides a pharmaceutical solid dosage form comprising a therapeutically effective amount of clopidogrel, sulfoalkyl ether cyclodextrin (e.g. SBE7-β-CD), and a pharmaceutically acceptable solid carrier, wherein the molar ratio of SAE-CD to clopidogrel is as defined herein. The SAE-CD and clopidogrel can be included in the dosage form in admixture, as a preformed complex, or a combination thereof. A solid dosage form can be prepared using conventional methods in the pharmaceutical sciences. In admixture, solid SAE-CD and solid clopidogrel are physically mixed using a low energy mixer to minimize complex formation. A solid preformed complex can be made by mixing SAE-CD and clopidogrel in a liquid carrier, such as an aqueous liquid carrier, to form the complex, followed by removal of the liquid carrier thereby forming the solid preformed complex. Alternatively, the complex can be prepared using a high energy milling process with the SAE-CD and clopidogrel, wherein either one or both of the two components is independently provided in solid or liquid form.

The molar ratio of SAE-CD to clopidogrel in a composition or formulation of the invention will vary according to the pH of the formulation or the pH of an intended environment of use for a formulation. For example, the molar ratio can be less than about 6:1 when the pH of the formulation or of the intended environment of use is less than about 3.5. Alternatively, the molar ratio of SAE-CD to clopidogrel can be in the range of at least about 6:1, about 6:1 to 8:1, or at least about 8:1 when the pH of the formulation or the intended environment of use is about or greater than about 3.5. When the pH of the formulation or intended environment of use is about 5.5 or about 5.5 to 8, the molar ratio can be at least about 6.5:1, or at least 6.6:1. When the pH of the formulation or intended environment of use is about 8, the molar ratio can be at least about 7.25:1, or at least 7.3:1.

The intended environment of use can be a pharmaceutical formulation or part of a subject, such as part of a subject's circulatory system or digestive tract, to which the formulation is administered. If the intended environment of use is the gastric region (meaning that the SAE-CD and clopidogrel is delivered to and released in the gastric region such as the stomach or duodenum), then a molar ratio of less than 6:1 or less than 3:1 can be used. If the intended environment of use is immediately downstream of the gastric region (meaning that the SAE-CD and clopidogrel is delivered to and released in the jejunum or ileum), then a molar ratio of at least 6:1 or at least 8:1 can be used.

For oral administration and gastric delivery and release, the molar ratio of SAE-CD, e.g. SBE7-β-CD, to clopidogrel can be reduced further to about 4:1 or less as is described in Examples 16 and 18 or to about 0.5:1 or less as in Example 23 because either: 1) the pH of the GI tract affects an increase in intrinsic solubility of the clopidogrel, thereby requiring a lower molar ratio of SAE-CD to clopidogrel for dissolution of the drug; or 2) the pH of the formulation can be at least mildly acidic. The pH of the exemplary reconstitutable formulations in Examples 16 and 18 ranges from pH 1-2.

In order for a liquid formulation of the invention to be clear, the molar ratio of SAE-CD to clopidogrel may vary according to the pH of the formulation. At a pH of about 8, the molar ratio should be at least about 7.25:1 or at least about 7.3:1, and at a pH of about 5.5, the molar ratio should be at least about 6.5:1 or at least about 6.6:1. This molar ratio is sufficient to provide a clear solution; however, higher molar ratios will result in improved stability against hydrolysis, photolysis, and chiral inversion by increasing the percentage of clopidogrel bound by SAE-CD.

The SAE-CD to clopidogrel molar ratio formulations prepared according to the examples below was determined. The pH of the liquid formulations was also determined. The data is summarized below.

| Example No. | pH of solution | Approx. Molar Ratio |
| --- | --- | --- |
| 2 and 3 | ~5.5 | 36:1 |
| 4 and 5 | ~8.0 | 36.1 |
| 10, 11, 12 and 13 | ~5.5 | 9:1 |
| 15 and 17 | ~1.8 | 10:1 |
| 16 and 18 | ~1.5 and ~1.8 | 5:1 |
| 19 | ~5.5 | 33:1 |
| 20 | ~5.5 | 16:1 |
| 23 | tablet | 1:1 |
| 24 and 25 | ~5.5 | 10:1 |

There is no need to provide an upper limit to the molar ratio of SAE-CD to clopidogrel, since excess SAE-CD present will only serve to stabilize the clopidogrel further. However, the invention includes embodiments wherein the upper limit of the molar ratio of SAE-CD to clopidogrel is less than 1000:1, less than or about 500:1, less than or about 250:1, less than or about 100:1, less than or about 75:1, less than or about 50:1, less than or about 40:1, less than or about 30:1, less than or about 20:1, less than or about 17.5:1, less than or about 15:1, less than or about 12.5:1, less than or about 10:1. These upper limits can be used in combination with the other lower limits set forth herein.

The molar ratio of SAE-CD to clopidogrel for a composition or method of the invention can be within the range of 6:1 and 8:1, 6:1 to 10:1, 5:1 to 12:1, 4:1 to 15:1, 5:1 to 14:1, 6:1 to 13:1, or 6:1 to 12.5:1; and/or at least 0.05:1, at least 0.25:1, at least 0.2:1, at least 0.5:1, at least 1:1, at least 2:1, at least 3:1, at least 4:1, at least 5:1, at least 6:1, at least 7:1, or at least 8:1; and/or at most 100:1, at most 75:1, at most 50:1, at most 40:1, at most 35:1, at most 30:1, at most 25:1, at most 20:1, at most 15:1, at most 14:1 at most 12.5:1, at most 12:1, at most 10:1, at most 8:1, at most 6:1, at most 5:1, at most 4:1, at most 3:1, or at most 2:1.

Tablets prepared according to Example 23 were subject to dissolution in one liter of citric acid/phosphate buffer. PLAVIX® tablets were used as control/reference samples. Each tablet contained 75 mg free base equivalents of clopidogrel.

Figure 9:
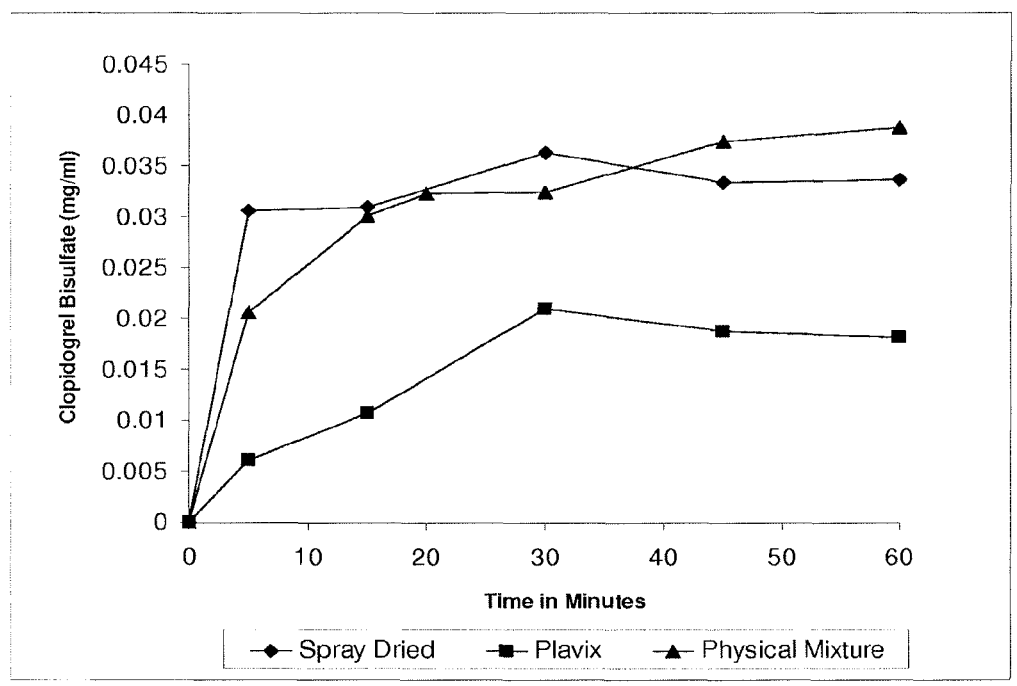
FIG. 9 depicts the results of the dissolution study of tablets made from a spray dried solid comprising SBE-β-CD and clopidogrel bisulfate solution, wherein the weight ratio of SBE-β-CD to clopidogrel bisulfate is 250 mg to 98 mg, respectively, or made from a physical mixture of SBE-β-CD and clopidogrel bisulfate using the same ratio. These were compared to the marketed tablet PLAVIX®. The evaluation was conducted according to Example 23.

As can be seen in FIG. 9, both the preformed complex and physical mixture based tablets containing SAE-CD have a faster dissolution rate than the PLAVIX® tablets, and they also have a higher final concentration. This faster dissolution time may lead to a faster absorption and hence faster/quicker therapeutic onset.

The typical oral daily dose for clopidogrel, expressed as the free base, is 75 mg. As a loading dose for certain minimally invasive interventional procedures, such as stent placement, angioplasty, intravascular ultrasound, atherectomy, carotid artery balloon angioplasty and stenting (CBAS), laser thrombolysis, brachytherapy, ultrasonography, use of intraarterial suction devices, use of snares, or use of clot-retrieval devices, higher doses can be administered, e.g. 900 mg, 750 mg, 675 mg, 600 mg, 450 mg, 375 mg, 300 mg, 225 mg, 200 mg, 150 mg, 100 mg, 75 mg, 50 mg, 40 mg, 30 mg, 25 mg, 20 mg, 15 mg, 12.5 mg, 10 mg, 7.5 mg, 5 mg, 2 mg, 1 mg, 0.75 mg, or 0.1 mg of clopidogrel, or in the range of 0.1 to 900 mg, 0.1 to 100 mg, 100 to 300 mg, about 300 mg, 300 to 600 mg, 300 to 900 mg, 600 to 900 mg, 50 to 600 mg, 75 to 600 mg, 150 to 600 mg, or 200 to 450 mg of clopidogrel. Although titration of the dose is not indicated for PLAVIX®, the present formulation is easily divisible to facilitate careful dose titration if needed. The present formulations can be administered as directed in the package insert for the PLAVIX® tablet formulation, meaning a subject can be administered a dose of the present formulation containing an equivalent amount of clopidogrel, which would be about 75, about 300 or about 75 to about 300 mg. The Physician's Desk Reference $56^{th}$ ed. (pp. 3084-3086; Eds. Lori Murray, Gwynned L. Kelly; Medical Economics Company, Inc., Montvale, N.J. 07645-1742, 2002), the relevant text of which is hereby incorporated by reference, discloses the package insert for PLAVIX®, and particularly the dosage and administration for the formulation.

As used herein, the term "bleeding time" refers to the amount of time it takes for bleeding to stop in a mammal after controlled, standardized puncture of the skin of the mammal, for example, after controlled, standardized puncture of the earlobe or forearm of the mammal (or subject). Bleeding is stopped in part by platelet aggregation in vivo; therefore, bleeding time increases as the rate or overall amount of platelet aggregation decreases, and bleeding time decreases as the rate or overall amount of platelet aggregation increases. The relationship between bleeding time and platelet aggregation is not necessarily linear. Bleeding time is an indirect measure of the extent of or potential for platelet aggregation.

A bleeding time assay can be conducted according to standardized assays described in the literature (Sramek, et al, *Thrombosis and Haemostasis* 67 (5) 514-518 (1992)) or according to Example 21, wherein the bleeding time is measured after controlled, standardized puncture of the skin of a subject. A bleeding time assay measures the time it takes for a small blood vessel to close off and stop bleeding after it has been punctured.

The percentage increase in a subject's bleeding time is determined by first measuring the subject's "baseline bleeding time" (BBT, sec) prior to administration of a formulation or composition of the invention. The subject is then administered a formulation or composition of the invention, and the subject's "treatment bleeding time" (TBT, sec) is measured. The percentage increase ($\delta$BT, %) is then calculated as follows:

$$\delta BT = ((TBT-BBT)/BBT)*100$$

Known platelet aggregation assays and standard point-of-care equipment can be employed to determine the extent of or rate of (or potential for) platelet aggregation ex vivo. Most determinations are performed using either an optical-based method or an impedance-based method (Dyszkiewicz-Korpanty, et al., *Clinical and Applied Thrombosis/Hemostasis*, Vol. 11, 1, 25-35 (2005), the entire disclosure of which is hereby incorporated by reference). Exemplary equipment, systems and assays include a platelet aggregometer (Chronolog Corporation, Havertown, Pa.), VerifyNow Platelet Aggregometry (Accumetrics, San Diego, Calif.), Platelet Aggregation Profiler™ (Bio/Data Corporation, Horsham, Pa.) Slide Platelet Aggregation Test™ (SPAT™, Analytical Control Systems, Inc., Fishers, Ind.), Heparin Induced Platelet Aggregation test, Ristocetin Titration Platelet Aggregation assay, and others. The assay is generally based upon impedance or optical aggregometry. In general, a sample of a subject's blood is obtained and the plasma is separated from the sample. The plasma is treated with ADP, as described herein, and the extent of platelet aggregation in the plasma is then determined. The assay can be conducted before or after clopidogrel is administered to a subject.

The percentage decrease in a subject's extent of (or potential for) platelet aggregation is determined by first measuring the subject's "baseline platelet aggregation" (BPA) prior to administration of a formulation or composition of the invention. The subject is then administered a formulation or composition of the invention, and the subject's "treatment platelet aggregation" (TPA) is measured. The percentage decrease (EPA, %) is then calculated as follows:

$$\delta PA = ((BPA-TPA)/BPA)*100$$

Figure 8:
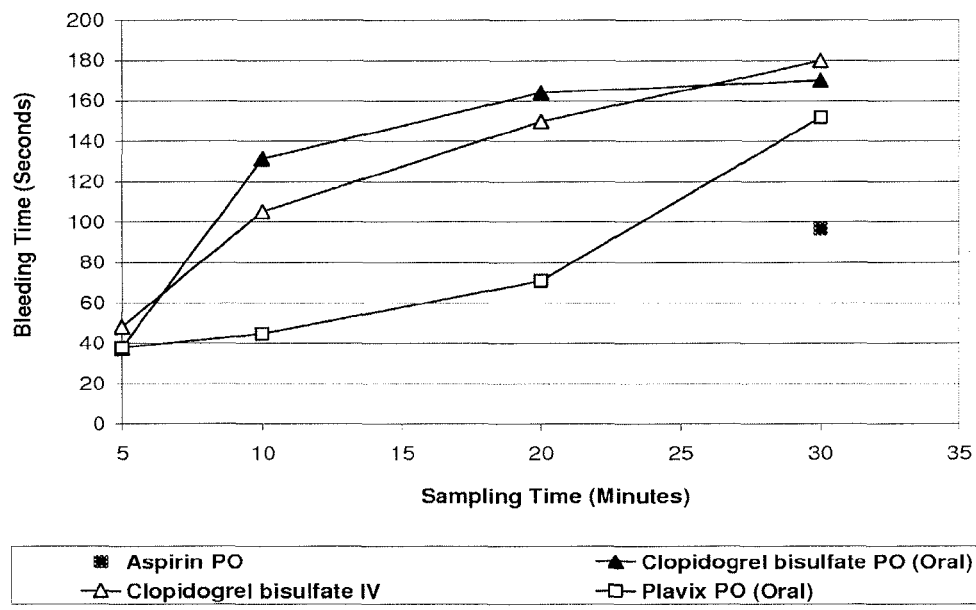
FIG. 8 depicts the results of an in vivo study to determine bleeding time in mice following administration (parenteral and peroral) of a clear liquid formulation prepared according to Example 20. The evaluation was conducted according to Example 21.

An in vivo evaluation in mice of a clear liquid formulation, prepared according to Example 20, was conducted according to Example 21. The bleeding time of the individual mice was measured periodically to determine the difference in performance between a PLAVIX® formulation (oral, ground tablet), clopidogrel bisulfate-SAE-CD (i.v.), clopidogrel bisulfate-SAE-CD (oral, solution). A reduction in the time to achieve an increased bleeding time is considered a reduction in the time to therapeutic onset, since an increase in bleeding time marks the beginning of therapeutic onset. The results (FIG. 8) indicate that use of a formulation according to the invention results in a more rapid therapeutic onset, whereby the amount of time after administration required to achieve a desired increase in bleeding time is substantially reduced as compared to administration of the PLAVIX® solid (administered as a powder prepared by crushing or grinding a tablet.) The formulation of the invention provides a more rapid therapeutic onset without requiring such excessive doses as are currently administered for interventional cardiology procedures.

Surprisingly, the oral dose of the invention can provide almost the same rate of therapeutic onset and level of therapeutic effect as does the parenteral i.v. dose of the invention, and both provide a substantially more rapid onset of therapeutic benefit and a higher level of therapeutic effect than does a reference formulation, for example an oral tablet, containing an equivalent dose of clopidogrel.

Related to the reduced time to therapeutic onset, the invention provides a reduced time to peak or target therapeutic effect. In some embodiments, the invention provides a method of decreasing the time to peak or target therapeutic effect in a responder subject administered clopidogrel, the method comprising: administering to a subject in need thereof a first composition comprising SAE-CD and a therapeutically effective amount of clopidogrel sufficient to achieve a target therapeutic effect, whereby the time to peak or target therapeutic effect achieved by administration of the first composition is less than the time to peak therapeutic effect achieved by similar administration of an otherwise similar reference composition, excluding SAE-CD, and comprising substantially the same therapeutically effective amount of clopidogrel. The reference composition can be a tablet. The first composition can be a solid, suspension or liquid.

Figure 10:
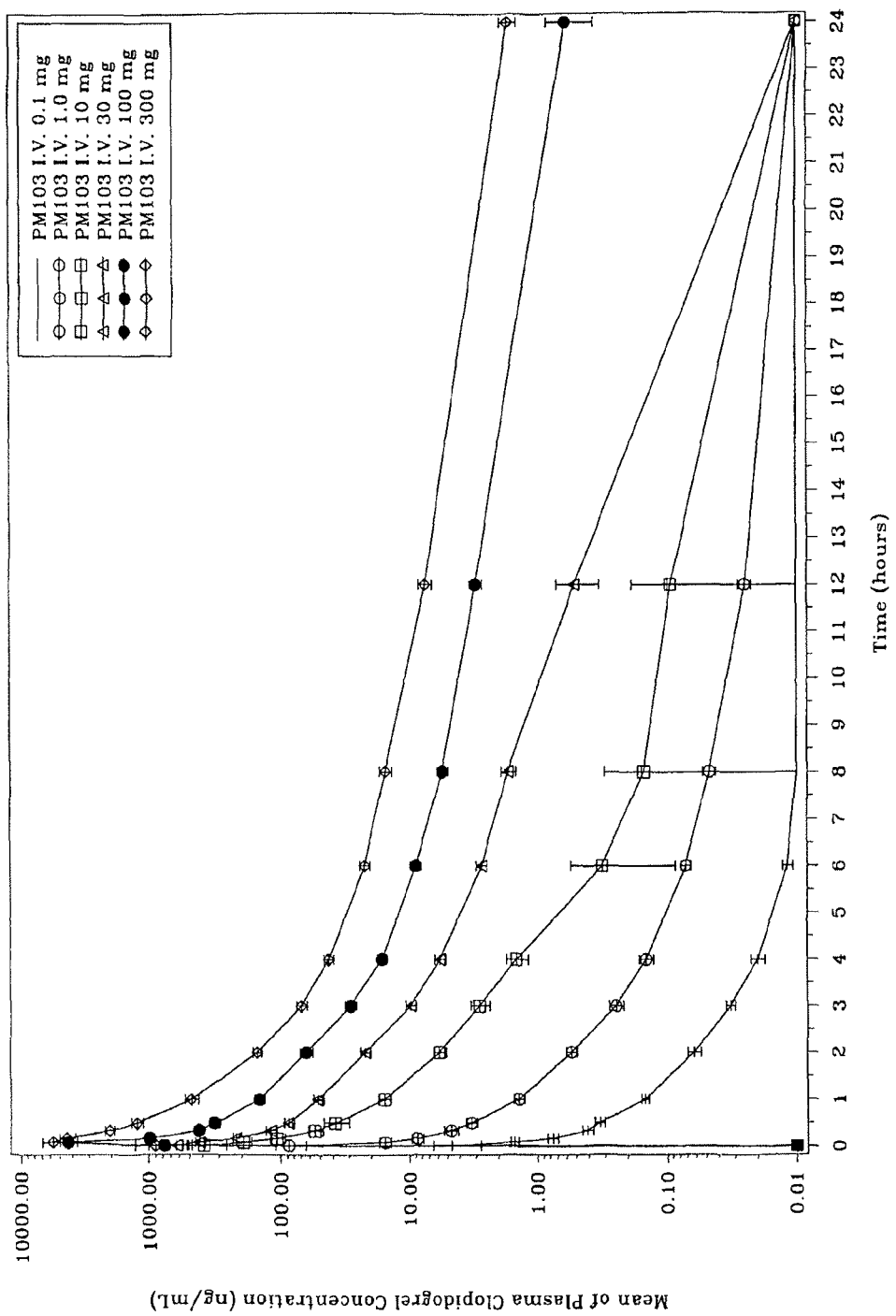
FIG. 10 a log-linear plot of mean plasma clopidogrel concentration versus time after IV administration in patient cohorts receiving 0.1 to 300 mg of clopidogrel in an aqueous liquid composition of the invention.
Figure 11:
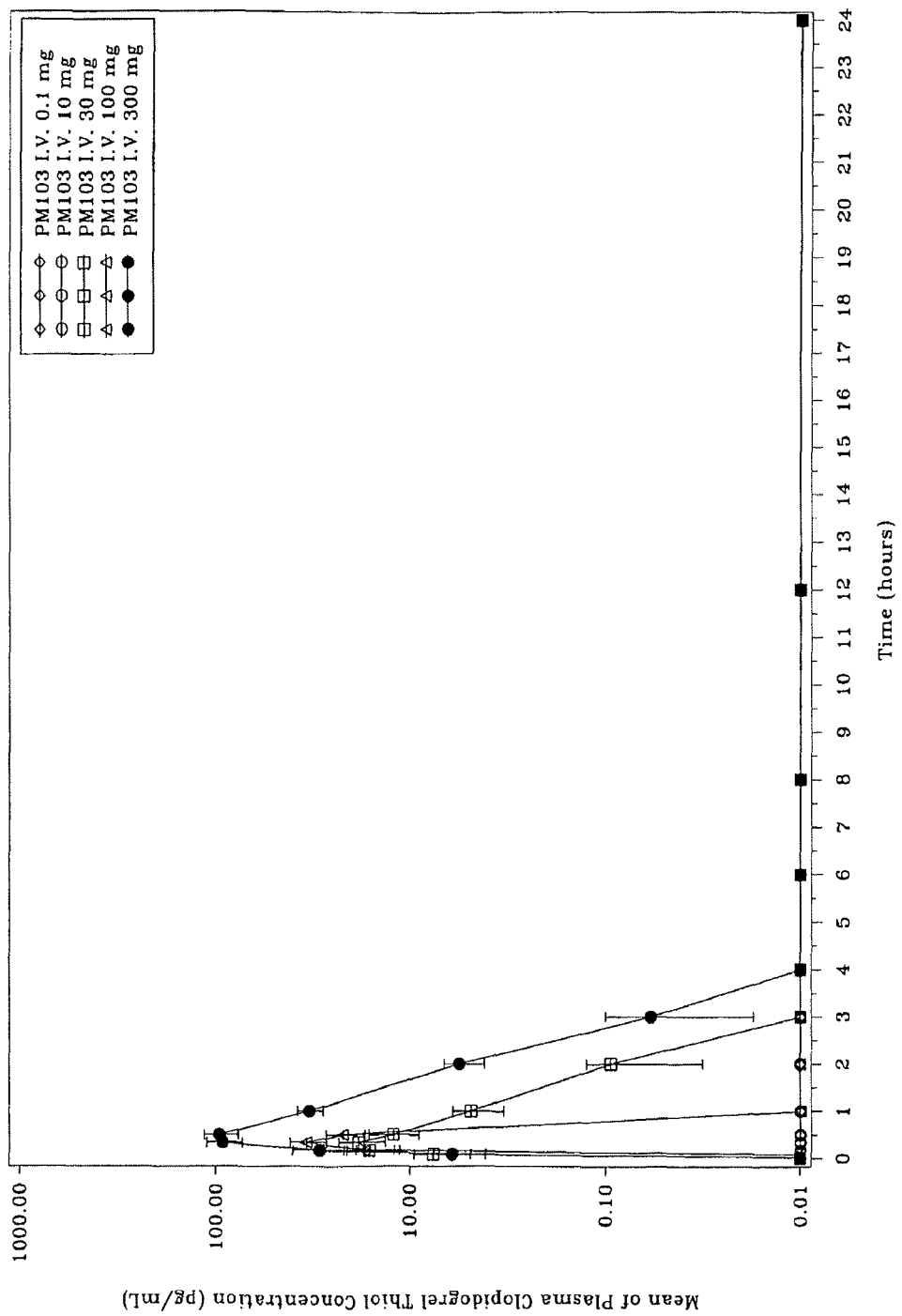
FIG. 11 a log-linear plot of mean plasma clopidogrel thiol active metabolite concentration versus time after administration for the patients of FIG. 10.
Figure 12:
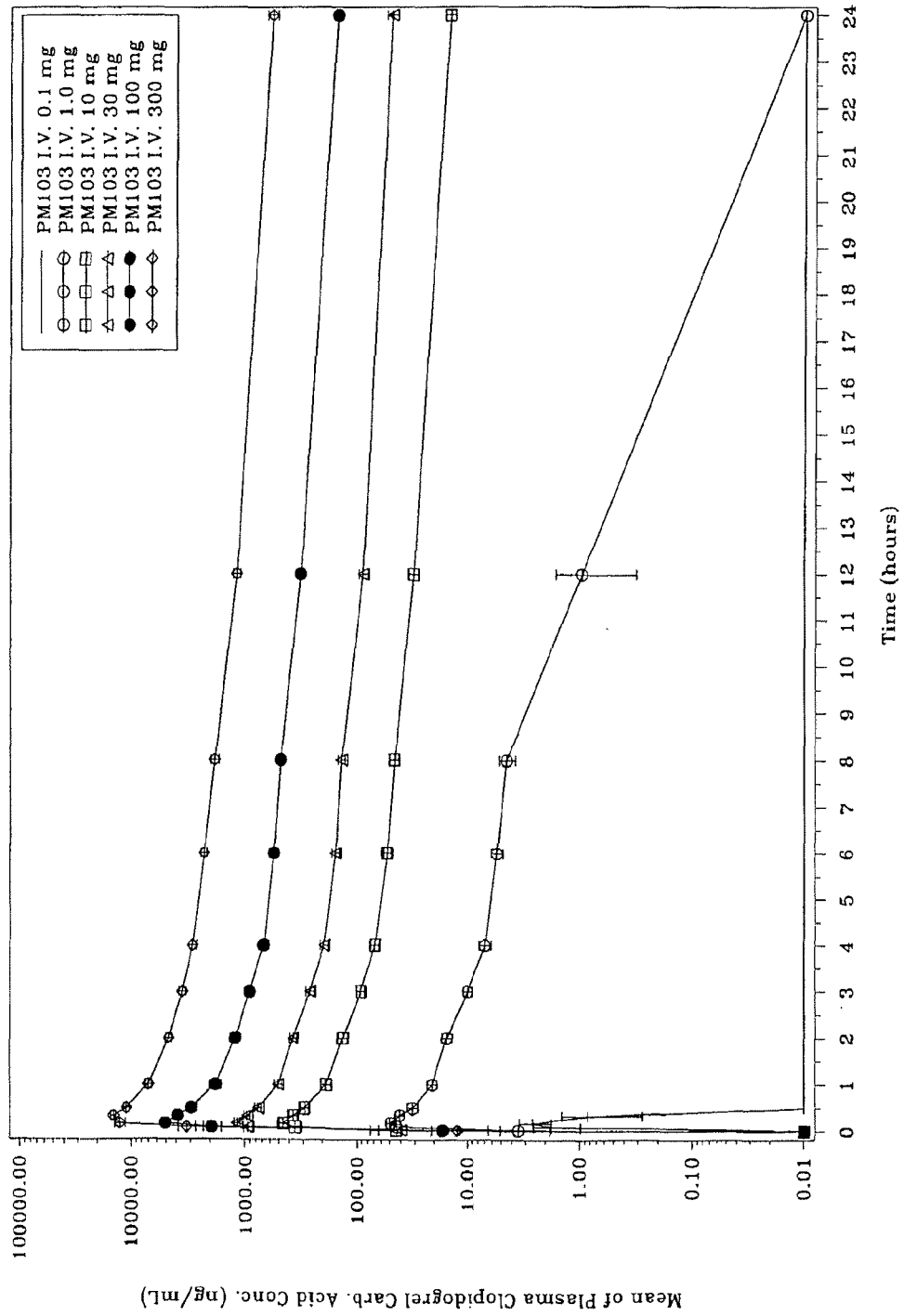
FIG. 12 a log-linear plot of mean plasma clopidogrel carboxylic acid metabolite concentration versus time after administration for the patients of FIG. 10.

FIGS. 10 to 12 are log-linear plots of mean plasma concentration of compound versus time after administration for the compounds clopidogrel (FIG. 10), the thiol metabolite of clopidogrel (FIG. 11) and the carboxylic acid metabolite of clopidogrel (FIG. 12). The data were obtained as part of the clinical study detailed in Example 27. FIG. 10 depicts a clear dose to plasma concentration relationship for clopidogrel administered parenterally, i.e. intravenously, for 0.1, 1.0, 10, 30, 100 and 300 mg doses. The higher the dose administered, the higher the plasma concentration of clopidogrel. The time to peak plasma concentration was about 30 sec or about 1-5 minutes, or less than or about 10-15 minutes, and greater than or about the end of the administration period or by termination of administration. The time to peak plasma concentration can be affected by the rate of parenteral administration: the longer the period of administration, the longer the time to peak plasma concentration. As noted below, the clopidogrel was administered i.v. over as a bolus over a period of less than or about 1 min (for samples comprising 0.1 mg, 1 mg, 10 mg, or 30 mg of clopidogrel), about 3 to 5 minutes or about 4 minutes (for samples comprising about 100 mg of clopidogrel), and about 6 to 10 min or about 8 minutes (for samples comprising about 300 mg of clopidogrel).

FIG. 11 depicts a dose to plasma concentration relationship for the thiol metabolite of clopidogrel. The data were obtained as part of the clinical study detailed in Example 27. In general, the higher the dose of clopidogrel, the higher the corresponding plasma concentration of the metabolite, which is thought to be the pharmacologically active metabolite. It is important to note that low doses of clopidogrel can provide a therapeutic response even though the corresponding plasma concentration of the thiol metabolite may be below its detection limit, at least according to the assay used herein. Accordingly, it is not necessary, for the methods of the invention, that the thiol metabolite be quantifiable or even detectable. It is only necessary that the amount of clopidogrel converted in vivo to the thiol metabolite is sufficient to provide a corresponding therapeutic effect in a subject within a specified period of time.

FIG. 12 depicts a dose to plasma concentration relationship for the carboxylic acid metabolite of clopidogrel. The data were obtained as part of the clinical study detailed in Example 27. In general, the higher the dose of clopidogrel, the higher the corresponding plasma concentration of the metabolite, which is thought to be a pharmacologically inactive metabolite.

Figure 13:
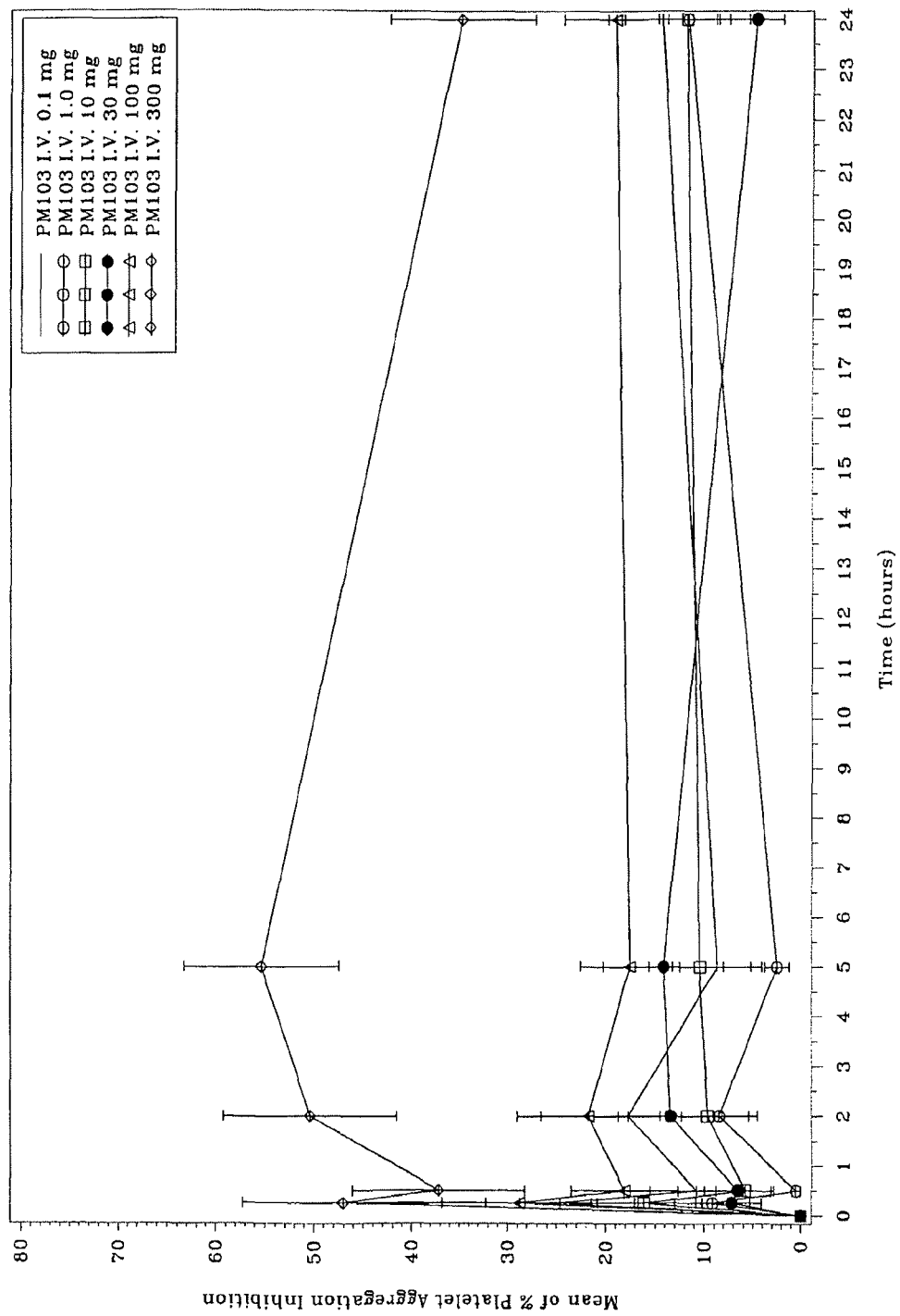
FIG. 13 is a plot of the mean percent of platelet aggregation inhibition versus time after IV administration in patient cohorts receiving 0.1 to 300 mg of clopidogrel in an aqueous liquid composition of the invention.

FIG. 13 depicts mean dose-response curves for the subjects administered clopidogrel according to Example 27. The response was determined as percent of platelet aggregation inhibition following exposure of the subjects' plasma ex-vivo to ADP (5 µM). In general, the time to onset of the therapeutic effect was less than or about 15 minutes. As described by Weerakody et al. 2007 (see previous citation), maximal platelet aggregation inhibition of >=15% is a recognized therapeutic effect to differentiate various anti-platelet drugs known to be useful in the treatment of ACS.

As a result of the more rapid therapeutic onset, more rapid time to peak plasma concentration, more rapid time to peak therapeutic effect, more rapid time to target therapeutic effect provided by the methods and compositions of the invention, several clinical advantages are provided by the same as compared to pharmaceutical oral tablet compositions of clopidogrel and administration and uses thereof. For instance, the compositions and methods of the invention provide reduced treatment time, reduced immediate risk of occurrence of a second cardiovascular event in a subject by reducing treatment/response time, such as by reducing the time to peak therapeutic, time to peak plasma concentration, time to target therapeutic effect, and time to therapeutic onset.

Figure 14:
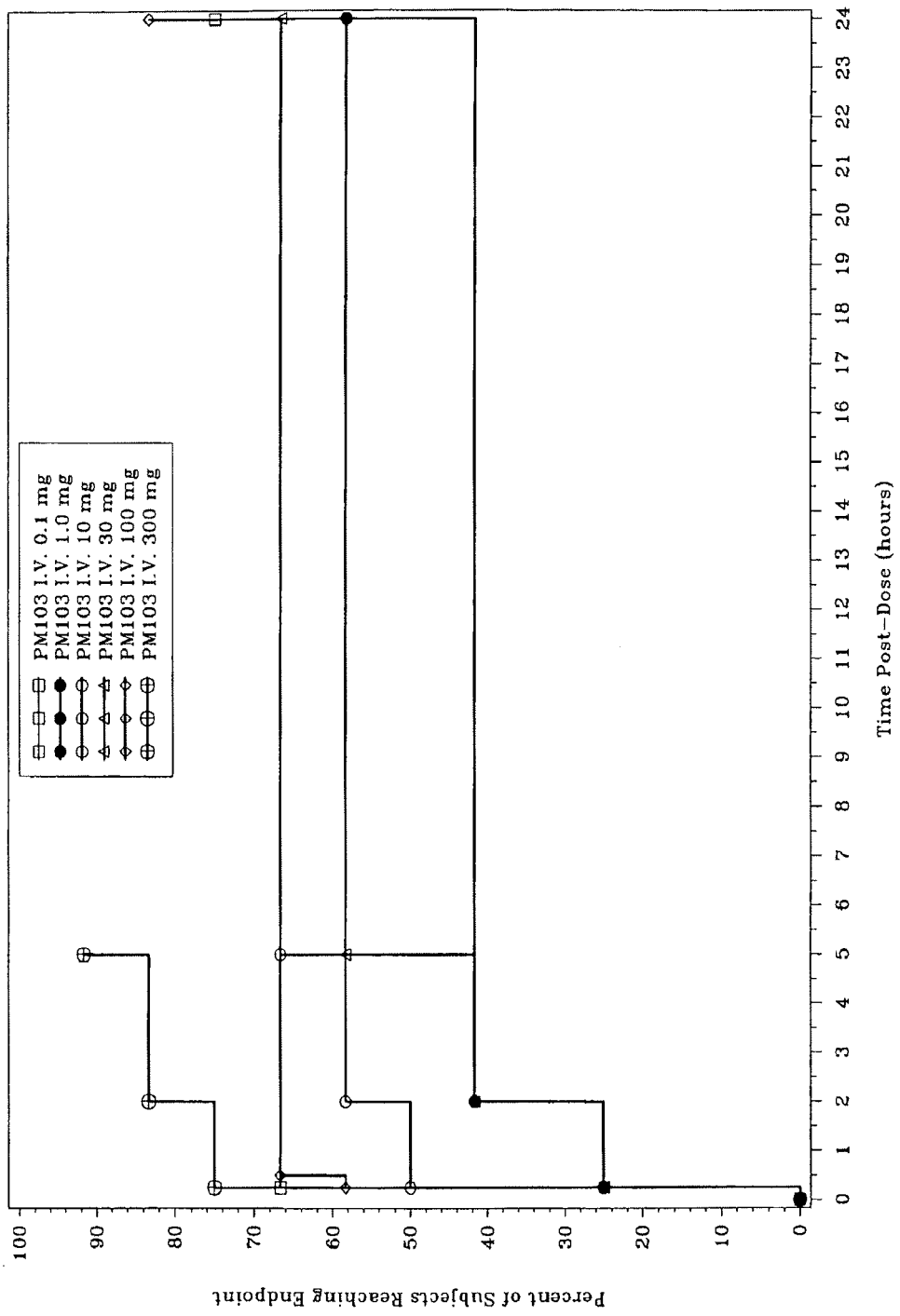
FIG. 14 is a Kaplan-Meier plot for estimates of percentage of patients achieving >/=15% platelet aggregation inhibition versus time after administration for the patients of FIG. 13.

FIG. 14 depicts a plot of the percentage of responder subjects versus the time period after administration of clopidogrel according to Example 27. As used herein a "responder" subject is a subject that has been treated with clopidogrel and whose plasma exhibits at least a 15% platelet aggregation inhibition when the subjects' plasma is exposed ex vivo to 5 µM ADP and the extent of platelet aggregation is determined by platelet aggregometry. Any known method of platelet aggregometry can be used according to the invention; however, suitable methods are described herein. In general, the higher the dose administered to a group of subjects, the higher the percentage of responder subjects identified in that group. As well, the higher the dose administered to a group of subjects, the more rapid the group reached its maximum number of responder subjects. A composition or formulation of the invention can be used to treat, prevent, ameliorate, reduce the occurrence of, or reduce the risk of occurrence of a disease, disorder or condition that is therapeutically responsive to clopidogrel therapy. As used herein as regards a method of treatment of a subject, the term "treat" or "treating" means to alleviate, ameliorate, eliminate, reduce the severity of, reduce the frequency of, occurrence of, or prevent symptoms associated with a disease, disorder or condition having excessive or undesired platelet aggregation as an etiological component. As used herein, the term "therapeutically responsive to clopidogrel" means that treatment of a subject with such a disease, disorder or condition with a therapeutically effective amount of clopidogrel will result in a clinical benefit or therapeutic benefit in the subject. The method of treating, preventing, ameliorating, reducing the occurrence of, or reducing the risk of occurrence of a disease, disorder or condition that is therapeutically responsive to clopidogrel therapy in a subject comprises administering to the subject in need thereof a formulation or composition of the invention, wherein the formulation or composition comprises SAE-CD and a dose of clopidogrel. A therapeutically effective amount of clopidogrel can include one, two, or more doses of clopidogrel.

In some embodiments, the disease, disorder or condition includes a thrombotic disease, disorder, or condition and can be selected from the group consisting of myocardial infarction, stroke, established peripheral arterial disease (PAD), secondary ischemic events, acute coronary syndrome (ACS, e.g. unstable angina/non-Q-wave MI), transient ischemic attack, cerebral arteriosclerosis, cerebrovascular disease, cardiovascular disease, angina pectoris, deep vein thrombosis, pulmonary emboli (PE), sickle cell crisis, and cardiac arrhythmia.

The compositions, methods, and formulations of the invention can be employed in both interventional and non-interventional treatment protocols for subjects presenting with a cardiovascular condition such as, ACS (Acute Coronary Syndrome), which refers to any group of clinical symptoms compatible with acute myocardial ischemia. Acute myocardial ischemia is chest pain due to insufficient blood supply to the heart muscle that results from coronary artery disease. They can be employed in medical treatment protocols requiring a minimally invasive interventional procedure such as PCI (stent replacement or balloon angioplasty) or in medical treatment protocols not requiring invasive procedures. In order to benefit from clopidogrel therapy, the subject would necessarily be a responder, as defined herein. The subject may or may not be undergoing chronic clopidogrel therapy prior to presenting with the ACS. In its broadest sense, the treatment protocol comprises administering to the subject in need thereof a pharmaceutical composition comprising SAE-CD and clopidogrel in an amount sufficient to provide a target therapeutic effect in the subject within a period of 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after administration of the composition.

In this regard, the target therapeutic effect is that level of platelet aggregation inhibition or bleed time as deemed sufficient by a clinician to permit performance of the minimally invasive interventional procedure, such as PCI. The target therapeutic effect may vary from subject to subject according to their ability to absorb and/or metabolize clopidogrel to its active metabolite. The therapeutic effect may vary according to the disease, disease, disorder or condition being treated; however, any and all clinically beneficial therapeutic effects achieved in a subject as a result of the in vivo inhibition of platelet aggregation or increased bleeding time caused by clopidogrel, when administered to the subject in the compositions and/or according to the methods of the invention, are contemplated.

The treatment protocol can further comprise the earlier step of determining whether or not the subject requires interventional or non-interventional medical treatment. Following administration of the clopidogrel, the subject may undergo the minimally invasive procedure in as little as 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after parenteral or peroral administration of the clopidogrel-containing composition of the invention.

For a treatment protocol wherein a non-interventional procedure (medical treatment) and clopidogrel administration are indicated for the subject, the subject will be administered clopidogrel in a composition of the invention and a second therapeutic agent, such as described herein.

In some embodiments, the invention provides a treatment protocol for a subject presenting with a cardiovascular condition, disease or disorder, the method comprising: a) determining whether or not the subject requires interventional or non-interventional medical treatment; and b) if the subject requires minimally invasive interventional medical treatment, then administering to the subject a pharmaceutical composition comprising SAE-CD and clopidogrel in an amount sufficient to provide a target therapeutic effect in the patient within a period of 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after said administration, and conducting the minimally invasive interventional procedure; or c) if the subject requires non-interventional medical treatment, then administering to the subject a pharmaceutical composition comprising SAE-CD and clopidogrel in an amount sufficient to provide a target therapeutic effect in the subject within a period of 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min and providing to the subject said non-interventional medical treatment; or d) if the subject requires invasive interventional medical treatment (e.g. CABG), then not administering to the subject clopidogrel. In some embodiments, the protocol comprises: 1) optionally sedating patient presenting; 2) determining for high risk of ACS; 3) optionally, alerting the catheter lab of incoming patient; 4) optionally, transporting patient to the catheter lab; 5) performing one or more diagnostic coronary tests on the patient; 6) determining if PCI or CABG is indicated; and 7) if PCI is indicated, parenterally administering a liquid composition or formulation comprising clopidogrel, and optionally SAE-CD, or perorally administering a composition or formulation comprising clopidogrel and SAE-CD, performing PCI, and optionally maintaining the patient on long term (chronic) clopidogrel therapy; or 8) if CABG is indicated, performing the CABG, without administration of clopidogrel. The method of the invention can include additional steps as needed, such as any step(s) indicated by an attending clinician. The method of sedating can include administration of an anxiolytic agent, NSAID, non-narcotic pain relieving agent, narcotic pain relieving agent, anesthetic, sedative, and/or anti-inflammatory agent.

Suitable diagnostic coronary tests include coronary angiography, electrocardiography, EKG, echocardiography, CT scanning angiography and any other test knows to those of skill in the art for determining coronary dysfunction the result of which might require an interventional or non-interventional treatment.

A non-interventional procedure is defined as a non-surgical procedure. A non-interventional procedure can be administration of one or more other therapeutic agents to the subject or another non-surgical procedure as described herein. An interventional procedure is defined as an invasive or minimally invasive surgical procedure. An invasive procedure can be CABG. A minimally invasive procedure can be PCI.

Given that clopidogrel therapy will only be useful to a responder subject, the invention provides a method of rapidly determining whether a subject is a responder or a non-responder. The method comprises: administering to the subject a composition comprising an "expected therapeutically effective amount" of clopidogrel, and determining the subject's responsiveness to the clopidogrel within a period of 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after administration of the composition to the subject. By "expected therapeutically effective amount" is meant that amount of clopidogrel that would be expected to provide a therapeutic effect in the subject at the time the subject is administered the composition. An expected therapeutically effective amount is generally 900 mg, 750 mg, 675 mg, 600 mg, 450 mg, 375 mg, 300 mg, 225 mg, 200 mg, 150 mg, 100 mg, 75 mg, 50 mg, 40 mg, 30 mg, 25 mg, 20 mg, 15 mg, 12.5 mg, 10 mg, 7.5 mg, 5 mg, 2 mg, 1 mg, 0.75 mg, or 0.1 mg of clopidogrel, or in the range of 0.1 to 900 mg, 0.1 to 100 mg, 100 to 300 mg, about 300 mg, 300 to 600 mg, 300 to 900 mg, 600 to 900 mg, 50 to 600 mg, 75 to 600 mg, 150 to 600 mg, or 200 to 450 mg of clopidogrel.

According to the method, a responder subject is one that exhibits >1=15% inhibition of platelet aggregation, as determined with an ex vivo assay, following administration of an expected therapeutically effective amount of a composition or formulation of the invention. A non-responder (otherwise known as a poor responder, hypo-responder, intermediate responder, low responder or resistant) subject is one in which <15% inhibition of platelet aggregation, as determined with an ex vivo assay, following administration of an expected therapeutically effective amount of a composition or formulation of the invention. Platelet aggregation inhibition is defined as the % of platelet aggregation induced by 5 uM adenosine diphosphate (ADP) in an ex vivo assay. Suitable methods for use in defining a subject as a responder versus as non-responder are disclosed by Weerakkody et al. (*J. Cardiovascular Pharmacol. Therap.* (2007), 12(3), 205-212), the entire disclosure of which is hereby incorporated by reference.

The method of the invention is advantageously conducted in a shorter time period than can be achieved by an otherwise similar method where the clopidogrel is administered as a solid oral tablet. In other words, parenteral or peroral administration to a subject of clopidogrel in a composition or formulation of the invention will provide a faster onset of a therapeutic response in a responder subject than does peroral administration of a solid oral dosage form, e.g. PLAVIX®, tablet(s), not of the invention but comprising substantially the same amount of clopidogrel. This means the time period, within which a clinician is able to determine whether or not a subject is a responder, will be shorter when the subject is administered a composition of the invention than when the subject is orally administered a solid dosage form not of the invention, e.g. PLAVIX®. The time period for such determination according to the invention is generally in the range of 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after administration of the composition.

The step of determining the subject's responsiveness to clopidogrel can comprise: obtaining a sample of blood of the subject; and determining the extent of platelet aggregation in the subject's plasma. Suitable methods for determining the extent of platelet aggregation in the subject's plasma include, by way of example and without limitation, aggregometry, such as light transmittance or impedance aggregometry.

The composition and formulation of the invention provides one or more advantages over peroral administration of clopidogrel-containing tablets, e.g. PLAVIX®. One such advantage is dose reduction. A subject being perorally or parenterally administered a dose of clopidogrel in a composition or formulation of the invention will require a first therapeutically effective amount in order to receive a therapeutic benefit from the clopidogrel. The same subject being perorally administered a dose of clopidogrel in a tablet dosage form, not according to the invention, will require a second therapeutically effective amount in order to receive substantially the same therapeutic benefit from the clopidogrel. For that subject the first therapeutically effective amount can be and is generally less than the second therapeutically effective amount. Accordingly, a method of reducing the required therapeutic dose in a responder subject in need of clopidogrel therapy, the method comprising: parenterally or perorally administering to the subject a first therapeutically effective amount of clopidogrel in a pharmaceutical composition comprising SAE-CD, wherein the first therapeutically effective amount is at least 1.1-fold, at least 1.2-fold, at least 1.25-fold, at least 1.5-fold, at least 2-fold, at least 3-fold, at least 4-fold, at least 5-fold, at least 7-fold, at least 8-fold, at least 10-fold smaller, at least 15-fold, at least 20-fold, about 1.1 to about 20-fold, about 1.2-fold to about 15-fold, about 1.25-fold to about 10-fold, about 2-fold to about 10-fold, or about 3 fold to about 8-fold smaller than a second therapeutically effective amount, which is the amount of clopidogrel required to provide substantially the same therapeutic effect when clopidogrel is administered to the subject perorally in a reference solid pharmaceutical composition excluding SAE-CD.

The parenteral administration of clopidogrel to a subject in need thereof according to the invention may provide an alternative means of therapy for a subject that is a non-responder in terms of peroral administration of clopidogrel. For example, it may occur that a subject being perorally administered a tablet comprising clopidogrel (such as a PLAVIX tablet) will not exhibit a sufficiently high therapeutic response to be deemed a "responder", as defined herein. However, that same subject may become a responder by being administered the clopidogrel parenterally. In one clinical study, a group of subjects were administered clopidogrel (10-300 mg) perorally, and those subjects did not exhibit a sufficiently high therapeutic response to be deemed "responders". Clopidogrel was then administered parenterally to those same subjects, after which 9-25% of the subjects exhibited a sufficiently high therapeutic response to be deemed "responders". Accordingly, the invention provides a method of converting a non-responder subject, in terms of peroral administration of clopidogrel, to a responder subject, the method comprising parenterally administering clopidogrel to the subject in need thereof, thereby providing a therapeutic response to clopidogrel in the subject, wherein the therapeutic response is sufficient to deem the subject a responder.

Another such advantage is the ability of a clinician to titrate the dose administered to a subject within a shorter period of time than is currently possible in clopidogrel therapy in order to achieve a target therapeutic effect in the subject. A composition or formulation comprising an amount of clopidogrel is administered to a subject, and the corresponding therapeutic effect in the subject is determined within a specified period of time. That period of time will be shorter when the clopidogrel is administered parenterally as a liquid dosage form than when it is administered perorally as a tablet dosage form, e.g. PLAVIX®, tablet. The importance of this advantage relies upon the accepted clinical target to get a patient presenting with ACS from entry into an emergency room or operating room to initiation of a PCI procedure within 90 minutes, specifically doing so while not precluding the utility of CABG by not treating with PLAVIX prior to coronary angiography.

Accordingly, the invention provides a method of escalating dose in a subject to achieve a target therapeutic effect in the subject, the method comprising: parenterally administering to the subject an amount of clopidogrel; within a delay period of less than 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after the parenteral administration, determining the corresponding therapeutic effect achieved in the subject; and if the extent of therapeutic effect achieved is less than the target therapeutic effect, repeating the steps of parenterally administering and determining until the target therapeutic effect is achieved. The steps can be repeated as many times as needed to achieve the target therapeutic effect. The amount of clopidogrel administered will generally be in the range of about 50 to 600 mg, 0.1 to 900 mg, 1 to 900 mg, 10 to 900 mg, 0.1 to 100 mg, 25 to 750 mg, 50 to 600 mg, 75 to 600 mg, 75 to 500 mg, 100 to 300 mg, 100 to 400 mg, 150 to 600 mg, or 200 to 450 mg, 200 to 400 mg, 300 to 600 mg, 300 to 900 mg, 600 to 900 mg, about 0.1 mg, about 0.75 mg, about 1 mg, about 2 mg, about 5 mg, about 7.5 mg, about 10 mg, about 12.5 mg, about 15 mg, about 20 mg, about 25 mg, about 30 mg, about 40 mg, about 50 mg, about 75 mg, about 100 mg, about 150 mg, about 200 mg about 225 mg, about 300 mg, about 375 mg, about 450 mg, about 525 mg, about 600 mg, about 675 mg, about 750 mg, about 900 mg. The delay period is generally 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min. The clopidogrel can be present in an aqueous liquid composition or formulation comprising clopidogrel SAE-CD.

The step of determining can comprise: obtaining a sample of plasma of the subject; and determining the extent of platelet aggregation in the subject's plasma by aggregometry. The step of obtaining can comprise: obtaining a sample of blood of the patient; and separating the plasma from the blood to form a plasma sample, then conducting platelet aggregometry.

The invention also provides a method of escalating dose in a subject to achieve a target therapeutic effect in the subject, the method comprising: perorally administering to the subject an amount of clopidogrel in a composition or formulation comprising clopidogrel and SAE-CD; within a delay period of 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min after the peroral administration, determining the corresponding therapeutic effect achieved in the subject; and if the extent of therapeutic effect achieved is less the target therapeutic effect, repeating the steps of perorally administering and determining until the target therapeutic effect is achieved. The steps can be repeated as many times as needed to achieve the target therapeutic effect. The amount of clopidogrel administered will generally be in the range of 50 to 600 mg, 0.1 to 900 mg, 1 to 900 mg, 10 to 900 mg, 0.1 to 100 mg, 25 to 750 mg, 50 to 600 mg, 75 to 600 mg, 75 to 500 mg, 100 to 300 mg, 100 to 400 mg, 150 to 600 mg, or 200 to 450 mg, 200 to 400 mg, 300 to 600 mg, 300 to 900 mg, 600 to 900 mg, about 0.1 mg, about 0.75 mg, about 1 mg, about 2 mg, about 5 mg, about 7.5 mg, about 10 mg, about 12.5 mg, about 15 mg, about 20 mg, about 25 mg, about 30 mg, about 40 mg, about 50 mg, about 75 mg, about 100 mg, about 150 mg, about 200 mg about 225 mg, about 300 mg, about 375 mg, about 450 mg, about 525 mg, about 600 mg, about 675 mg, about 750 mg, about 900 mg. The delay period is generally 10 sec to 120 min, 30 sec to 120 min, 30 sec to 100 min, 30 sec to 90 min, 30 sec to 60 min, 1 min to 60 min, 1 min to 45 min, 1 min to 30 min, 1 min to 20 min, or 1 min to 15 min, 1 min to 90 min, 5 min to 60 min, 10 min to 60 min, 5 min to 45 min, 10 min to 45 min, 15 min to 30 min, 5 min to 30 min, 5 min to 15 min, or 10 min to 20 min, or within less than about 10 seconds, less than about 1 min, less than about 2.5 min, less than about 5 min, less than about 7.5 min, less than about 10 min, less than about 15 min, less than about 20 min, less than about 30 min, less than about 120 min, less than about 100 min, less than about 90 min, less than about 75 min, less than about 60 min, less than about 50 min, less than about 45 min, or less than about 40 min.

As used herein, the term "about" is taken to mean +/−10% of the indicated value.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

Example 1

The solubility of clopidogrel bisulphate was determined in ~20% w/v of HP-β-CD, SBE-γ-CD, Captisol® (SBE-β-CD), SBE-α-CD, SBE-α-CD, SBE-α-CD, SPE-α-CD, SPE-β-CD SPE-γ-CD, ADVASEP (SBE-β-CD) and α-CD with DS numbers of 7.6, 6.1, 6.6, 2.4, 3.9, 5.4, 5, 5.6, 5.4, 5.5 and 0 (unsubstituted), respectively. This was done according to procedures well known in the art (Higuchi et al. in *Phase Solubility Techniques*, in Advances in Analytical Chemistry and Instrumentation (Ed. C N. Reilly, John Wiley & Sons Inc., Vol. 4 (1965), pg. 117-212) the relevant disclosure of which is hereby incorporated by reference). The results are detailed in the table below.

| Cyclodextrin | Cyclodextrin Molecular Weight (g/mole) | Cyclodextrin Concentration (M) | Clopidogrel Solubilized (M) | Molar Ratio of Clopidogrel to Cyclodextrin |
|---|---|---|---|---|
| HP7.6-β-CD | 1575.8 | 0.117 | 0.005 | 1:23 |
| SBE6.1-γ-CD | 2260.8 | 0.074 | 0.006 | 1:12 |
| SBE6.6-β-CD | 2168 | 0.092 | 0.012 | 1:8 |
| SBE2.4-α-CD | 1358 | 0.141 | 0.0004 | 1:353 |
| SBE3.9-α-CD | 1594 | 0.121 | 0.0008 | 1:151 |
| SBE5.8-α-CD | 1896 | 0.100 | 0.0017 | 1:59 |
| SPE5-α-CD | 1699.2 | 0.100 | 0.001 | 1:100 |
| SPE5.6-β-CD | 1945.72 | 0.076 | 0.005 | 1:15 |
| SPE5.4-γ-CD | 2074.6 | 0.090 | 0.001 | 1:90 |
| SBE5.5-β-CD | 2004 | 0.082 | 0.011 | 1:8 |
| α-CD | 972 | 0.103 | 0.0004 | 1:258 |

Example 2

An aqueous solution of clopidogrel bisulfate was prepared at pH 5.5. The formulation comprised Captisol® (SBE-β-CD, DS=6.6) (39.0% wt./vol.) and clopidogrel bisulfate. The amounts used are specified in the table below.

| Ingredients | Amount |
|---|---|
| Clopidogrel Bisulfate | 300.0 mg (equivalent to 229.9 mg clopidogrel) |
| SBE-β-CD | 39.0 g (anhydrous basis) |
| Sodium Phosphate, monobasic buffer | 0.2M |

The following procedure was used to prepare the formulation. Thirty nine grams of SBE-β-CD were added to approximately 70 ml sodium phosphate, monobasic buffer and dissolved with mixing at room temperature. To this solution, 300 mg of clopidogrel bisulfate was added and dissolved in the solution with stirring. The pH of the solution adjusted as needed with sodium hydroxide to pH 5.5 and the solution was brought to a final volume of 100 ml by the addition of buffer.

Example 3

An aqueous solution of clopidogrel bisulfate was prepared. The formulation contained SBE7-β-CD [DS=6.6] (39% wt./vol). The procedure was identical to that of Example 2 except 0.1M sodium phosphate, monobasic buffer was used instead of a 0.2

M. The final pH was 5.52.

Example 4

An aqueous solution of clopidogrel bisulfate was prepared at pH 7.97. The formulation comprised Captisol® (SBE-β-CD, DS=6.6) (39.0% wt./vol.) and clopidogrel bisulfate. The amounts used are specified in the table below.

| Ingredients | Amount |
|---|---|
| Clopidogrel Bisulfate | 300.0 mg (equivalent to 229.9 mg clopidogrel) |
| SBE-β-CD | 39.0 g (anhydrous basis) |
| Sodium Phosphate, monobasic/dibasic buffer | 0.2M |

The following procedure was used to prepare the formulation. Thirty nine grams of SBE-β-CD were added to approximately 70 ml of sodium phosphate, monobasic/dibasic buffer and dissolved with mixing at room temperature. To this solution 300 mg of clopidogrel bisulfate was added and dissolved in the solution with stirring. The pH of the solution was adjusted as needed with sodium hydroxide to pH 7.97 and the solution was brought to a final volume of 100 ml with buffer.

Example 5

An aqueous solution of clopidogrel bisulfate was prepared. The formulation contained SBE-β-CD [DS=6.6] (39% wt./vol.). The procedure was identical to that of Example 4 except 0.1M sodium phosphate, monobasic/dibasic buffer was used instead of a 0.2 M buffer. The final pH was 8.03.

Example 6

An aqueous solution of clopidogrel bisulfate was prepared at pH 5.50. The formulation comprised HP-β-CD [DS=4.3] (~25.0% wt./vol.) and clopidogrel bisulfate. The amounts used are specified in the table below.

| Ingredients | Amount |
|---|---|
| Clopidogrel Bisulfate | 300.0 mg (equivalent to 229.9 mg clopidogrel) |
| HP-β-CD | 25.0 g (anhydrous basis) |
| Sodium Phosphate, monobasic buffer | 0.2M |

The following procedure was used to prepare the formulation. Twenty five grams of HP-β-CD were added to approximately 70 ml of sodium phosphate, monobasic buffer and dissolved with mixing at room temperature. To this solution, 300 mg of clopidogrel bisulfate was added and dissolved in the solution with stirring. The pH of the solution was adjusted as needed with sodium hydroxide to pH 5.50 and the solution was brought to a final volume of 100 ml with buffer.

Example 7

An aqueous solution of clopidogrel bisulfate was prepared. The formulation contained HP-β-CD [DS=4.3] (25% wt./vol). The procedure was identical to that of Example 6 except 0.1M sodium phosphate, monobasic buffer was used instead of the 0.2 M. The final pH was 5.52.

Example 8

An aqueous solution of clopidogrel bisulfate was prepared at pH ~8.0. The formulation comprised HP-β-CD [DS=4.3] (~25.0% wt./vol.) and clopidogrel bisulfate. The amounts used are specified in the table below.

| Ingredients | Amount |
|---|---|
| Clopidogrel Bisulfate | 300.0 mg (equivalent to 229.9 mg clopidogrel) |
| HP-β-CD | 25.0 g (anhydrous basis) |
| Sodium Phosphate, monobasic/dibasic buffer | 0.2M |

The following procedure was used to prepare the formulation. Twenty five grams of HP-β-CD were added to approximately 70 ml of sodium phosphate, monobasic/dibasic buffer and dissolved with mixing at room temperature. To this solution, 300 mg of clopidogrel bisulfate was added and dissolved in the solution with stirring. The pH of the solution was adjusted as needed with sodium hydroxide to pH of 7.97 and the solution was brought to a final volume of 100 ml with buffer.

Example 9

An aqueous solution containing clopidogrel bisulfate and HP-β-CD [DS=4.3] (25% wt./vol.) was prepared. The procedure was similar to that of Example 8 except 0.1M sodium phosphate, monobasic/dibasic buffer was used instead of the 0.2 M buffer. The final pH was 8.05.

Example 10

An aqueous solution of clopidogrel bisulfate was prepared at pH ~5.50. The formulation comprised Captisol® (SBE7-β-CD, DS=6.6) (37.0% wt./vol.) and clopidogrel bisulfate. The amounts used are specified in the table below.

| Ingredients | Amount |
|---|---|
| Clopidogrel Bisulfate | 2.45 g (equivalent to 1.88 g of clopidogrel) |
| SBE-β-CD | 92.5 g (anhydrous basis) |
| Citric Acid/Sodium Citrate Buffer | 0.2M |

The following procedure was used to prepare the formulation. SBE-β-CD (DS=6.6) (92.5 g) were added to approximately 200 ml of citric acid/sodium citrate buffer (0.2M) and dissolved with mixing at room temperature. To this solution, 2.45 g of clopidogrel bisulfate was added and dissolved in the solution with stirring. The clear solution was brought to a final volume of 250 ml with buffer and a final pH of 5.50.

Example 11

An aqueous solution of clopidogrel bisulfate was prepared. The formulation contained SBE-β-CD [DS=6.6] (37% wt./vol.). The procedure was identical to that of Example 10 except the solution was filled into 10 ml serum vials with a 2.5 ml fill volume. The vials were transferred to a freeze dryer, e.g., FTS Systems' Dura Dry tray dryer attached to a Dura Dry II MP Condenser Module, and lyophilized. The lyophiles were then reconstituted using sterile water to give clear solutions.

Example 12

An aqueous solution of clopidogrel bisulfate was prepared at pH ~5.50. The formulation comprised Captisol® (SBE-β-CD, DS=6.6) (37.0% wt./vol.) and clopidogrel bisulfate. The amounts used are specified in the table below.

| Ingredients | Amount |
|---|---|
| Clopidogrel Bisulfate | 2.45 g (equivalent to 1.88 g of clopidogrel) |
| SBE-β-CD | 92.5 g (anhydrous basis) |
| Citric Acid/Sodium Citrate Buffer | 0.1M |

The following procedure was used to prepare the formulation. 92.5 g of SBE-β-CD were added to approximately 200 ml of citric acid/sodium citrate buffer (0.1M) and dissolved with mixing at room temperature. To this solution, 2.45 g of clopidogrel bisulfate was added and dissolved in the solution with stirring. The clear solution was brought to a final volume of 250 ml with buffer and a pH of 5.48.

Example 13

An aqueous solution of clopidogrel bisulfate was prepared. The formulation contained SBE-β-CD (DS=6.6) (37% wt./vol). The procedure was identical to that of Example 12 except the solution was lyophilized using a freeze dryer e.g. FTS Systems' Dura Dry tray dryer attached to a Dura Dry II MP Condenser Module. The lyophiles were reconstituted using sterile water to give clear solutions.

Example 14

An aqueous solution of clopidogrel bisulfate was prepared. The formulation comprised Captisol® (SBE-β-CD, DS=6.6) at a concentration of 20% wt./vol, excess clopidogrel bisulfate and a surfactant, polysorbate 80 (Tween 80®"* and polyethylene glycol-15-hydroxystearate (Solutol®ˆ. Samples of surfactant (Tween 80® and Solutol®ˆ at different concentrations without any Captisol® (SBE-β-CD, DS=6.6) were also formulated at a pH of about 5.5. The samples were analyzed for clopidogrel content after equilibration by mixing at room temperature of ~20-25° C. for at least 24 hours. The molar amounts added of each component and the resultant clopidogrel amounts assayed in solution are specified in Tables 14a, 14b, 14c and 14d.

TABLE 14a

| Concentration of Captisol | Concentration of Tween 80 | Concentration of Clopidogrel Solubilized | |
|---|---|---|---|
| M (% w/v) | M (% w/v) | M | mg/ml |
| 0.92 (20%) | 0.076 (10%) | 0.029 | 9.22 |
| 0.92 (20%) | 0.038 (5%) | 0.078 | 25.1 |
| 0.92 (20%) | 0.015 (2%) | 0.064 | 20.8 |
| 0.92 (20%) | 0.008 (1%) | 0.056 | 18.1 |
| 0.92 (20%) | 0.004 (0.5%) | 0.023 | 7.40 |
| 0.92 (20%) | 0.00076 (0.1%) | 0.007 | 2.30 |
| 0.92 (20%) | 0 (0%) | 0.015 | 4.69 |

TABLE 14b

| Concentration of Captisol | Concentration of Tween 80 | Concentration of Clopidogrel Solubilized | |
|---|---|---|---|
| M | M (% w/v) | M | mg/ml |
| 0 | 0.076 (10%) | 0.101 | 32.6 |
| 0 | 0.038 (5%) | 0.124 | 39.9 |
| 0 | 0.015 (2%) | 0.050 | 16.0 |
| 0 | 0.008 (1%) | 0.056 | 15.2 |
| 0 | 0.004 (0.5%) | 0.047 | 8.89 |
| 0 | 0.00076 (0.1%) | 0.005 | 1.67 |
| 0 | 0 (0%) | 0.0003 | 0.11 |

TABLE 14c

| Concentration of Captisol | Concentration of Solutol | Concentration of Clopidogrel Solubilized | |
|---|---|---|---|
| M (% w/v) | mg/ml (% w/v) | M | mg/ml |
| 0.92 (20%) | 100 (10%) | 0.071 | 29.8 |
| 0.92 (20%) | 50 (5%) | 0.067 | 28.0 |
| 0.92 (20%) | 25 (2.5%) | 0.043 | 17.6 |
| 0.92 (20%) | 10 (1%) | 0.021 | 8.9 |
| 0.92 (20%) | 0 (0%) | 0.015 | 4.69 |

TABLE 14d

| Concentration of Captisol | Concentration of Solutol | Concentration of Clopidogrel Solubilized | |
|---|---|---|---|
| M | mg/ml (% w/v) | M | mg/ml |
| 0 | 100 (10%) | 0.095 | 30.7 |
| 0 | 50 (5%) | 0.063 | 20.3 |
| 0 | 25 (2.5%) | 0.029 | 9.34 |
| 0 | 10 (1%) | 0.008 | 2.50 |
| 0 | 0 (0%) | 0.015 | 4.69 |

Example 15

A sweetened aqueous solution of clopidogrel bisulfate was prepared. The formulation comprised Captisol® (SBE-β-CD, DS=6.6) (37.7% wt./vol.), clopidogrel bisulfate and mannitol. The amounts used are specified in the table below.

| Ingredients | Amount |
|---|---|
| Clopidogrel Bisulfate | 100 mg (~76.0 mg of clopidogrel) |
| SBE-β-CD | 3.77 g (anhydrous basis) |
| Mannitol | 1.00 g |

The following procedure was used to prepare the formulation. 3.77 g of SBE-β-CD were added to approximately 7 ml of sterile filtered water. To this solution 100 mg of clopidogrel bisulfate and 1.00 g of mannitol were added and dissolved in the solution by vortexing. The solution was brought to a final volume of 10 ml. Two milliliters of the solution were placed in a 10 ml sterile vial and lyophilized using a freeze dryer e.g. FTS Systems' Dura Stop tray dryer attached to a Dura Dry II MP Condenser Module. The lyophile was reconstituted using sterile filtered water to give a clear solution with a final pH of 1.80.

Example 16

The formulation comprised Captisol® (SBE-β-CD, DS=6.6) (~37%), clopidogrel bisulfate and mannitol. The procedure was similar to that of Example 15 except, 200 mg of clopidogrel bisulfate (152 mg clopidogrel) was used. The reconstituted lyophile was a clear solution with a pH of 1.52.

Example 17

An aqueous solution of clopidogrel bisulfate was prepared. The formulation comprised Captisol® (SBE-β-CD, DS=6.6) (~37%), clopidogrel bisulfate and D-glucose. The procedure was similar to that of Example 15 except, D-glucose was used instead of mannitol and the final pH after reconstitution was 1.81. The reconstituted solution was clear.

Example 18

The formulation comprised Captisol® (SBE-β-CD, DS=6.6) (~37%), clopidogrel bisulfate and D-glucose. The procedure was similar to that of Example 17 except, 200 mg of clopidogrel bisulfate (152 mg clopidogrel) was used. The reconstituted lyophile was a clear solution with a pH of 1.82.

Example 19

The stability of clopidogrel liquid formulations was determined after exposure to stress by either heat or fluorescent light. The formulations contained clopidogrel bisulfate and equimolar amounts of different cyclodextrins or cyclodextrin derivatives. All formulations contained 3.0 mg/ml clopidogrel bisulfate, equivalent to 2.29 mg/ml clopidogrel free base and cyclodextrin at 0.18 M. The cyclodextrin formulations were prepared by dissolving the appropriate amount of cyclodextrin in 70 ml of sodium phosphate monobasic/dibasic buffer (0.1M and 0.2M), adding the clopidogrel, and mixing until all the clopidogrel was dissolved. The solutions were brought to a final volume of 100 ml with phosphate buffer then passed through a 0.22 micron Millex-GV Durapore filter. The solutions were evaluated at both pH ~5.5 and pH ~8.0 and at two temperatures, 60° C. and 40° C. Each of the solutions was analyzed for content of clopidogrel and presence of degradants by HPLC. Aliquots (1.5 ml) of each solution were also placed in 1 dram glass vials with Teflon-lined screw-caps and stored exposed to high intensity fluorescent light (~25 cm from a bank of Sylvania Cool White 15 watt lamps) for 9 days. At the end of the 9 day storage period, each of the samples were assayed by the HPLC method and the amounts of each of the main degradants calculated as a percentage of clopidogrel peak area appearing in the chromatogram.

The samples were analyzed using a Perkin-Elmer HPLC system using a β-cyclodextrin column 200×4.0 mm and a mobile phase containing 65% Methanol: 35% 0.1% triethyl ammonium acetate solution at pH ~4 flowing at 0.7 ml/min.

Detection was by UV absorption at 230 nm. Clopidogrel retention time was ~18 minutes using this analytical system.

Example 20

An aqueous solution of clopidogrel bisulfate was prepared. The formulation comprised Captisol® (SBE-β-CD, DS=6.6) (19.0% wt./vol.) and clopidogrel bisulfate. The amounts used are specified in the table below.

| Ingredients | Amount |
| --- | --- |
| Clopidogrel Bisulfate | 150.8 mg (equivalent to 115.6 mg of clopidogrel) |
| SBE-β-CD | 9.52 g (anhydrous basis) |

To prepare the formulation, 9.52 grams of SBE-β-CD were added to approximately 30 ml of sterile filtered water and dissolved with mixing at room temperature. To this solution 150.8 mg of clopidogrel bisulfate were added and dissolved in the solution with stirring. The solution was brought to a final volume of 50 ml and the pH was adjusted to 5.47. The density of the solution was determined to be 1.011 g/cc. Aliquots of 2.5 ml of the solution were placed in 10 ml Schott glass vials and freeze-dried. The samples were then used for the in-vivo bleeding study described in Example 21.

Example 21

A bleeding time study was performed using mice as the model animal. The mice were administered clopidogrel-containing formulations either by injection into the tail vein or by oral gavage of doses of 0.1 ml per 20 gram mouse. This is equivalent to doses of 6.5 mg/kg clopidogrel bisulfate (equivalent to 5 mg/kg clopidogrel base). At selected times after dosing, a standardized transection of the tip (0.3 mm) of each tail was performed then the mice were immediately suspended vertically with the distal 2 cm of each tail immersed in a test tube containing saline at 37° C. The time required for beginning a 15 second period of bleeding cessation was then determined. A maximum cessation time of 180 seconds was used.

The SBE-β-CD-Clopidogrel formulations from Example 20 were prepared by reconstituting each vial with 5.1 ml sterile water for injection (calculated using the density of solution and water) resulting in solutions containing 1.3 mg/ml clopidogrel bisulfate. The solutions were agitated well until all the solid had dissolved. This solution formulation was used for both intravenous and oral solution dosing.

PLAVIX® the commercially available drug product was delivered as an oral suspension in methylcellulose. One tablet was ground up and suspended in 37.5 ml of 0.5% w/v methylcellulose to give a suspension containing 1.3 mg/ml clopidogrel bisulfate. The PLAVIX® suspension was delivered orally.

Aspirin at 100 mg/kg was used as a positive control.

The sampling regimen is as shown in the table below.

| Sample | # of Mice per Timepoint | Timepoints |
| --- | --- | --- |
| Aspirin Control | 5 | 30 min |
| SBE-β-CD - Clopidogrel (oral) | 5 | 5, 10, 20, 30 min |
| SBE-β-CD - Clopidogrel (IV) | 5 | 5, 10, 20, 30 min |
| PLAVIX ® marketed product (Tablet) ground and suspended in methylcellulose | 5 | 5, 10, 20, 30 min |

Example 22

The competitive binding study was conducted using clopidogrel bisulphate and aspirin (ASA, acetyl salicylic acid). The work was conducted on an auto-titrator such that the pH was maintained at ~5.5 using sodium hydroxide. The required amount of SBE-β-CD and aspirin was first solubilized in 0.2 μm Millipore filtered water then transferred to the auto-titrator. To this solution, excess clopidogrel bisulfate was added and allowed to equilibrate for 2 hours while stirring and maintaining the pH ~5.5. The amounts of SBE-β-CD and aspirin are shown in the table below.

| SBE-β-CD Content M (mg/ml) | Aspirin Content M (mg/ml) |
| --- | --- |
| 0.0134 (29.1 mg/ml) | 0.042 (7.5 mg/ml) |
| 0.0125 (272 mg/ml) | 0.111 (20 mg/ml) |
| 0.0123 (268 mg/ml) | 0.166 (30 mg/ml) |
| 0.0161 (34.8 mg/ml) | No Aspirin |

After equilibration, the solutions were sampled and analyzed for clopidogrel content.

Example 23

Dissolution of the SBE-β-CD-clopidogrel bisulfate based formulation was compared to the marketed PLAVIX formulation. Two forms of the clopidogrel formulation were made.

In the first formulation, a preformed complex of Captisol and clopidogrel bisulfate was made by solubilizing SBE-β-CD (2.5 g) in 100 ml of sterile filtered water. To this, clopidogrel bisulfate (980 mg) was added. The solution was then spray dried using a Buchi 190 mini spray dryer.

The second formulation comprised a physical mixture of SBE-β-CD (2.5 g) and clopidogrel bisulfate (980 mg), where the two ingredients were weighed out and thoroughly mixed together in the solid state just prior to tableting. Magnesium stearate was added to the formulations as a lubricant prior to tableting.

Each tablet contained magnesium stearate (0.5% wt/wt), SBE-β-CD (250 mg) and clopidogrel bisulfate (98 mg, which is equivalent to 75 mg of the free base clopidogrel). This correlates with the marketed product PLAVIX® which has 75 mg of free base clopidogrel.

A comparative dissolution analysis was done using a Vankel vk7000 dissolution apparatus. The paddle method was employed spinning at 50 rpm and media temperature maintained at 37° C. The dissolution media was 1000 ml of a citric acid/disodium phosphate buffer at pH ~5.4. Each tablet was tested in triplicate, and the sampling times were 5, 15, 30, 45 and 60 minutes with each sample being filtered through a 35 μm filter. These samples were then assayed for clopidogrel bisulfate content.

Example 24

An aqueous solution of clopidogrel bisulfate and tirofiban hydrochloride monohydrate is prepared at pH ~5.5. The formulation comprised Captisol® (SBE-β-CD, DS=6.6) (39.0% wt./vol.), clopidogrel bisulfate and tirofiban hydrochloride monohydrate. The amounts used are specified in the table below.

| Ingredients | Amount |
| --- | --- |
| Clopidogrel Bisulfate | 100 mg (equivalent to ~76.0 mg of clopidogrel) |
| Tirofiban hydrochloride monohydrate | 0.449 mg (equivalent to 0.4 mg tirofiban) |
| SBE-β-CD | 3.90 g (anhydrous basis) |

The following procedure is use to prepare the formulation. SBE-β-CD (3.90 g) is added to sterile water (approximately 7 ml) and dissolved with mixing at room temperature. To this solution, clopidogrel bisulfate (100 mg) is added and dissolved in the solution with stirring. Then tirofiban hydrochloride monohydrate (0.449 mg) is dissolved in the solution, and the pH is adjusted as needed to pH ~5.5 with sodium hydroxide. The solution is brought to a final volume of 10.0 ml by the addition of sterile water.

Example 25

An aqueous solution of clopidogrel bisulfate and enoxaparin sodium is prepared at pH ~5.5. The formulation comprises Captisol® (SBE-β-CD, DS=6.6) (39.0% wt./vol.), clopidogrel bisulfate and enoxaparin sodium. The amounts used are specified in the table below.

| Ingredients | Amount |
| --- | --- |
| Clopidogrel Bisulfate | 100 mg (equivalent to ~76.0 mg of clopidogrel) |
| Enoxaparin Sodium | 10.5 mg |
| SBE-β-CD | 3.90 g (anhydrous basis) |

The following procedure is used to prepare the formulation. SBE-β-CD (3.90 g) is added to sterile water (approximately 7 ml) and dissolved with mixing at room temperature. To this solution, clopidogrel bisulfate (100 mg) is added and dissolved in the solution with stirring. Then, enoxaprin sodium (10.5 mg) is dissolved, and the pH is adjusted as needed to pH ~5.5 with sodium hydroxide or hydrochloric acid. The solution is brought to a final volume of 10.0 ml by the addition of sterile water.

Example 26

A fresh whole blood sample is collected from a subject and platelet aggregation is measured with the point-of-care MICROS cell counter (ABX Diagnostics) and the Plateletworks test platform (Helena Laboratories). The cell counter uses traditional electronic impedance cell counting principles where a reference platelet count is performed on 1 mL of fresh whole blood in a Plateletworks tube containing $K_3$-EDTA as the anticoagulant. The sample is then passed through the cell counter and the platelet count is determined. This process is repeated with a second 1 mL sample of fresh whole blood in a Plateletworks tube containing both citrate and 20 μmol/L ADP (Adenosine-5'-Diphosphate, the agonist). In the presence of ADP, platelets associate and aggregate. As the aggregated platelets exceed the threshold limitations for platelet size, they are no longer counted as individual platelets. The ratio of the platelet count between the agonist and reference tubes is calculated as percent platelet aggregation.

Example 27

A open-label, dose-escalation clinical trial was conducted in healthy adult volunteers to determine the platelet aggregation inhibition effects and pharmacokinetics of an aqueous liquid formulation of the invention as follows. The data obtained from this study are detailed in FIGS. 10-14 and discussed in further detail above.
Objectives:
To assess the safety and tolerability of single ascending doses of PM 103 I.V.
To determine the dose-response of PM 103 I.V. for inhibition of ADP-induced, platelet aggregation.
To measure plasma concentrations of clopidogrel, clopidogrel carboxylic acid, and clopidogrel thiol in plasma.
Design:
An open-label, ascending dose escalation study of six planned single intravenous doses of PM103 I.V. (0.1 mg, 1.0 mg, 10 mg, 30 mg, 100 mg and 300 mg, clopidogrel).
Treatments:
Treatment: PM103 I.V. (clopidogrel bisulfate); 0.1, 1.0, 10, 30 mg, 100 mg or 300 mg
Subjects:
72 healthy male or female volunteers (12 per cohort) 18 years of age and older were enrolled to the following planned cohorts based on subject tolerability:
Cohort 1: PM103 I.V. 0.1 mg, single dose
Cohort 2: PM103 I.V. 1.0 mg, single dose
Cohort 3: PM 103 I.V. 10 mg, single dose
Cohort 4: PM 103 I.V. 100 mg, single dose
Cohort 5: PM 103 I.V. 30 mg, single dose
Cohort 6: PM103 I.V. 300 mg, single dose
Inclusion Criteria:
Be a healthy male or female 18 years of age and older. Women of childbearing potential must be using a medically acceptable form of birth control for the duration of the trial and must have a negative serum pregnancy test at screening and upon check-in to the study facility.
Have a BMI within the range of 18-35 kg/m², inclusive.
Be able to communicate effectively with the study personnel.
Have no significant disease or abnormal laboratory values as determined by medical history, physical examination or laboratory evaluations, conducted at the screening visit or on admission to the clinic.
Have a normal 12-lead electrocardiogram, without any clinically significant abnormalities of rate, rhythm or conduction.
Be nonsmokers defined as not having smoked in the past 6 months prior to dosing.
Be adequately informed of the nature and risks of the study and give written informed consent prior to receiving study medication.
Have a normal platelet count >125,000/μL
Procedures:
PLAVIX® Pre-Screen:
Subjects who successfully meet the screening criteria were scheduled for a clopidogrel dose effectiveness screen. The subject received a single oral dose of PLAVIX® (300 mg) and was monitored for safety and tolerability and had platelet aggregation assessments performed predose (Screening Baseline) and at 2 hours after dosing.
Main Study:
Cohorts 1, 2, 3, 4 and 6 included two Phases. Phase 1 consisted of two subjects. Phase 2 was dosed no less than 24 hours after Phase 1 (assuming no safety concerns) and consisted of ten subjects. Study procedures were the same for both Phases. Cohort 5 consisted of twelve subjects and all subjects were dosed on the same day. The procedures for this study were as follows:

After a minimum post screening washout period of 14 days (including no use of aspirin, other non-steroidal anti-inflammatory drugs, or other drugs known to affect platelet function) each eligible subject returned to the clinic on the evening of Day −1. On Day 1 subjects will receive PM 103 I.V.

At approximately 1 hour prior to dosing, an IV port was inserted into the antecubital region of the arm used for dosing (arm #1). For 0.1 mg (Cohort 1), 1.0 mg (Cohort 2), 10 mg (Cohort 3), and 30 mg (Cohort 5), at Time=0, a syringe containing PM 103 I.V. was attached to the IV port and the study formulation was administered as a bolus push injection (IV push). For the 100 mg dose (Cohort 4), at Time=0, a glass bottle containing PM 103 I.V. 100 mg in 40 mL was attached to the IV port and the study drug was administered as an infusion over 4 minutes (10 mL/min). For the 300 mg dose (Cohort 6), at Time=0, a glass bottle containing PM103 I.V. 300 mg in 120 mL was attached to the IV port and the study drug was administered as an infusion over 8 minutes (15 mL/min). Immediately after the study drug administration was completed, the LV port was flushed with 3 mL of NSS and remained in the arm until the port was removed 1 hour after dose initiation. Subjects were discharged from the clinic on Day 2 following collection of the 24-hour blood sample. Subjects came back at the clinic approximately 36 hours post-dose (on Day 2) for assessment of adverse events.

Dosing in Cohort 1 (0.1 mg), Cohort 2 (1.0 mg) and Cohort 3 (10 mg) was separated by at least 7 days to enable safety and effectiveness evaluations prior to proceeding to the next dose level. Cohort 4 (100 mg) was dosed at least 14 days following Cohort 3. Cohort 5 (30 mg) was dosed at least 7 days following Cohort 4. Cohort 6 (300 mg) was dosed at least 7 days following Cohort 5.

Pharmacokinetics:

Plasma samples for determination of clopidogrel, clopidogrel carboxylic acid, and clopidogrel thiol concentrations were obtained from arm #2 (the arm not used for dosing) at baseline (pre-dose), 1, 5, 10, 20 and 30 minutes, and 1, 2, 3, 4, 6, 8, 12, and 24 hours after dose initiation.

Pharmacokinetic variables were calculated for clopidogrel, clopidogrel carboxylic acid, and clopidogrel thiol using standard, non-compartmental methods. Calculations were conducted using WinNonlin (version 5.0.1). Standard variables were expected to include Cmax, Tmax, and AUCT. Variables λz, T1/2, and AUC were computed whenever sufficient points were available in the terminal portion of the concentration versus time curve.

Pharmacodynamics:

Blood samples for determination of ADP-induced platelet aggregation inhibition using the impedance method (see Dyszkiewicz-Korpanty et al. above) were obtained from arm #2 (the arm not used for dosing) at baseline (check-in, Day −1), 15 and 30 minutes, and 2, 5, and 24 hours after dose initiation.

Statistical Analysis:

All pharmacokinetic results were summarized by treatment group using appropriate descriptive statistics. Dose proportionality was assessed using a plot of mean AUC, AUCT, and Cmax by dose level.

The ADP-induced platelet aggregation inhibition results using the impedance method were summarized by treatment group and time point. Maximum % platelet inhibition and area under the % platelet inhibition curve was calculated for each individual and summarized by treatment group Safety Evaluations:

All safety variables (including adverse events, vital signs measurements, clinical laboratory results, electrocardiogram results, and other safety variables) were listed by subject and domain. The incidence of all adverse events (AEs), treatment-emergent adverse events, and treatment-related adverse events were tabulated by MedDRA™ preferred term, system organ class, and treatment group. All laboratory results, vital sign measurements, and other safety variables were summarized using appropriate descriptive statistics. The incidence of treatment emergent laboratory abnormalities were summarized and listed by laboratory test. No hypothesis testing were performed.

All references cited herein are incorporated by reference.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except by the appended claims. All of the embodiments disclosed and claimed herein can be made and executed without undue experimentation in light of the present disclosure.

What is claimed is:

1. A method of improving the stability of clopidogrel in a composition comprising clopidogrel, the method comprising adding a sulfoalkyl ether cyclodextrin (SAE-CD) of Formula 1:

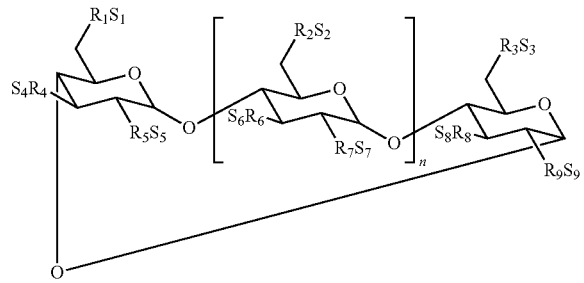

Formula 1 wherein: n is 4, 5, or 6; $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group, wherein at least one of $R_1$ to $R_9$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a pharmaceutically acceptable cation, to the composition, wherein the molar ratio of SAE-CD to clopidogrel is between 6:1 to 500:1.

2. The method of claim 1, wherein the rate of chiral inversion of clopidogrel in the presence of the SAE-CD is reduced as compared to the rate of chiral inversion in the presence of an equimolar amount of HP-CD.

3. The method of claim 1, wherein the stability of clopidogrel against hydrolytic degradation is improved.

4. The method of claim 1, wherein the stability of clopidogrel against enzymatic degradation is improved.

5. The method of claim 1, wherein the stability of clopidogrel against photolytic degradation is improved.

6. The method of claim 1, wherein the stability of clopidogrel against thermolytic degradation is improved.

7. The method of claim 1, wherein the stability of clopidogrel against microbial degradation is improved.

8. The method of claim 1, wherein the molar ratio of SAE-CD to clopidogrel is between 6:1 to 50:1.

9. The method of claim 1, wherein the clopidogrel is present in an amount between 10 milligrams to 600 milligrams.

10. The method of claim 1, wherein the composition is a liquid composition.

* * * * *